(12) United States Patent
Suh et al.

(10) Patent No.: US 8,198,307 B2
(45) Date of Patent: Jun. 12, 2012

(54) IMIDAZOLE DERIVATIVES HAVING ARYL PIPERIDINE SUBSTITUENT, METHOD FOR PREPARATION THEREOF AND PHARMACEUTICAL COMPOSITIONS CONTAINING SAME

(75) Inventors: Jee Hee Suh, Daejeon (KR); Kyu Yang Yi, Daejeon (KR); Nack Jeong Kim, Daejeon (KR); Sung Eun Yoo, Gongju-so (KR); Kwang-Seok Oh, Daejeon (KR); Hyae Gyeong Cheon, Daejeon (KR); Mija Ahn, Daejeon (KR); Byung Ho Lee, Daejeon (KR); Won Hoon Jung, Daejeon (KR); Sang Dal Rhee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 326 days.

(21) Appl. No.: 12/599,005

(22) PCT Filed: May 13, 2008

(86) PCT No.: PCT/KR2008/002653
§ 371 (c)(1),
(2), (4) Date: Jan. 25, 2010

(87) PCT Pub. No.: WO2008/140239
PCT Pub. Date: Nov. 20, 2008

(65) Prior Publication Data
US 2010/0145054 A1 Jun. 10, 2010

(30) Foreign Application Priority Data

May 11, 2007 (KR) .......................... 10-2007-0046064
May 11, 2007 (KR) .......................... 10-2007-0046073
May 11, 2007 (KR) .......................... 10-2007-0046077

(51) Int. Cl.
| C07D 471/04 | (2006.01) |
| C07D 417/14 | (2006.01) |
| C07D 413/14 | (2006.01) |
| C07D 409/14 | (2006.01) |
| C07D 405/14 | (2006.01) |
| C07D 403/14 | (2006.01) |
| C07D 403/06 | (2006.01) |
| A61K 31/4545 | (2006.01) |
| A61K 31/454 | (2006.01) |

(52) U.S. Cl. ....................................................... 514/322
(58) Field of Classification Search .................. 514/322, 514/318, 303; 546/118, 194, 199
See application file for complete search history.

(56) References Cited

U.S. PATENT DOCUMENTS
| 6,232,329 B1 | 5/2001 | Merce-Vidal |
| 6,355,659 B1 | 3/2002 | Merce-Vidal |
| 2002/0103208 A1 | 8/2002 | Cereda et al. |

FOREIGN PATENT DOCUMENTS
| EP | 0526434 A1 | 2/1993 |
| WO | 96/04287 A1 | 2/1996 |
| WO | WO 9604287 A1 * | 2/1996 |
| WO | 02/24662 A1 | 3/2002 |

OTHER PUBLICATIONS

Daqing Qu et al., "A role for melanin-concentrating hormone in the central regulation of feeding behaviour", Letters to Nature, Mar. 21, 1996, pp. 243-247, vol. 380.
Anthony L. Handlon et al., "Melanin-Concentrating Hormone-1 Receptor Antagonists for the Treatment of Obesity", Journal of Medicinal Chemistry, 2006, pp. 4017-4022, vol. 49, No. 14.
Beth Borowsky et al., "Antidepressant, anxiolytic and anoretics effects of a melanin-concentrating hormone-1 receptor antagonist", Nature Medicine, Aug. 2002, pp. 825-830, vol. 8, No. 8.
David S. Ludwig et al., "Melanin-concentrating hormone overexpression in transgenic mice leads to obesity and insulin resistance", The Journal of Clinical Investigation, Feb. 2001, pp. 379-386, vol. 107, No. 3.
Brian Dyck et al., "Substituted chromones and quinolones as potent melanin-concentrating hormone receptor 1 antagonists", Bioorganic & Medicinal Chemistry Letters 16, 2006, pp. 4237-4242.
Trisha Gura "Obesity Drug Pipeline Not So Fat", Science, Feb. 7, 2003, pp. 849-852, vol. 299.

* cited by examiner

Primary Examiner — Joseph Kosack
Assistant Examiner — Matthew Coughlin
(74) Attorney, Agent, or Firm — Sughrue Mion, PLLC

(57) ABSTRACT

The present invention is directed to a novel imidazole derivative having an aryl piperidine substituent of formula (I) and a method for preparation thereof, and a pharmaceutical composition containing said imidazole derivative as an active ingredient for preventing or treating a MCH (melanine-concentrating hormone)-related disease.

17 Claims, No Drawings

IMIDAZOLE DERIVATIVES HAVING ARYL PIPERIDINE SUBSTITUENT, METHOD FOR PREPARATION THEREOF AND PHARMACEUTICAL COMPOSITIONS CONTAINING SAME

CROSS REFERENCE TO RELATED APPLICATION

This application is a National Stage of International Application No. PCT/KR2008/002653 filed May 13, 2008, claiming priority based on Korean Patent Application Nos. 10-2007-0046077, 10-2007-0046073, and 10-2007-0046064, filed May 11, 2007 respectively, the contents of all of which are incorporated herein by reference in their entirety.

FIELD OF THE INVENTION

The present invention relates to a novel imidazole derivative having an aryl piperidine substituent, a method for preparation thereof, and a pharmaceutical composition containing same.

BACKGROUND OF THE INVENTION

The occurrence of obesity in adults as well as children has rapidly increased over the last ten years, which has raised the risk of associated health problems including Type 2 diabetes, heart diseases, cancer, hypertension. Accordingly, many studies for obesity treatment have been performed.

Melanine-concentrating hormone (MCH) is a cyclic 19 amino acid peptide that has been implicated to be involved in the regulation of feeding behavior of a mammal. Studies with MCH-administered rat models have shown an increase in food intake, while MCH-deficient mice undergo weight loss due to a significant decrease in the food intake and an increase in the metabolic rate (see D. Qu et al., *Nature*, 380 (6571), 243-247, 1996). Also, the effect of MCH in regulating the feeding behavior is known to be attributed to MCH receptor-1 which stimulates feeding, and obesity in MCH receptor-1 knock-out mice does not take place even after MCH administration (see A. L. Handlon and H. Zhou, *J. Med. Chem.* 49, 4017-4022, 2006).

Meanwhile, the effect of MCH is mediated by an MCH receptor-1 antagonist which is one of G-protein-coupled receptors. Such a MCH receptor-1 antagonist is also reported to be useful in treating depression and anxiety (see B. Borowsky et al., *Nature Medicine*, 8(8), 825-830, 2002), and also diabetes and metabolic disturbance (see D. S. Ludwig et al., *J. Clin. Invest.* 107, 379-386, 2001).

A specific MCH receptor-1 antagonist, GW3430, developed by Amgen and GlaxoSmithKline is currently undergoing clinical evaluation for the treatment of obesity (see Dyck et al, *Bioorg. Med. Chem, Lett.* 2006, 16, 4237-4242).

Also, Xenical® and Reductil®, the structures of which are shown below, are marketed as drugs for obesity treatment. However, they show unsatisfactory therapeutic effects and cause undesirable side effects (see Trisha Gura, *Science* 2003, 299, 849-852).

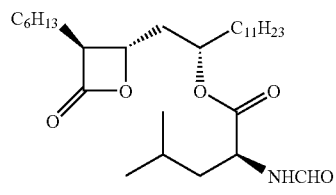
Xenical

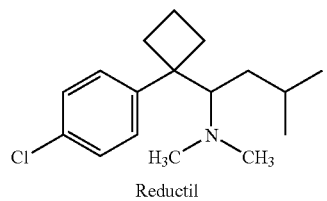
Reductil

Accordingly, the present inventors have endeavored to develop a novel MCH receptor-1 antagonist and found that an imidazole derivative having a specific structure is capable of acting as an effective MCH receptor-1 antagonist to be useful for preventing or treating MCH-related diseases including obesity.

SUMMARY OF THE INVENTION

It is a primary object of the present invention to provide a novel imidazole derivative having an aryl piperidine substituent and a method for preparing the same.

It is another object of the present application to provide a pharmaceutical composition containing said imidazole derivative as an active ingredient for preventing or treating MCH-related diseases.

In accordance with one aspect of the present invention, there is provided an imidazole derivative having aryl piperidine substituents of formula (I) or a pharmaceutically acceptable salt thereof:

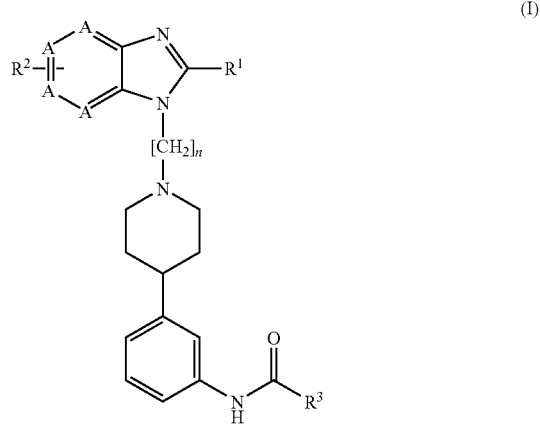

(I)

wherein
$R^1$ is

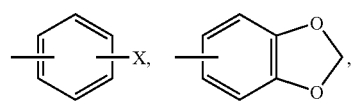

$C_{1-4}$ alkyl,

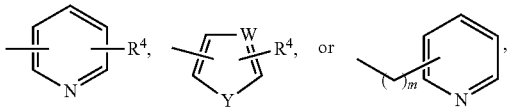

in which X is H, halogen, $OR^5$, $C_{1-4}$ alkyl, $CF_3$, phenyl, CN, $NO_2$, $—CO_2R^6$, or $—CONR^7R^8$, $R^5$, $R^6$, $R^7$ and $R^8$ being each independently H, halogen, $C_{1-3}$ alkyl, or phenyl;

$R^4$ is H, halogen, $C_{1-3}$ alkyl, $C_{1-3}$ alkoxy, phenyl, or phenyl having at least one halogen or methyl substituent;

W is CH or N;

Y is O, S, or $NR^9$, $R^9$ being H or $C_{1-3}$ alkyl;

m is 1 or 2;

$R^2$ is at least one selected from the group consisting of H, halogen, $C_{1-3}$ alkyl

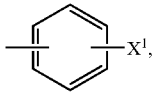

phenyl, $OR^5$, $NO_2$, CN, pyridyl, CHO, and $—CONR^7R^8$, in which $X^1$ is H, halogen, $C_{1-3}$ alkyl, $OR^5$, or $NO_2$, and $R^5$, $R^7$, and $R^8$ are the same as defined above;

$R^3$ is $C_{1-3}$ alkyl, phenyl, or phenyl having at least one halogen or methyl substituent;

A is CH or N, with the proviso that the number of N representing A does not exceed 2; and n is an integer of 2 to 5.

DETAILED DESCRIPTION OF THE INVENTION

The present invention provides a novel compound of formula (I) or a pharmaceutically acceptable salt thereof as a MCH receptor-1 antagonist.

Among the compounds of formula (I) of the present invention, preferred are those wherein $R^1$ is

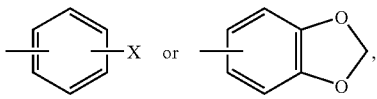

in which X is H, halogen, $OR^5$, $C_{1-4}$ alkyl, $CF_3$, phenyl, CN, $NO_2$, $—CO_2R^6$, or $—CONR^7R^8$, $R^5$, $R^6$, $R^7$ and $R^8$ being each independently H, halogen, $C_{1-3}$ alkyl, or phenyl; and $R^2$ is at least one selected from the group consisting of H, halogen, $C_{1-3}$ alkyl, phenyl, $OR^5$, $NO_2$, CN, pyridyl, and $—CONR^7R^8$, in which $R^3$, $R^5$, $R^7$, $R^8$, A and n are the same as defined above.

In another embodiment of the compounds of formula (I), preferred are those wherein $R^1$ is $C_{1-4}$ alkyl;

$R^2$ is at least one selected from the group consisting of H, halogen, $C_{1-3}$ alkyl,

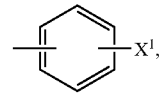

$OR^5$, $NO_2$, CN, pyridyl, CHO, and $—CONR^7R^8$, in which $X^1$ is H, halogen, $C_{1-3}$ alkyl, $OR^5$, or $NO_2$, and $R^5$, $R^7$ and $R^8$ are each independently H, $C_{1-3}$ alkyl, or phenyl; and $R^3$, A and n are the same as defined above.

In another embodiment of the compounds of formula (I), preferred are those wherein $R^1$ is

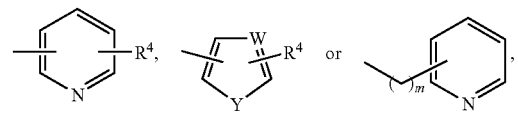

in which $R^4$ is H, halogen, $C_{1-3}$ alkyl, $C_{1-3}$ alkoxy, phenyl, or phenyl having at least one halogen or methyl substituent;

W is CH or N;

Y is O, S or $NR^9$, in which $R^9$ is H or $C_{1-3}$ alkyl;

m is 1 or 2;

$R^2$ is at least one selected from the group consisting of H, halogen, $C_{1-3}$ alkyl, phenyl, $OR^5$, $NO_2$, CN, pyridyl, and $—CONR^7R^8$, $R^5$, $R^7$ and $R^8$ being each independently H, $C_{1-3}$ alkyl, or phenyl; and $R^3$, A and n are the same as defined above.

The inventive compound of formula (I) may be used in the form of a pharmaceutically acceptable addition salt formed with a free acid such as an organic or inorganic acid. Examples of such inorganic acid include hydrochloric, bromic, sulfuric, sulfurous and phosphoric acids, preferably hydrochloric acid, while the organic acid may be citric, acetic, maleic, fumaric, gluconic, methanesulfonic, glycolic, succinic, tartaric, 4-toluenesulfonic, galacturonic, embonic, glutamic and aspartic acids, preferably methanesulfonic acid.

The addition salt according to the present invention may be prepared by a conventional method, e.g., by dissolving the compound of formula (I) in a water-miscible organic solvent (e.g., acetone, methanol, ethanol and acetonitrile) and adding thereto an organic or inorganic acid specified above in an equivalent or excessive amount, followed by isolating the salt transformed.

The present invention also includes a solvate, hydrate and stereoisomer of the compound of formula (I).

Exemplary compounds of formula (I) according to the present invention are as follows and each structure thereof is shown in Table 1:

1) 2-phenyl-1-{2-[4-(3-acetylaminophenyl)piperidin-1-yl]ethyl}-1H-benzimidazole;
2) 2-(4-chlorophenyl)-1-{2-[4-(3-acetylaminophenyl)piperidin-1-yl]ethyl}-1H-benzimidazole;
3) 2-phenyl-1-{3-[4-(3-acetylaminophenyl)piperidin-1-yl]propyl}-1H-benzimidazole;
4) 2-(4-chlorophenyl)-1-{3-[4-(3-acetylaminophenyl)piperidin-1-yl]propyl}-1H-benzimidazole;
5) 2-phenyl-1-{4-[4-(3-acetylaminophenyl)piperidin-1-yl]butyl}-1H-benzimidazole;
6) 2-(4-chlorophenyl)-1-{4-[4-(3-acetylaminophenyl)piperidin-1-yl]butyl}-1H-benzimidazole;
7) 2-phenyl-1-{5-[4-(3-acetylaminophenyl)piperidin-1-yl]pentyl}-1H-benzimidazole;

8) 2-(4-chlorophenyl)-1-{5-[4-(3-acetylaminophenyl)piperidin-1-yl]pentyl}-1H-benzimidazole;
9) 2-(2-chlorophenyl)-1-{3-[4-(3-acetylaminophenyl)piperidin-1-yl]propyl}-1H-benzimidazole;
10) 2-(3-chlorophenyl)-1-{3-[4-(3-acetylaminophenyl)piperidin-1-yl]propyl}-1H-benzimidazole;
11) 2-(4-bromophenyl)-1-{3-[4-(3-acetylaminophenyl)piperidin-1-yl]propyl}-1H-benzimidazole;
12) 2-(3,4-dichlorophenyl)-1-{3-[4-(3-acetylaminophenyl)piperidin-1-yl]propyl}-1H-benzimidazole;
13) 2-(3-bromophenyl)-1-{3-[4-(3-acetylaminophenyl)piperidin-1-yl]propyl}-1H-benzimidazole;
14) 2-(2-iodophenyl)-1-{3-[4-(3-acetylaminophenyl)piperidin-1-yl]propyl}-1H-benzimidazole;
15) 2-(2-fluorophenyl)-1-{3-[4-(3-acetylaminophenyl)piperidin-1-yl]propyl}-1H-benzimidazole;
16) 2-(2,4-dichlorophenyl)-1-{3-[4-(3-acetylaminophenyl)piperidin-1-yl]propyl}-1H-benzimidazole;
17) 2-(2-methoxyphenyl)-1-{3-[4-(3-acetylaminophenyl)piperidin-1-yl]propyl}-1H-benzimidazole;
18) 2-(3-methoxyphenyl)-1-{3-[4-(3-acetylaminophenyl)piperidin-1-yl]propyl}-1H-benzimidazole;
19) 2-(4-methoxyphenyl)-1-{3-[4-(3-acetylaminophenyl)piperidin-yl]propyl}-1H-benzimidazole;
20) 2-(4-isopropylphenyl)-1-{3-[4-(3-acetylaminophenyl)piperidin-1-yl]propyl}-1H-benzimidazole;
21) 2-phenyl-1-{3-[4-(3-acetylaminophenyl)piperidin-1-yl]propyl}-5,6-dimethyl-1H-benzimidazole;
22) 2-(4-chlorophenyl)-1-{3-[4-(3-acetylaminophenyl)piperidin-1-yl]propyl}-5,6-dimethyl-1H-benzimidazole;
23) 2-phenyl-1-{3-[4-(3-acetylaminophenyl)piperidin-1-yl]propyl}-6-methyl-1H-benzimidazole;
24) 2-(4-chlorophenyl)-1-{3-[4-(3-acetylaminophenyl)piperidin-1-yl]propyl}-6-methyl-1H-benzimidazole;
25) 2-(4-chlorophenyl)-1-{3-[4-(3-acetylaminophenyl)piperidin-1-yl]propyl}-6-chloro-1H-benzimidazole;
26) 2-phenyl-1-{3-[4-(3-acetylaminophenyl)piperidin-1-yl]propyl}-6-fluoro-1H-benzimidazole;
27) 2-phenyl-1-{3-[4-(3-acetylaminophenyl)piperidin-1-yl]propyl}-6-methoxy-1H-benzimidazole;
28) 2-(4-chlorophenyl)-1-{3-[4-(3-acetylaminophenyl)piperidin-1-yl]propyl}-6-methoxy-1H-benzimidazole;
29) 2-phenyl-1-{3-[4-(3-acetylaminophenyl)piperidin-1-yl]propyl}-6-chloro-1H-benzimidazole;
30) 2-(4-fluorophenyl)-1-{3-[4-(3-acetylaminophenyl)-piperidin-1-yl]propyl}-6-chloro-1H-benzimidazole;
31) 2-(4-chlorophenyl)-1-{3-[4-(3-acetylaminophenyl)piperidin-1-yl]propyl}-6-fluoro-1H-benzimidazole;
32) 2-phenyl-1-{3-[4-(3-acetylaminophenyl)piperidin-1-yl]propyl}-6-nitro-1H-benzimidazole;
33) 2-(2-fluorophenyl)-1-{3-[4-(3-acetylaminophenyl)piperidin-1-yl]propyl}-6-chloro-1H-benzimidazole;
34) 2-(3-fluorophenyl)-1-{3-[4-(3-acetylaminophenyl)piperidin-1-yl]propyl}-6-chloro-1H-benzimidazole;
35) 2-(3-chlorophenyl)-1-{3-[4-(3-acetylaminophenyl)piperidin-1-yl]propyl}-6-chloro-1H-benzimidazole;
36) 2-(4-chlorophenyl)-1-{3-[4-(3-acetylaminophenyl)piperidin-1-yl]propyl}-6-bromo-1H-benzimidazole;
37) 2-(2-chlorophenyl)-1-{3-[4-(3-acetylaminophenyl)piperidin-1-yl]propyl}-5,6-dimethyl-1H-benzimidazole;
38) 2-(3-chlorophenyl)-1-{3-[4-(3-acetylaminophenyl)piperidin-1-yl]propyl}-5,6-dimethyl-1H-benzimidazole;
39) 2-(4-chlorophenyl)-1-{3-[4-(3-acetylaminophenyl)piperidin-1-yl]propyl}-4,5-dimethyl-1H-benzimidazole;
40) 2-(2-chlorophenyl)-1-{3-[4-(3-acetylaminophenyl)piperidin-1-yl]propyl}-6-nitro-1H-benzimidazole;
41) 2-(3-chlorophenyl)-1-{3-[4-(3-acetylaminophenyl)piperidin-1-yl]propyl}-6-nitro-1H-benzimidazole;
42) 2-(4-chlorophenyl)-1-{3-[4-(3-acetylaminophenyl)piperidin-1-yl]propyl}-6-nitro-1H-benzimidazole;
43) 2-phenyl-1-{3-[4-(3-acetylaminophenyl)piperidin-1-yl]propyl}-6-bromo-1H-benzimidazole;
44) 2-(2,3,4,5-tetrafluorophenyl)-1-{3-[4-(3-acetylaminophenyl)piperidin-1-yl]propyl}-1H-benzimidazole;
45) 2-(4-trifluoromethylphenyl)-1-{3-[4-(3-acetylaminophenyl)piperidin-1-yl]propyl}-1H-benzimidazole;
46) 2-(4-biphenyl)-1-{3-[4-(3-acetylaminophenyl)piperidin-1-yl]propyl}-1H-benzimidazole;
47) 2-(4-phenoxyphenyl)-1-{3-[4-(3-acetylaminophenyl)piperidin-1-yl]propyl}-1H-benzimidazole;
48) 2-(4-fluorophenyl)-1-{3-[4-(3-acetylaminophenyl)piperidin-1-yl]propyl}-1H-benzimidazole;
49) 2-(4-chlorophenyl)-1-{3-[4-(3-acetylaminophenyl)piperidin-1-yl]propyl}-5,7-dimethyl-1H-benzimidazole;
50) 2-(3,4-difluorophenyl)-1-{3-[4-(3-acetylaminophenyl)piperidin-1-yl]propyl}-1H-benzimidazole;
51) 2-(4-cyanophenyl)-1-{3-[4-(3-acetylaminophenyl)piperidin-1-yl]propyl}-1H-benzimidazole;
52) 2-(3-cyanophenyl)-1-{3-[4-(3-acetylaminophenyl)piperidin-1-yl]propyl}-1H-benzimidazole;
53) 2-(4-chloro-2-fluorophenyl)-1-{3-[4-(3-acetylaminophenyl)piperidin-1-yl]propyl}-1H-benzimidazole;
54) 2-(2-chloro-4-fluorophenyl)-1-{3-[4-(3-acetylaminophenyl)piperidin-1-yl]propyl}-1H-benzimidazole;
55) 2-(3-nitrophenyl)-1-{3-[4-(3-acetylaminophenyl)piperidin-1-yl]propyl}-1H-benzimidazole;
56) 2-(5-chloro-2-methoxyphenyl)-1-{3-[4-(3-acetylaminophenyl)piperidin-1-yl]propyl}-1H-benzimidazole;
57) 2-(2-chloro-4-nitrophenyl)-1-{2-[4-(3-acetamidophenyl)piperidin-1-yl]propyl}-1H-benzimidazole;
58) 2-(2,4-dimethoxyphenyl)-1-{3-[4-(3-acetylaminophenyl)piperidin-1-yl]propyl}-1H-benzimidazole;
59) 2-(4-chloro-2-fluorophenyl)-1-{3-[4-(3-acetylaminophenyl)piperidin-1-yl]propyl}-5,6-dimethyl-1H-benzimidazole;
60) 2-(4-chlorophenyl)-1-{3-[4-(3-acetylaminophenyl)piperidin-1-yl]propyl}-5-carbamoyl-1H-benzimidazole;
61) 2-(4-chlorophenyl)-1-{3-[4-(3-acetylaminophenyl)piperidin-1-yl]propyl}-6-carbamoyl-1H-benzimidazole;
62) 2-(3-carbamoylphenyl)-1-{3-[4-(3-acetylaminophenyl)piperidin-1-yl]propyl}-1H-benzimidazole;
63) 2-(2-hydroxyphenyl)-1-{3-[4-(3-acetylaminophenyl)piperidin-1-yl]propyl}-1H-benzimidazole;
64) 2-(4-chlorophenyl)-1-{3-[4-(3-isobutyrylaminophenyl)piperidin-1-yl]propyl}-1H-benzimidazole;
65) 2-(4-chlorophenyl)-1-{3-[4-(3-benzoylaminophenyl)piperidin-1-yl]propyl}-1H-benzimidazole;
66) 2-(4-chlorophenyl)-1-{3-[4-(3-(3-chlorobenzoylamino)phenyl)piperidin-1-yl]propyl}-1H-benzimidazole;
67) 2-(4-chlorophenyl)-1-{3-[4-(3-(4-methylbenzoylamino)phenyl)piperidin-1-yl]propyl}-1H-benzimidazole;
68) 6-bromo-5-methyl-2-phenyl-3-{3-[4-(3-acetylaminophenyl)piperidin-1-yl]propyl}-3H-imidazo[4,5-b]pyridine;
69) 5-methyl-2-phenyl-3-{3-[4-(3-acetylaminophenyl)piperidin-1-yl]propyl}-3H-imidazo[4,5-b]pyridine;
70) 2-(benzo[1,3]dioxol-5-yl)-1-{3-[4-(3-acetylaminophenyl)piperidin-1-yl]propyl}-1H-benzimidazole;
71) 2-(4-chlorophenyl)-1-{2-[4-(3-isobutyrylaminophenyl)piperidin-1-yl]ethyl}-1H-benzimidazole;
72) 2-phenyl-3-{3-[4-(3-acetylaminophenyl)piperidin-1-yl]propyl}-3H-imidazo[4,5-c]pyridine;

73) 2-phenyl-3-{3-[4-(3-acetylaminophenyl)piperidin-1-yl]propyl}-3H-imidazo[4,5-d]pyridine;
74) 5-bromo-6-methyl-2-phenyl-3-{3-[4-(3-acetylaminophenyl)piperidin-1-yl]propyl}-3H-imidazo[4,5-e]pyridine;
75) 6-methyl-2-phenyl-3-{3-[4-(3-acetylaminophenyl)piperidin-1-yl]propyl}-3H-imidazo[4,5-e]pyridine;
76) 2-(3-methoxycarbonylphenyl)-1-{3-[4-(3-acetylaminophenyl)piperidin-1-yl]propyl}-1H-benzimidazole;
77) 2-(4-ethylphenyl)-1-{3-[4-(3-acetylaminophenyl)piperidin-1-yl]propyl}-1H-benzimidazole;
78) 2-(4-cyanophenyl)-1-{3-[4-(3-acetylaminophenyl)piperidin-1-yl]propyl}-5,6-dimethyl-1H-benzimidazole;
79) 2-(m-tolyl)-1-{3-[4-(3-acetylaminophenyl)piperidin-1-yl]propyl}-1H-benzimidazole;
80) 2-(2-chloro-4-fluorophenyl)-1-{3-[4-(3-acetylaminophenyl)piperidin-1-yl]propyl}-5,6-dimethyl-1H-benzimidazole;
81) 2-(4-chlorophenyl)-1-{3-[4-(3-acetylaminophenyl)piperidin-1-yl]propyl}-5-cyano-1H-benzimidazole;
82) 2-(4-chlorophenyl)-1-{3-[4-(3-acetylaminophenyl)piperidin-1-yl]propyl}-6-cyano-1H-benzimidazole;
83) 2-(4-chlorophenyl)-1-{3-[4-(3-acetylaminophenyl)piperidin-1-yl]propyl}-5-fluoro-1H-benzimidazole;
84) 2-(4-fluorophenyl)-1-{3-[4-(3-acetylaminophenyl)piperidin-1-yl]propyl}-5-chloro-1H-benzimidazole;
85) 2-(4-chlorophenyl)-1-{3-[4-(3-acetylaminophenyl)piperidin-1-yl]propyl}-5-nitro-1H-benzimidazole;
86) 2-(4-chloro-2-methoxyphenyl)-1-{3-[4-(3-acetylaminophenyl)piperidin-1-yl]propyl}-5,6-dimethyl-1H-benzimidazole;
87) 2-(5-chloro-2-methoxyphenyl)-1-{3-[4-(3-acetylaminophenyl)piperidin-1-yl]propyl}-5,6-dimethyl-1H-benzimidazole;
88) 2-methyl-1-{3-[4-(3-acetylaminophenyl)piperidin-1-yl]propyl}-1H-benzimidazole;
89) 2-methyl-1-{3-[4-(3-acetylaminophenyl)piperidin-1-yl]propyl}-5,6-dimethyl-1H-benzimidazole;
90) 2-methyl-1-{3-[4-(3-isobutyrylaminophenyl)piperidin-1-yl]propyl}-1H-benzimidazole;
91) 2,5-dimethyl-3-{3-[4-(3-acetylaminophenyl)piperidin-1-yl]propyl}-3H-imidazo[4,5-b]pyridine;
92) 6-bromo-2,5-dimethyl-3-{3-[4-(3-acetylaminophenyl)piperidin-1-yl]propyl}-3H-imidazo[4,5-b]pyridine;
93) 6-bromo-2-ethyl-5-methyl-3-{3-[4-(3-acetylaminophenyl)piperidin-1-yl]propyl}-3H-imidazo[4,5-b]pyridine;
94) 6-bromo-2-butyl-5-methyl-3-{3-[4-(3-acetylaminophenyl)piperidin-1-yl]propyl}-3H-imidazo[4,5-b]pyridine;
95) 2-butyl-5,7-dimethyl-3-{3-[4-(3-acetylaminophenyl)piperidin-1-yl]propyl}-3H-imidazo[4,5-b]pyridine;
96) 2-butyl-5,7-dimethyl-6-phenyl-3-{3-[4-(3-acetylaminophenyl)piperidin-1-yl]propyl}-3H-imidazo[4,5-b]pyridine;
97) 2-butyl-5-methyl-6-pyridin-2-yl-3-{3-[4-(3-acetylaminophenyl)piperidin-1-yl]propyl}-3H-imidazo[4,5-b]pyridine;
98) 6-bromo-2-butyl-5-methyl-3-{3-[4-(3-isobutyrylaminophenyl)piperidin-1-yl]propyl}-3H-imidazo[4,5-b]pyridine;
99) 2-butyl-5,7-dimethyl-3-{3-[4-(3-isobutyrylaminophenyl)piperidin-1-yl]propyl}-3H-imidazo[4,5-b]pyridine;
100) 2-butyl-5,7-dimethyl-6-phenyl-3-{3-[4-(3-isobutyrylaminophenyl)piperidin-1-yl]propyl}-3H-imidazo[4,5-b]pyridine;
101) 2-butyl-5-methyl-6-pyridin-2-yl-3-{3-[4-(3-isobutyrylaminophenyl)piperidin-1-yl]propyl}-3H-imidazo[4,5-b]pyridine;
102) 2-butyl-5-formyl-6-phenyl-3-{3-[4-(3-isobutyrylaminophenyl)piperidin-1-yl]propyl}-3H-imidazo[4,5-b]pyridine;
103) 2-butyl-5-methyl-6-(4-nitrophenyl)-3-{3-[4-(3-isobutyrylaminophenyl)piperidin-1-yl]propyl}-3H-imidazo[4,5-b]pyridine;
104) 2-(pyridin-2-yl)-1-{3-[4-(3-acetamidophenyl)piperidin-1-yl]propyl}-1H-benzimidazole;
105) 2-(pyridin-3-yl)-1-{3-[4-(3-acetamidophenyl)piperidin-1-yl]propyl}-1H-benzimidazole;
106) 2-(pyridin-4-yl)-1-{3-[4-(3-acetylaminophenyl)piperidin-1-yl]propyl}-1H-benzimidazole;
107) 2-(furan-3-yl)-1-{3-[4-(3-acetylaminophenyl)piperidin-1-yl]propyl}-1H-benzimidazole;
108) 2-(5-bromofuran-2-yl)-1-{3-[4-(3-acetylaminophenyl)piperidin-1-yl]propyl}-1H-benzimidazole;
109) 2-(thiophen-2-yl)-1-{3-[4-(3-acetylaminophenyl)piperidin-1-yl]propyl}-1H-benzimidazole;
110) 2-(5-methylthiophen-2-yl)-1-{3-[4-(3-acetylaminophenyl)piperidin-1-yl]propyl}-1H-benzimidazole;
111) 2-(1-methyl-1H-pyrrol-2-yl)-1-{3-[4-(3-acetylaminophenyl)piperidin-1-yl]propyl}-1H-benzimidazole;
112) 2-(5-bromopyridin-3-yl)-1-{3-[4-(3-acetylaminophenyl)piperidin-1-yl]propyl}-1H-benzimidazole;
113) 2-(6-chloropyridin-3-yl)-1-{3-[4-(3-acetamidophenyl)piperidin-1-yl]propyl}-1H-benzimidazole;
114) 2-(6-methylpyridin-3-yl)-1-{3-[4-(3-acetamidophenyl)piperidin-1-yl]propyl}-1H-benzimidazole;
115) 2-(2-methoxypyridin-3-yl)-1-{3-[4-(3-acetamidophenyl)piperidin-1-yl]propyl}-1H-benzimidazole;
116) 5-chloro-2-(pyridin-3-yl)-1-{3-[4-(3-acetamidophenyl)piperidin-1-yl]propyl}-1H-benzimidazole;
117) 5-nitro-2-(pyridin-3-yl)-1-{3-[4-(3-acetamidophenyl)piperidin-1-yl]propyl}-1H-benzimidazole;
118) 5-chloro-2-(5-bromofuran-2-yl)-1-{3-[4-(3-acetamidophenyl)piperidin-1-yl]propyl}-1H-benzimidazole;
119) 2-(furan-2-yl)-5-methoxy-1-{3-[4-(3-acetamidophenyl)piperidin-1-yl]propyl}-1H-benzimidazole;
120) 5-methyl-2-(thiophen-3-yl)-1-{3-[4-(3-acetamidophenyl)piperidin-1-yl]propyl}-1H-benzimidazole;
121) 5,6-dimethyl-2-(1-methylpyrrol-2-yl)-1-{3-[4-(3-acetamidophenyl)piperidin-1-yl]propyl}-1H-benzimidazole;
122) 2-(thiazol-4-yl)-1-{3-[4-(3-acetamidophenyl)piperidin-1-yl]propyl}-1H-benzimidazole;
123) 2-(4-methyloxazol-5-yl)-1-{3-[4-(3-acetamidophenyl)piperidin-1-yl]propyl}-1H-benzimidazole;
124) 2-(1-methyl-1H-imidazol-5-yl)-1-{3-[4-(3-acetamidophenyl)piperidin-1-yl]propyl}-1H-benzimidazole;
125) 2-(pyridin-2-ylmethyl)-1-{3-[4-(3-acetamidophenyl)piperidin-1-yl]propyl}-1H-benzimidazole;
126) 2-(pyridin-3-ylmethyl)-1-{3-[4-(3-acetamidophenyl)piperidin-1-yl]propyl}-1H-benzimidazole; and
127) 2-[2-(pyridin-3-yl)ethyl]-1-{3-[4-(3-acetamidophenyl)piperidin-1-yl]propyl}-1H-benzimidazole.

TABLE 1

| Compound | Structure |
|---|---|
| 1 | *[structure: 2-phenyl-benzimidazole linked via ethyl to piperidine-N, piperidine-4-yl attached to 3-acetamidophenyl]* |
| 2 | *[structure: 2-(4-chlorophenyl)-benzimidazole linked via ethyl to piperidine-N, piperidine-4-yl attached to 3-acetamidophenyl]* |
| 3 | *[structure: 2-phenyl-benzimidazole linked via propyl to piperidine-N, piperidine-4-yl attached to 3-acetamidophenyl]* |
| 4 | *[structure: 2-(4-chlorophenyl)-benzimidazole linked via propyl to piperidine-N, piperidine-4-yl attached to 3-acetamidophenyl]* |
| 5 | *[structure: 2-phenyl-benzimidazole linked via butyl to piperidine-N, piperidine-4-yl attached to 3-acetamidophenyl]* |

TABLE 1-continued
| Compound | Structure |
|---|---|
| 6 | 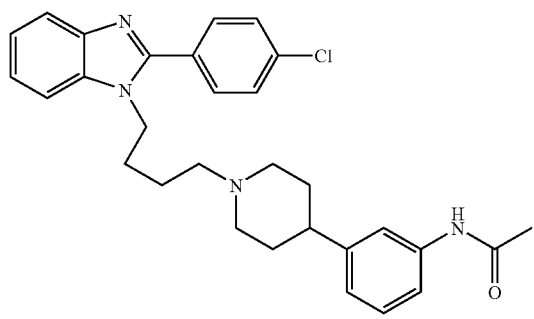 |
| 7 | 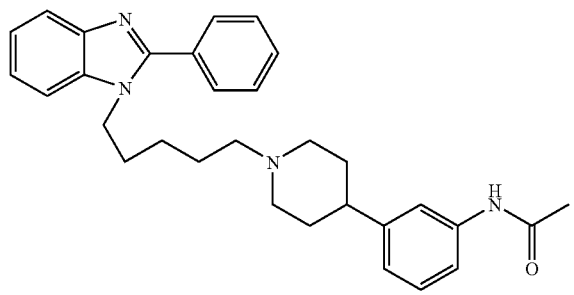 |
| 8 | 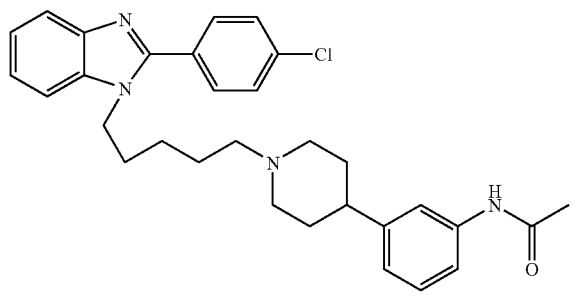 |
| 9 | 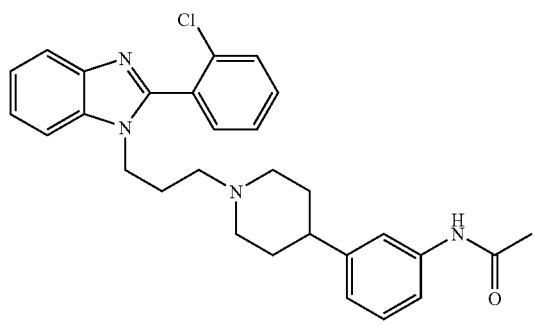 |
| 10 | 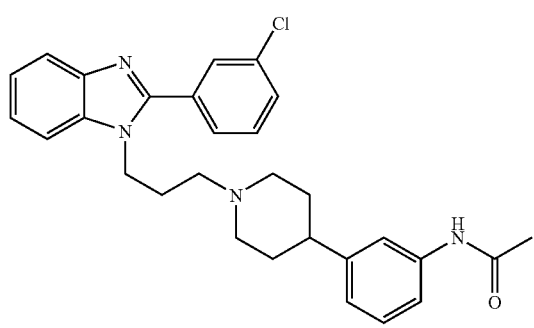 |

TABLE 1-continued

| Compound | Structure |
|---|---|
| 11 | 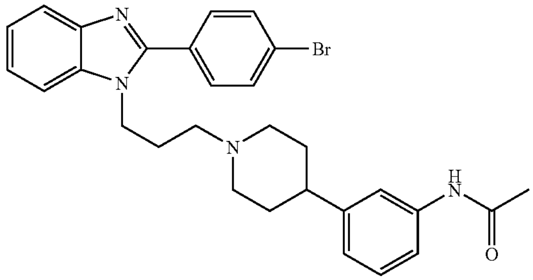 |
| 12 | 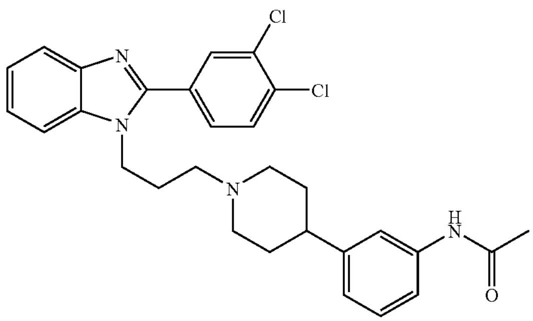 |
| 13 | 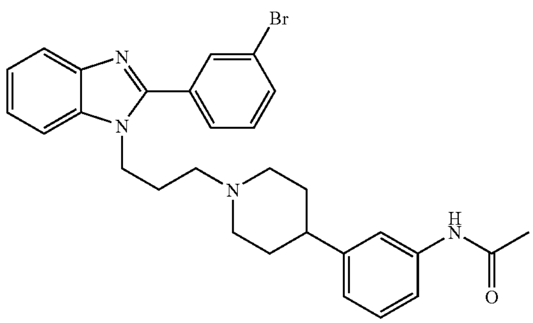 |
| 14 | 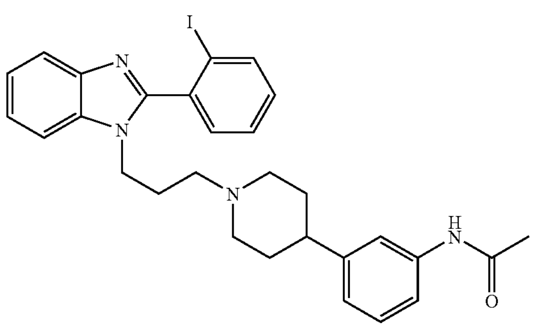 |
| 15 | 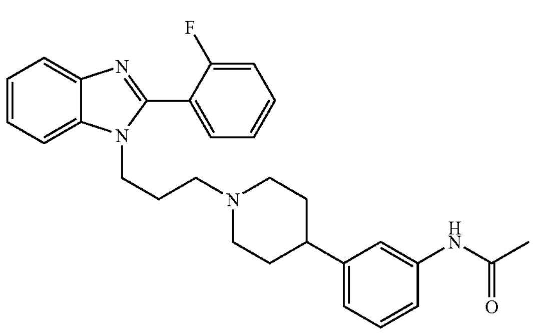 |

TABLE 1-continued
| Compound | Structure |
|---|---|
| 16 | 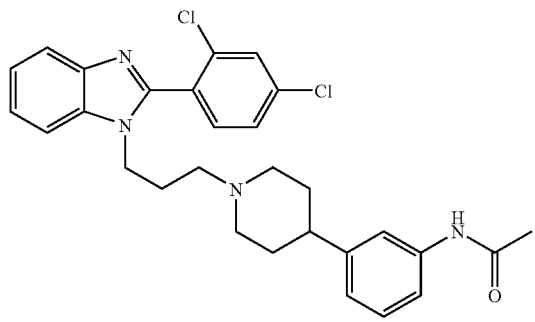 |
| 17 | 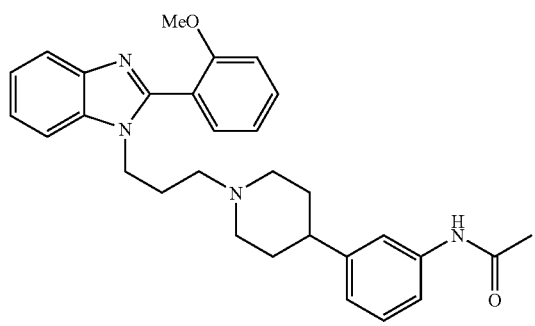 |
| 18 | 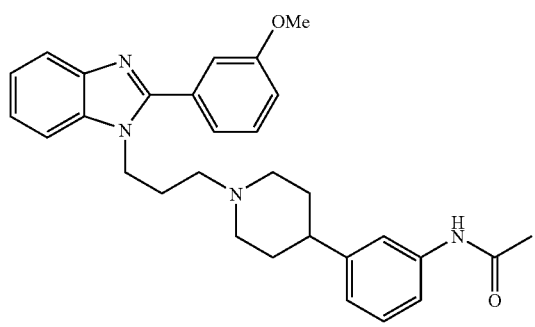 |
| 19 | 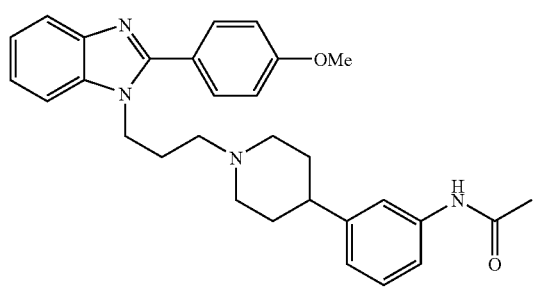 |
| 20 | 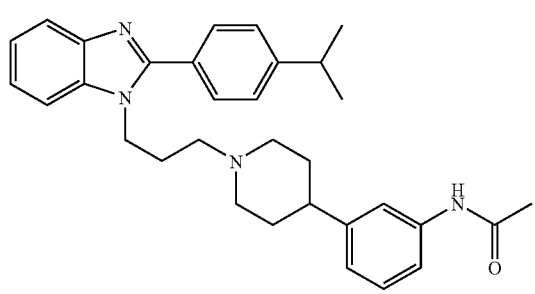 |

TABLE 1-continued
| Compound | Structure |
|---|---|
| 21 | 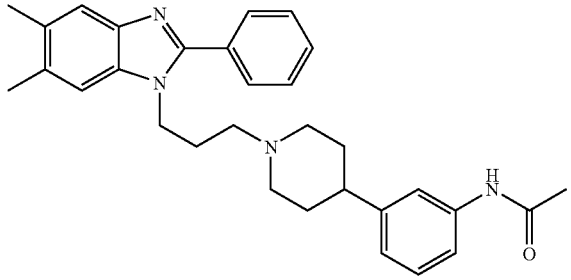 |
| 22 | 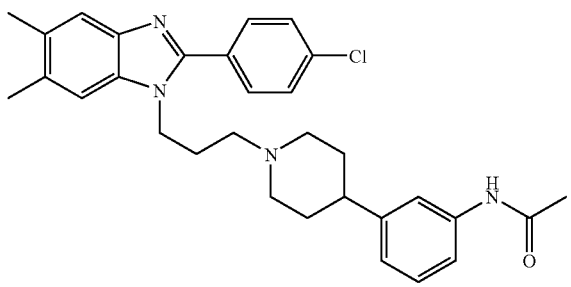 |
| 23 | 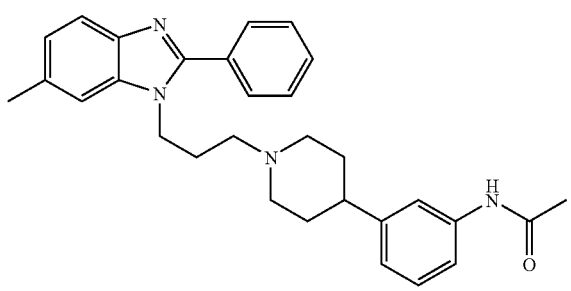 |
| 24 | 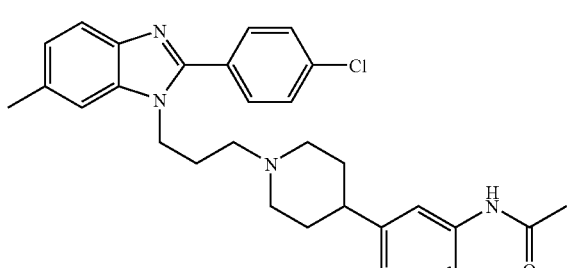 |
| 25 | 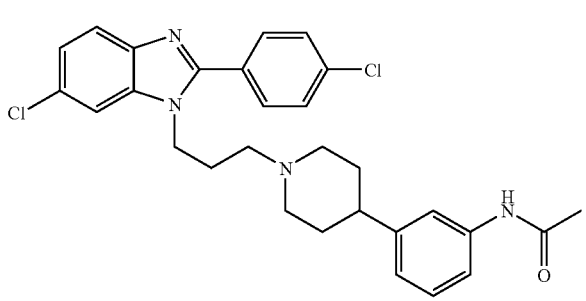 |

TABLE 1-continued

| Compound | Structure |
|---|---|
| 26 | 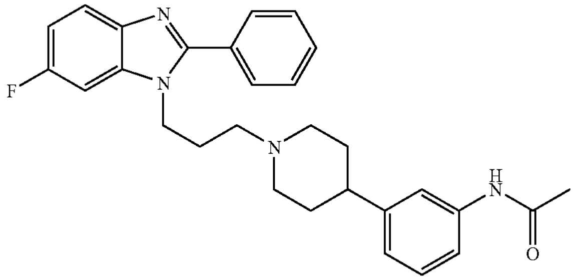 |
| 27 | 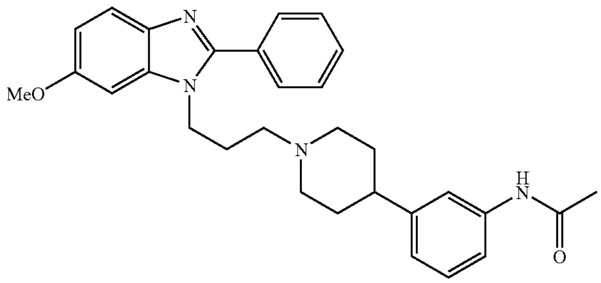 |
| 28 | 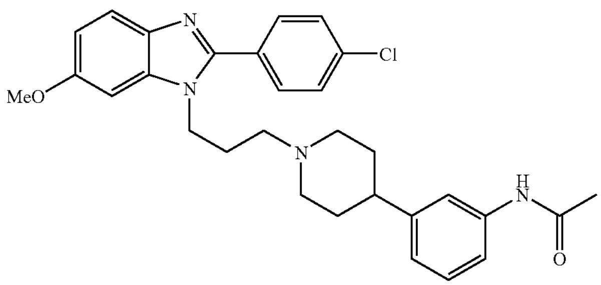 |
| 29 | 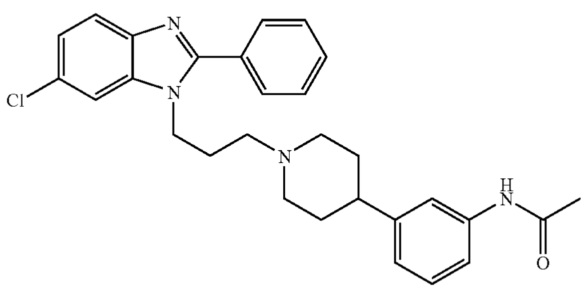 |
| 30 | 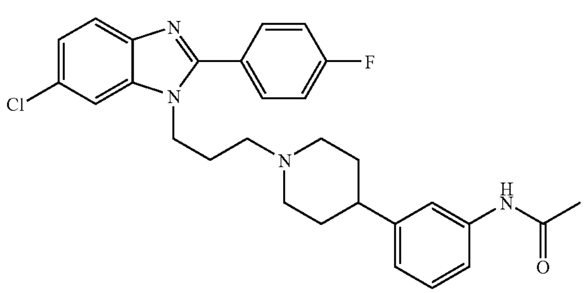 |

TABLE 1-continued
| Compound | Structure |
|---|---|
| 31 | 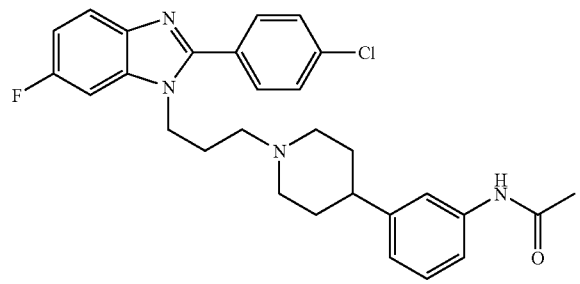 |
| 32 | 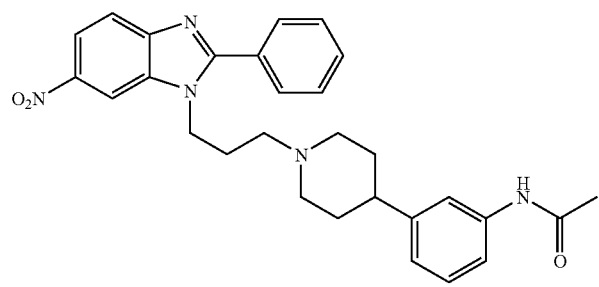 |
| 33 | 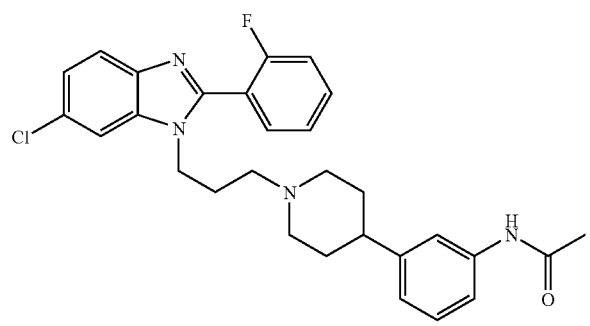 |
| 34 | 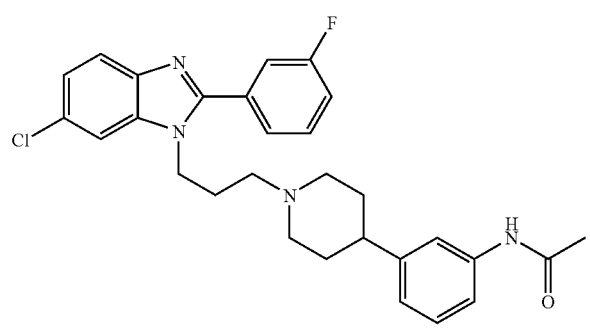 |
| 35 | 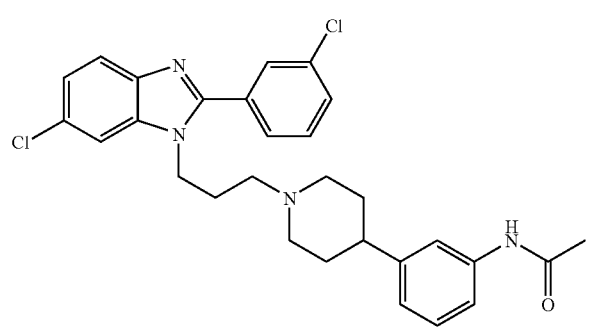 |

TABLE 1-continued

| Compound | Structure |
| --- | --- |
| 36 | 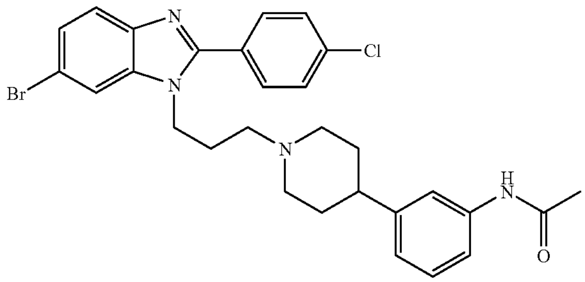 |
| 37 | 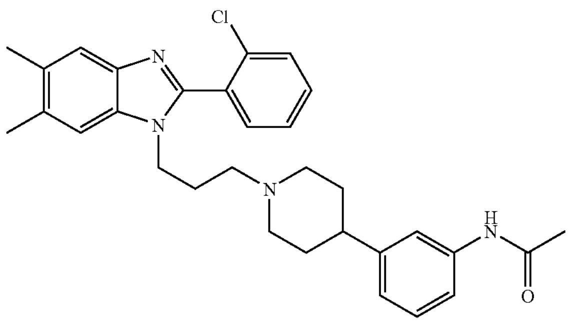 |
| 38 | 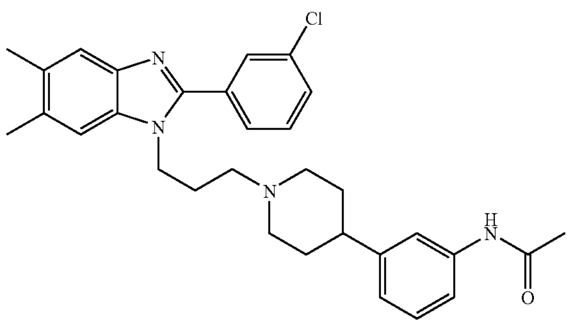 |
| 39 | 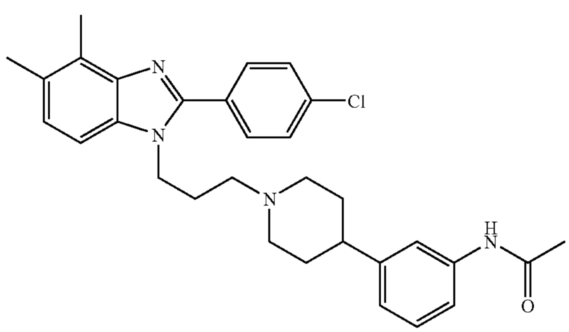 |
| 40 | 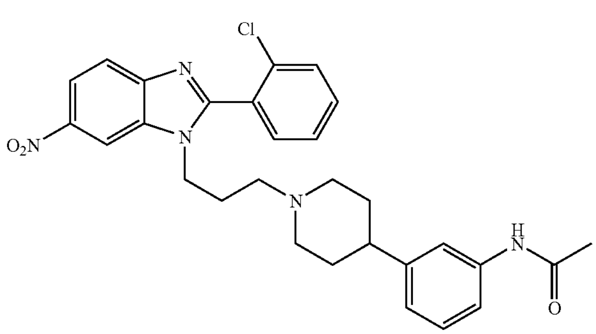 |

TABLE 1-continued
| Compound | Structure |
|---|---|
| 41 | 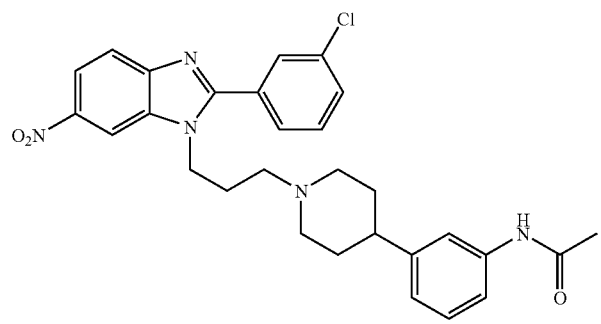 |
| 42 | 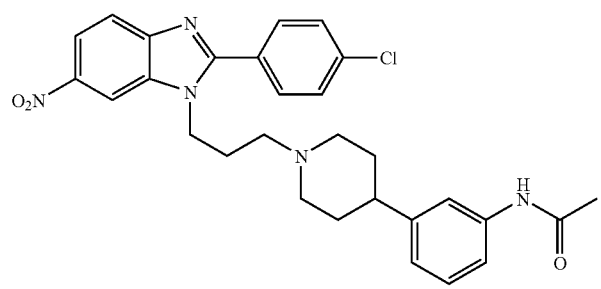 |
| 43 | 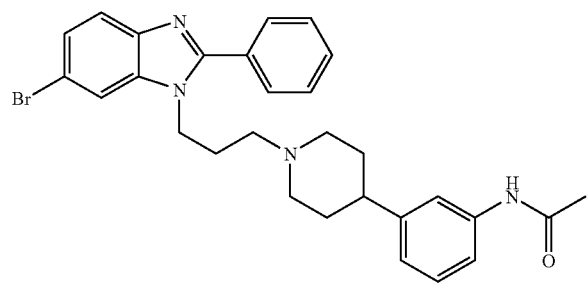 |
| 44 | 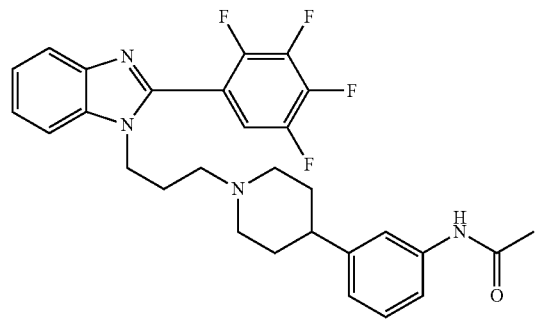 |
| 45 | 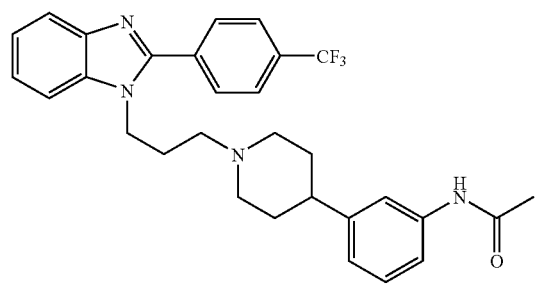 |

TABLE 1-continued
| Compound | Structure |
|---|---|
| 46 | 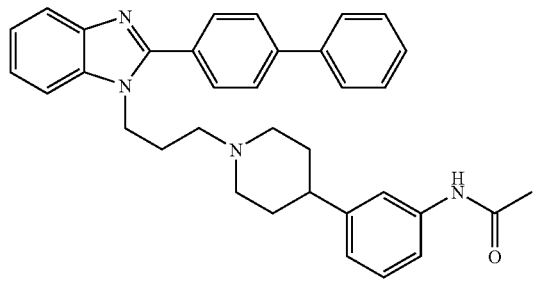 |
| 47 | 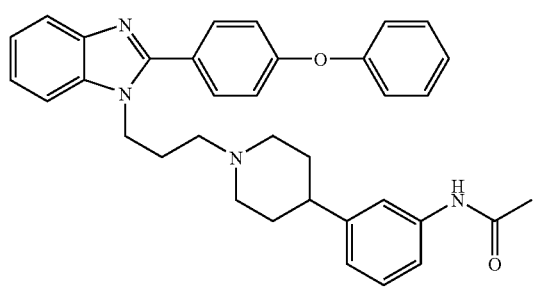 |
| 48 | 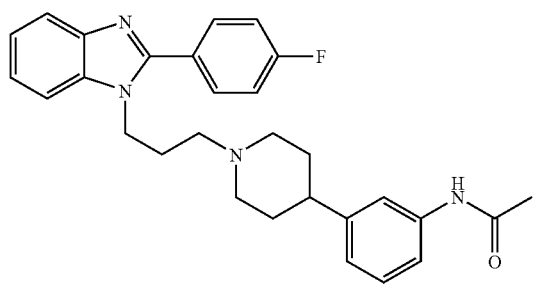 |
| 49 | 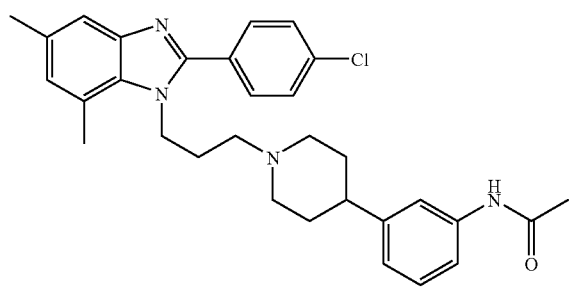 |
| 50 | 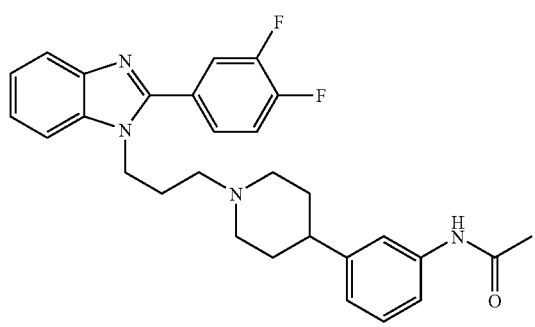 |

TABLE 1-continued
| Compound | Structure |
|---|---|
| 51 | 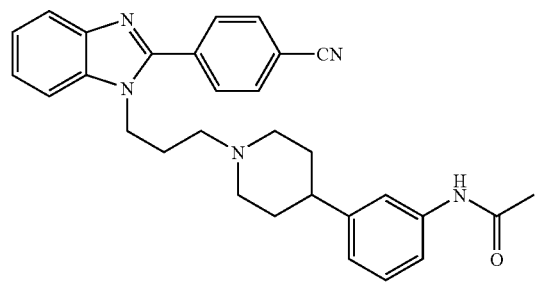 |
| 52 | 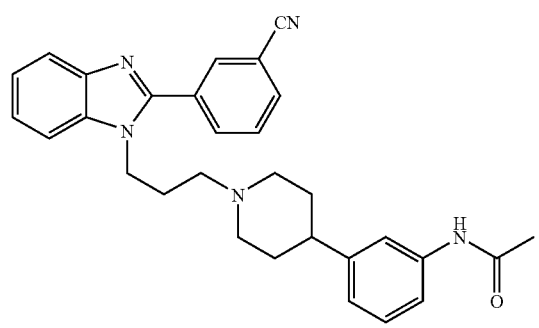 |
| 53 | 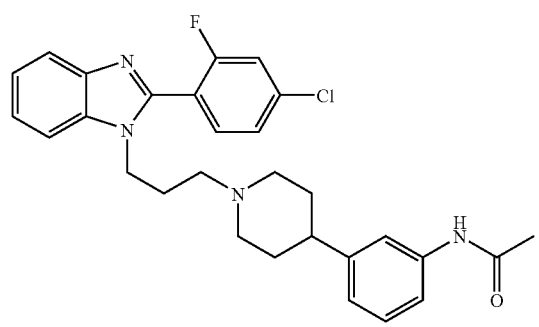 |
| 54 | 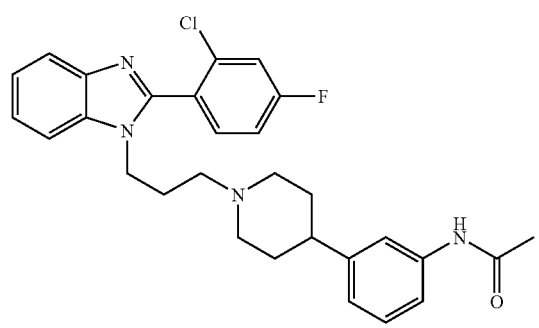 |
| 55 | 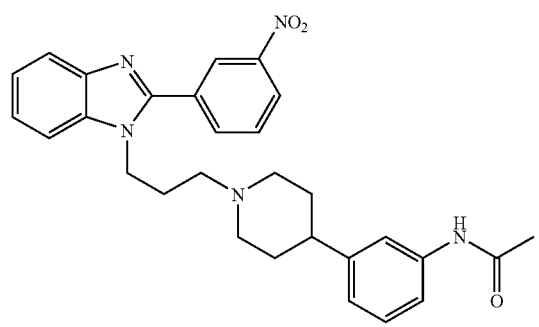 |

TABLE 1-continued
| Compound | Structure |
|---|---|
| 56 | 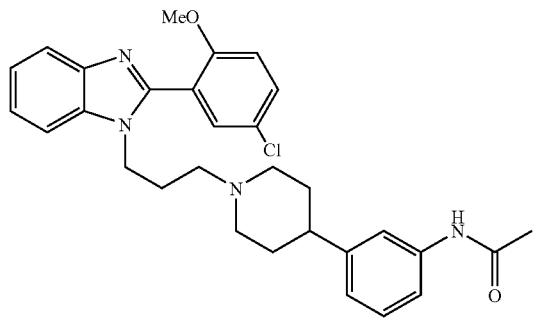 |
| 57 | 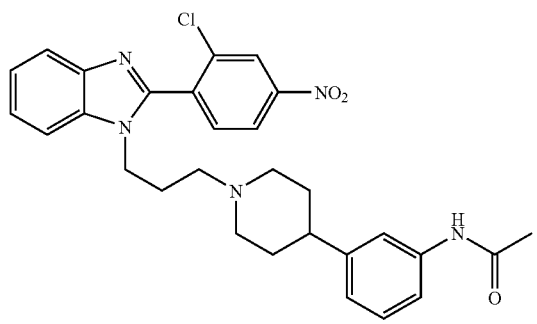 |
| 58 | 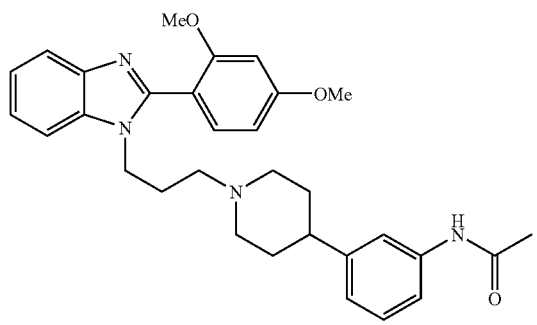 |
| 59 | 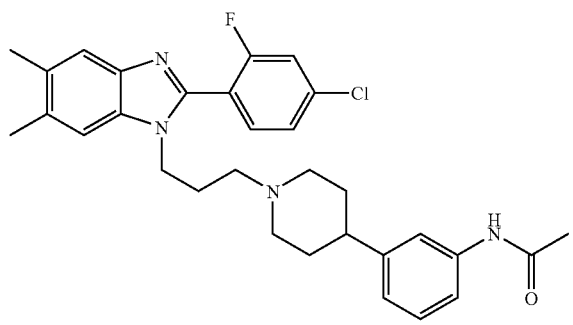 |

TABLE 1-continued
| Compound | Structure |
|---|---|
| 60 | 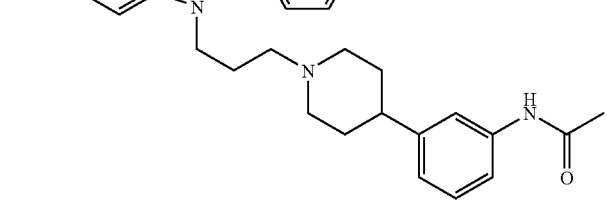 |
| 61 | 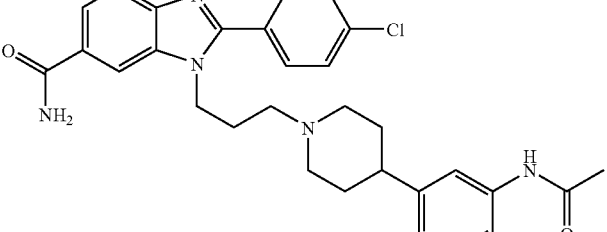 |
| 62 | 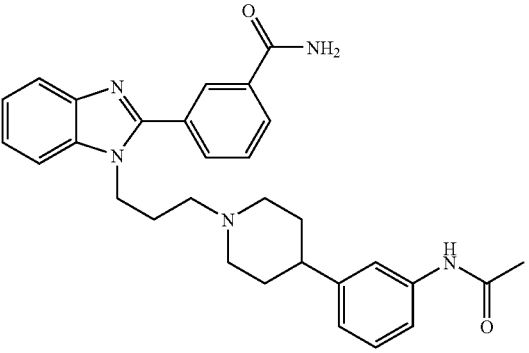 |
| 63 | 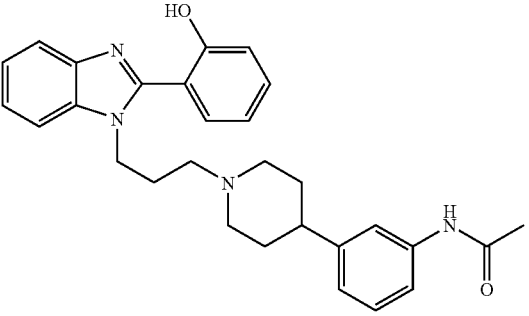 |
| 64 | 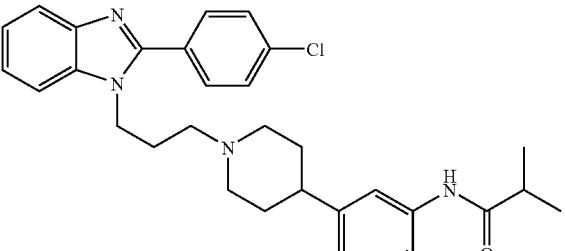 |

TABLE 1-continued

| Compound | Structure |
|---|---|
| 65 | 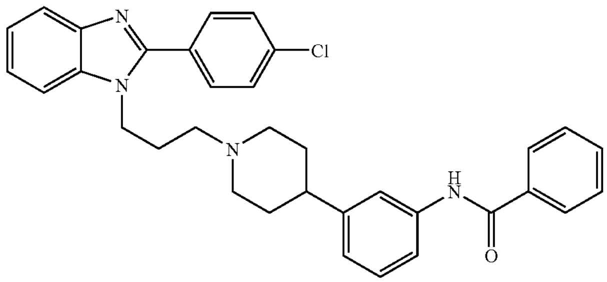 |
| 66 | 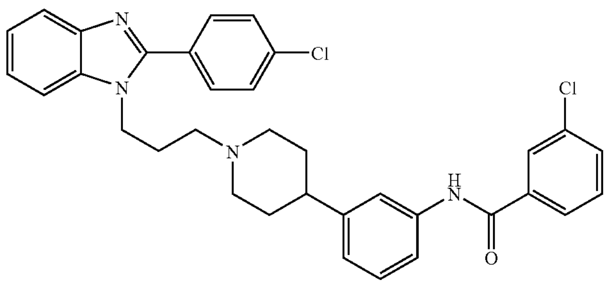 |
| 67 | 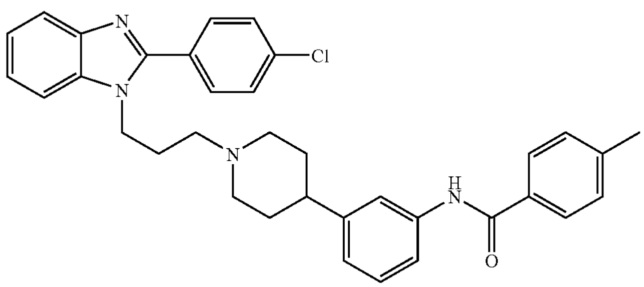 |
| 68 | 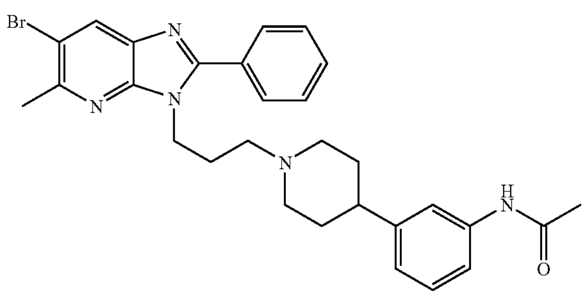 |
| 69 | 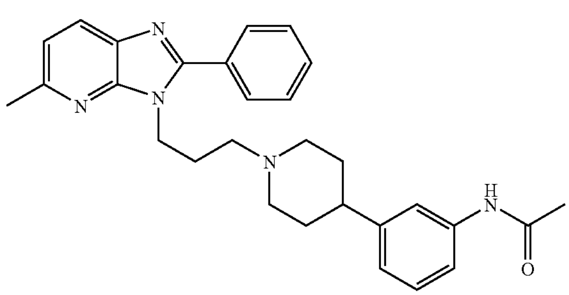 |

TABLE 1-continued

| Compound | Structure |
|---|---|
| 70 | 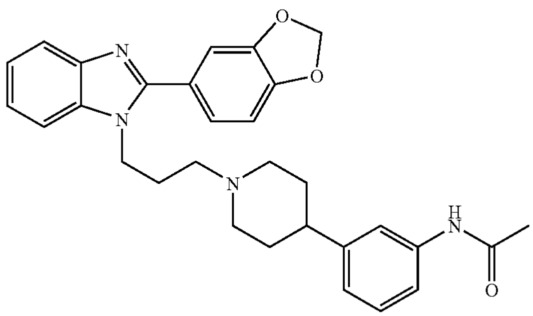 |
| 71 | 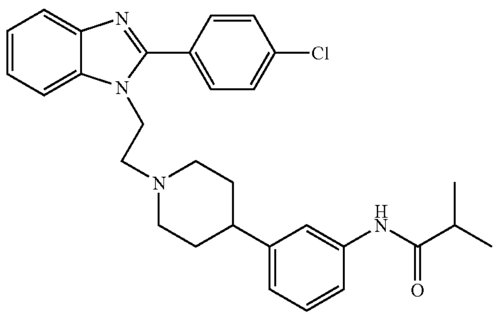 |
| 72 | 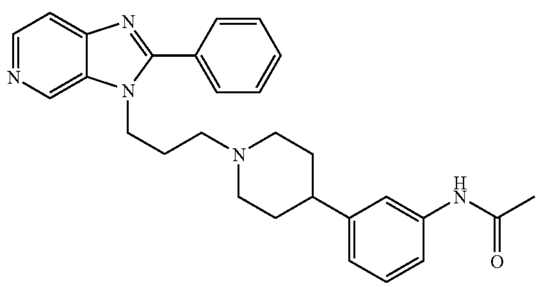 |
| 73 | 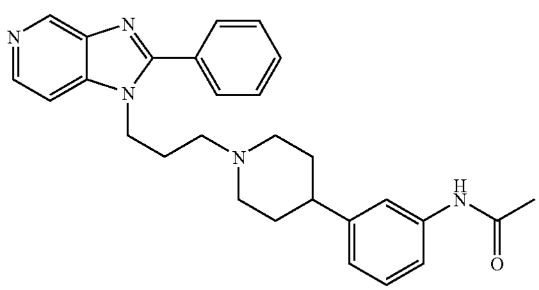 |
| 74 | 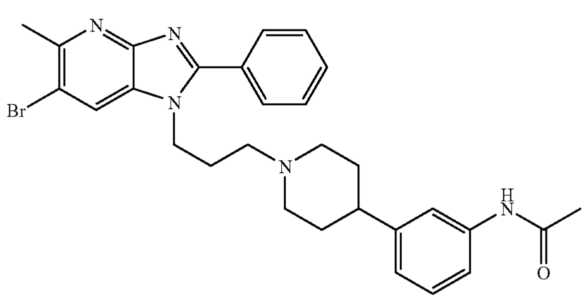 |

TABLE 1-continued
| Compound | Structure |
|---|---|
| 75 | 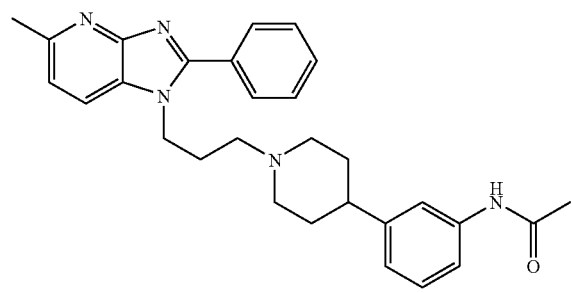 |
| 76 | 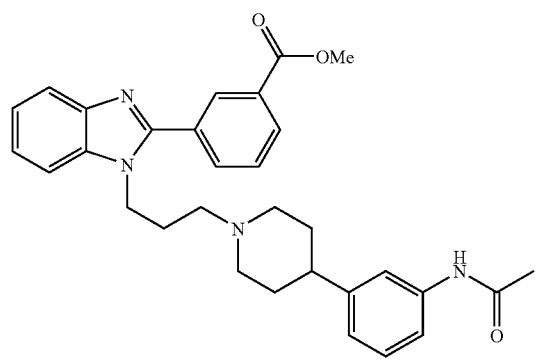 |
| 77 | 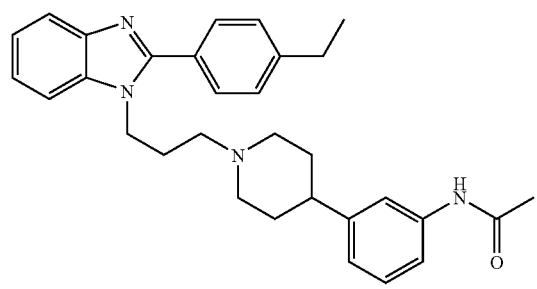 |
| 78 | 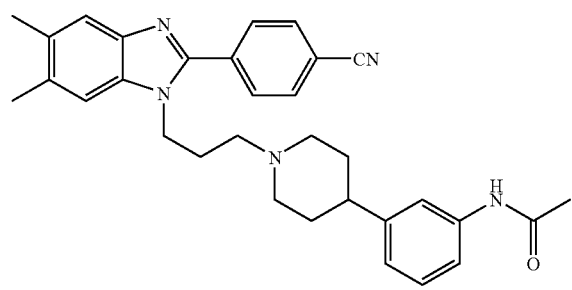 |
| 79 | 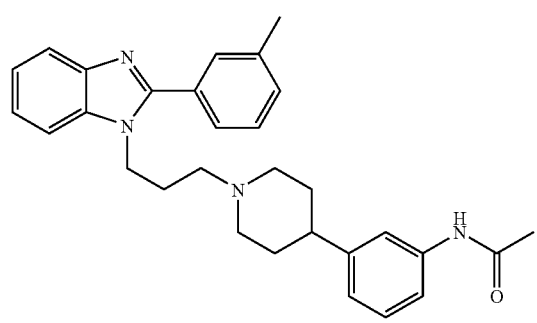 |

TABLE 1-continued
| Compound | Structure |
|---|---|
| 80 | 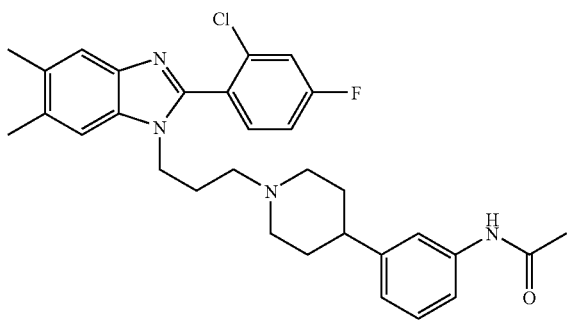 |
| 81 | 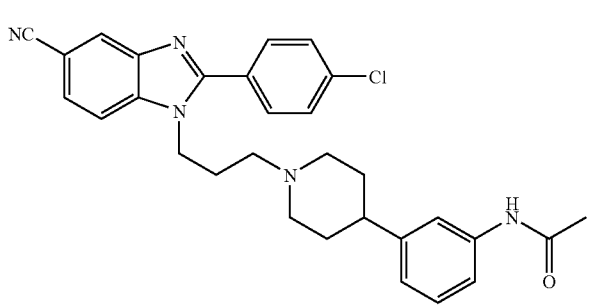 |
| 82 | 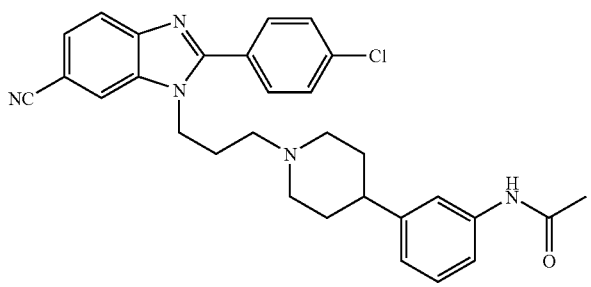 |
| 83 | 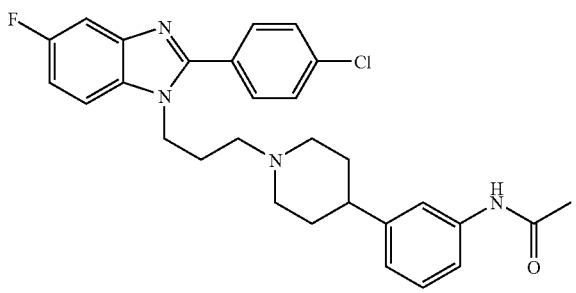 |
| 84 | 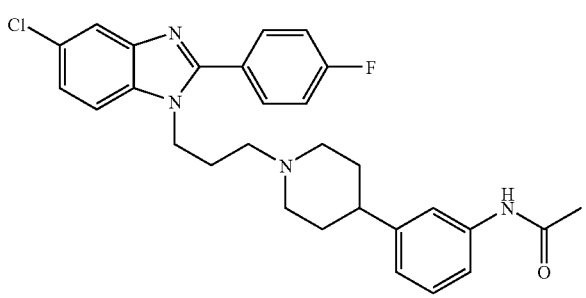 |

TABLE 1-continued

| Compound | Structure |
|---|---|
| 85 | (structure) |
| 86 | (structure) |
| 87 | (structure) |
| 88 | (structure) |
| 89 | (structure) |

TABLE 1-continued
| Compound | Structure |
|---|---|
| 90 | 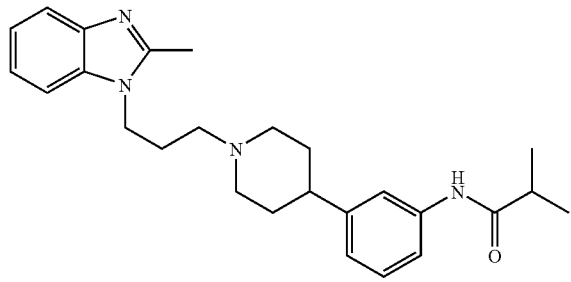 |
| 91 | 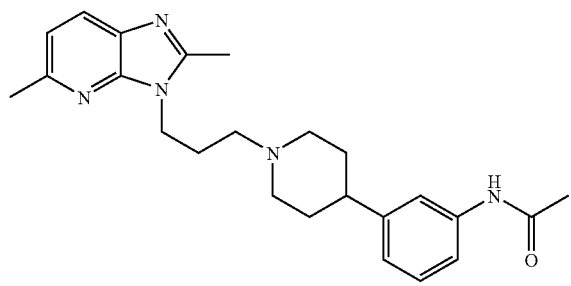 |
| 92 | 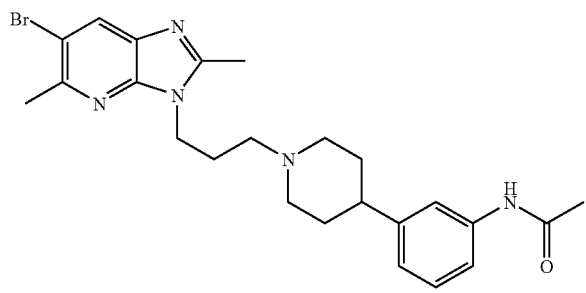 |
| 93 | 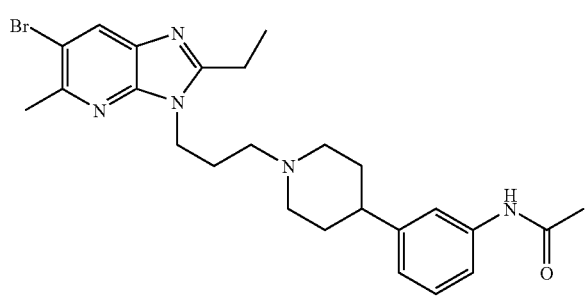 |
| 94 | 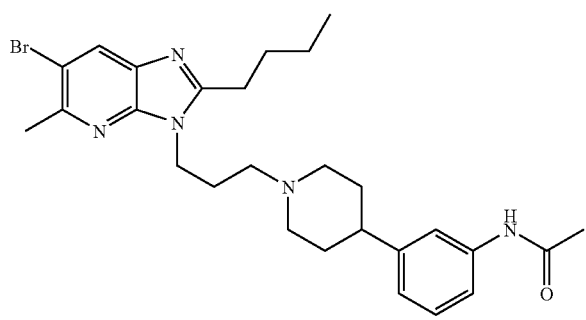 |

TABLE 1-continued
| Compound | Structure |
|---|---|
| 95 | 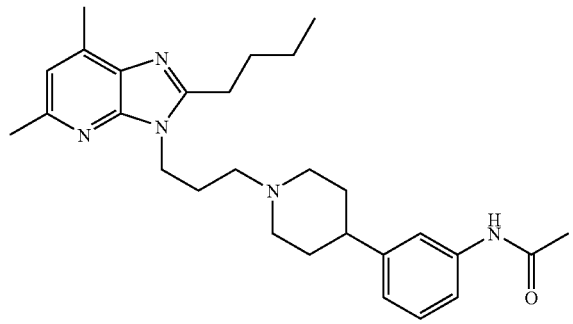 |
| 96 | 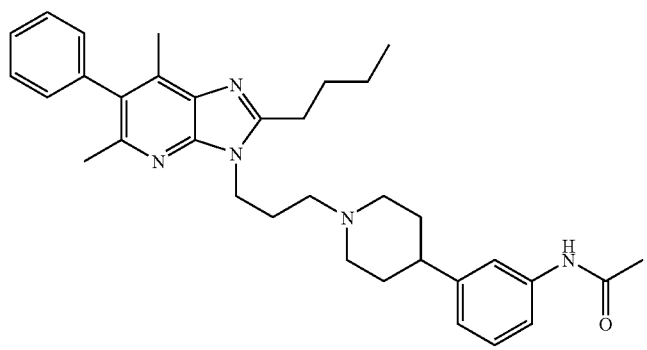 |
| 97 | 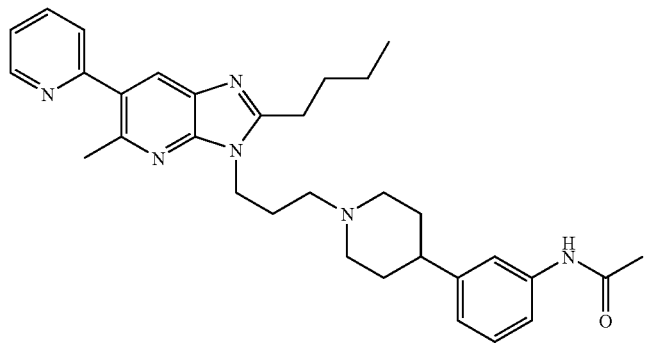 |
| 98 | 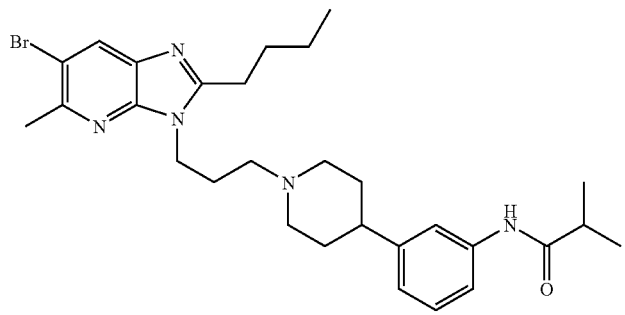 |

TABLE 1-continued
| Compound | Structure |
|---|---|
| 99 | 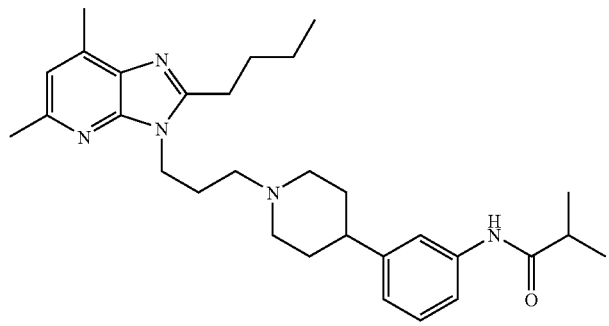 |
| 100 | 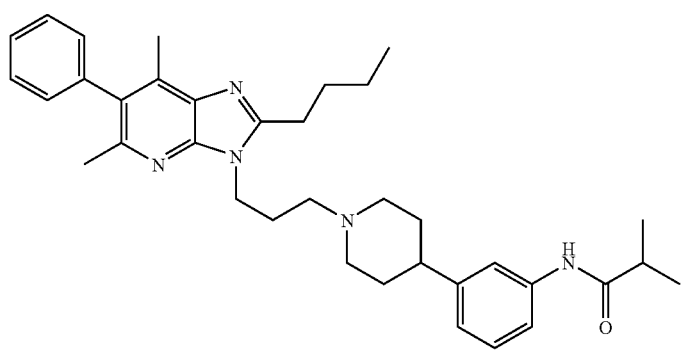 |
| 101 | 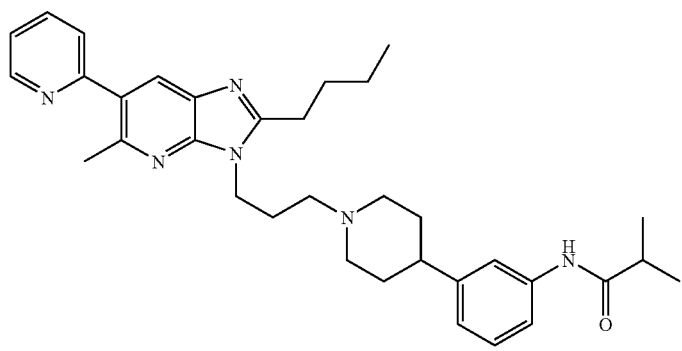 |
| 102 | 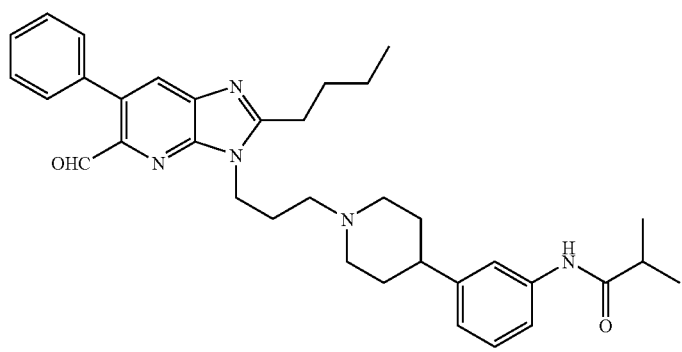 |

TABLE 1-continued
| Compound | Structure |
|---|---|
| 103 | 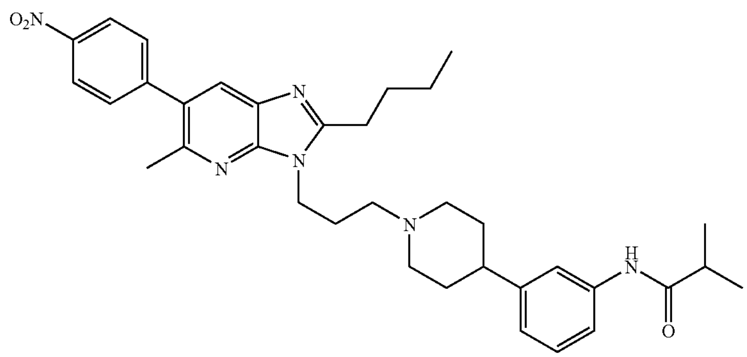 |
| 104 | 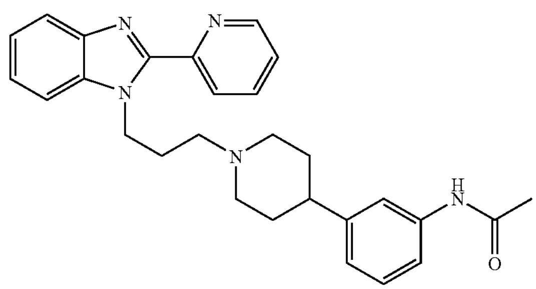 |
| 105 | 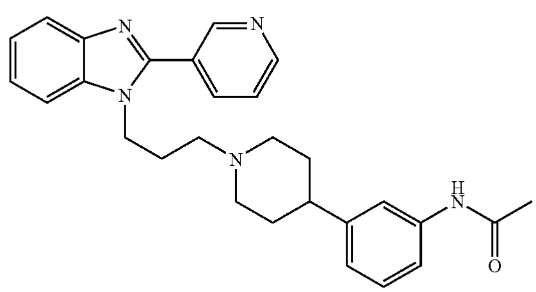 |
| 106 | 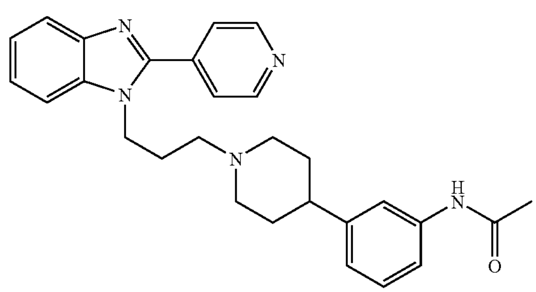 |
| 107 | 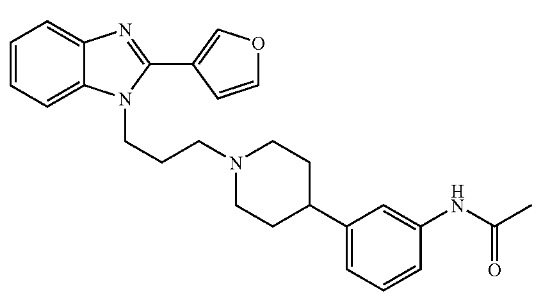 |
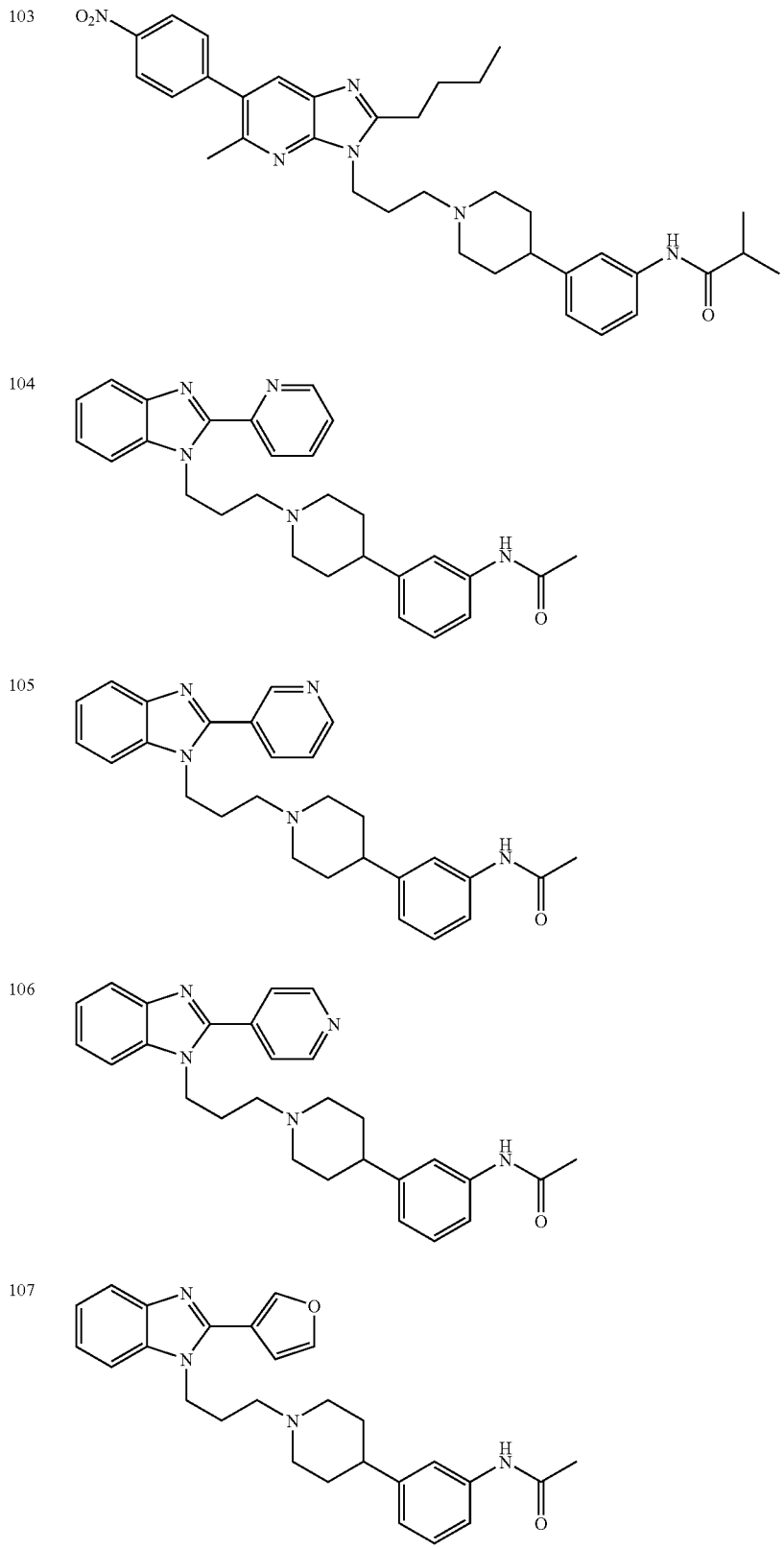

TABLE 1-continued
| Compound | Structure |
|---|---|
| 108 | 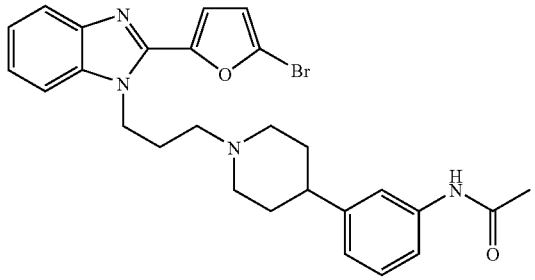 |
| 109 | 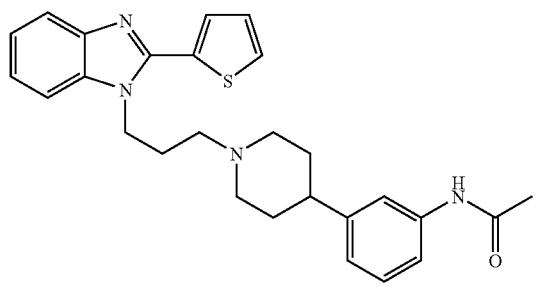 |
| 110 | 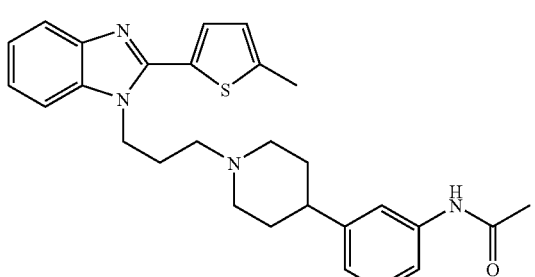 |
| 111 | 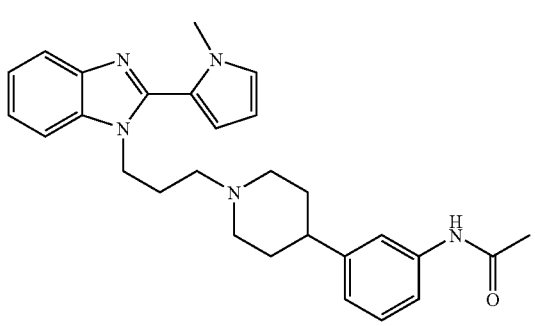 |
| 112 | 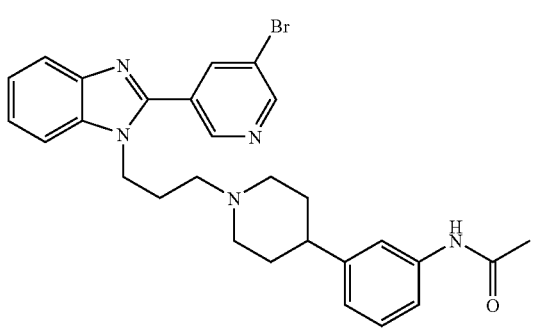 |

TABLE 1-continued

| Compound | Structure |
|---|---|
| 113 | 2-(6-chloropyridin-3-yl)-1-[3-[4-[3-(acetylamino)phenyl]piperidin-1-yl]propyl]-1H-benzimidazole |
| 114 | 2-(6-methylpyridin-3-yl)-1-[3-[4-[3-(acetylamino)phenyl]piperidin-1-yl]propyl]-1H-benzimidazole |
| 115 | 2-(2-methoxypyridin-3-yl)-1-[3-[4-[3-(acetylamino)phenyl]piperidin-1-yl]propyl]-1H-benzimidazole |
| 116 | 5-chloro-2-(pyridin-3-yl)-1-[3-[4-[3-(acetylamino)phenyl]piperidin-1-yl]propyl]-1H-benzimidazole |
| 117 | 5-nitro-2-(pyridin-3-yl)-1-[3-[4-[3-(acetylamino)phenyl]piperidin-1-yl]propyl]-1H-benzimidazole |

TABLE 1-continued
| Compound | Structure |
|---|---|
| 118 | 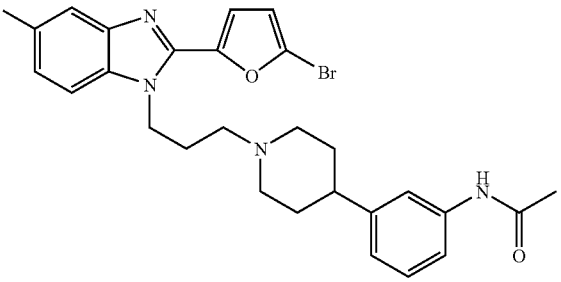 |
| 119 | 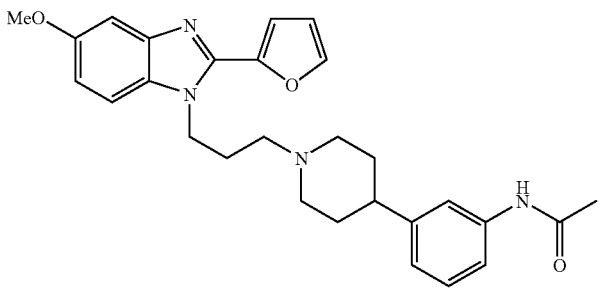 |
| 120 | 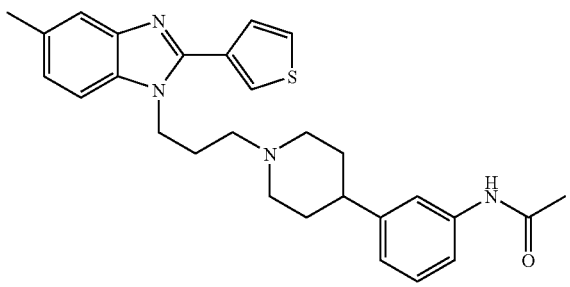 |
| 121 | 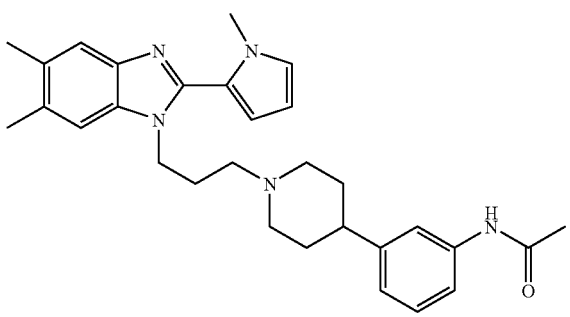 |
| 122 | 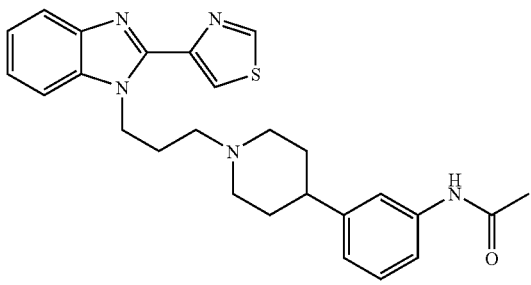 |

TABLE 1-continued
| Compound | Structure |
|---|---|
| 123 | 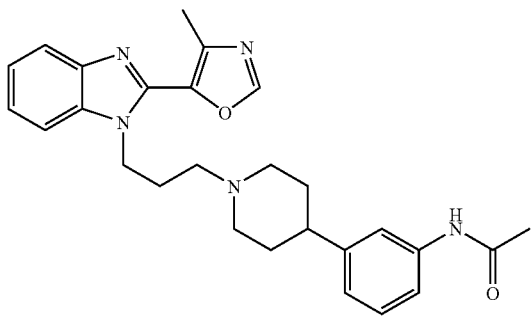 |
| 124 | 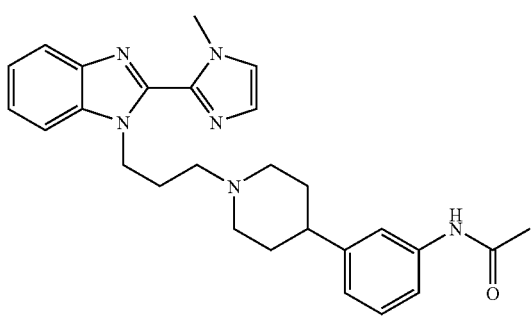 |
| 125 | 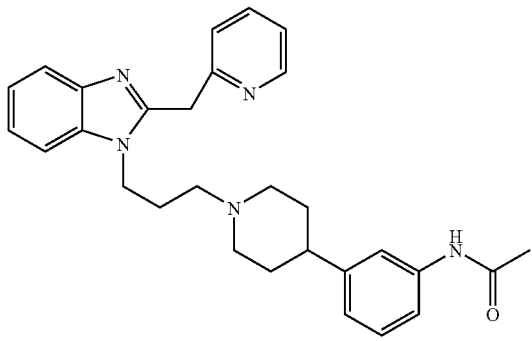 |
| 126 | 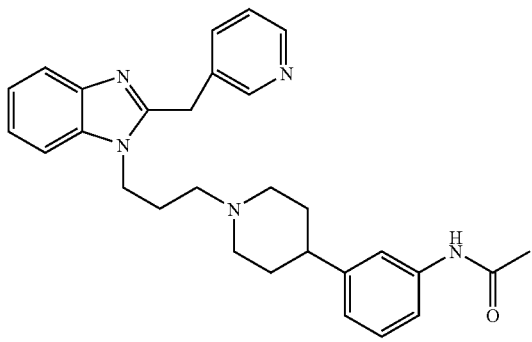 |

TABLE 1-continued

| Compound | Structure |
|---|---|
| 127 | 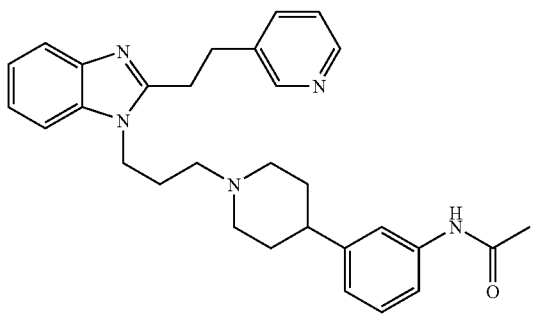 |

Further, the present invention provides a method for preparing the compound of formula (I).

The inventive compound of formula (I) can be prepared by subjecting a compound of formula (II) to a reaction with a compound of formula (III) in a solvent in the presence of a base:

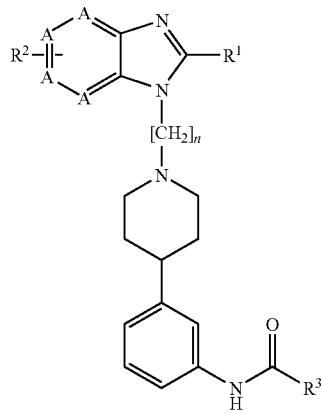

(I)

(II)

(III)

wherein, $R^1$, $R^2$, $R^3$, A and n are the same as defined in formula (I) and L is a leaving group such as methanesulfonyloxy (OMs), toluenesulfonyloxy (OTs) and halogen.

Alternatively, the compound of formula (I) can be prepared by subjecting a compound of formula (IV) to a reaction with a compound of formula (V) in a solvent in the presence of a base:

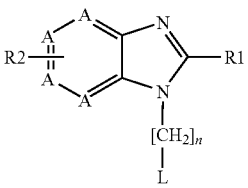

(IV)

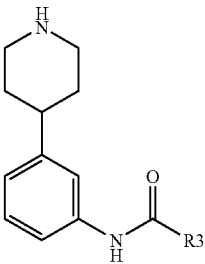

(V)

wherein, $R^1$, $R^2$, $R^3$, A and n are the same as defined in formula (I) and L is a leaving group such as OMs, OTs and halogen.

Examples of the base which may be used in the present invention include an organic base such as pyridine, triethylamine, N,N-diisopropylethylamine, 1,8-diazabicyclo-[5.4.0]undec-7-ene (DBU), and a mixture thereof; and an inorganic base such as NaOH, $Na_2CO_3$, $K_2CO_3$, $Cs_2CO_3$, and a mixture thereof. The base may be used in an equivalent or excessive amount.

Examples of the solvent which may be used in the present invention include an ether solvent such as tetrahydrofuran, dioxane, dichloromethane, and 1,2-dimethoxyethane; dimethyl formamide (DMF); dimethyl sulfoxide; acetonitrile; and a mixture thereof. The reaction may be conducted at a temperature ranging from room temperature to the boiling point of the solvent used.

The compound of formula (III) used as a starting material in the inventive method may be prepared by subjecting the compound of formula (V) to alkylation with

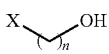

to obtain a compound of formula (V-1) and subjecting the compound of formula (V-1) to an acylation reaction with methanesulfonyl chloride (MsCl) or toluenesulfonyl chloride (TsCl); or by subjecting the compound of formula (V) to alkylation with

as shown in Reaction Scheme 1. The aryl piperidine compound of formula (V) may be prepared by the method disclosed in PCT Publication No. WO 03/004027.

Also, the compound of formula (IV) used as a starting material in the inventive method may be prepared by subjecting an imidazole compound to alkylation with

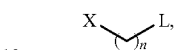

as shown in Reaction Scheme 2. The imidazole compound is commercially available, but it may be prepared by a conventionally known method (see PCT Publication No. WO 07/43943, Korean Patent No. 303944, and Oguchi et al., *J. Med. Chem.*, 43(16), 3052, 2000).

Reacation Scheme 1

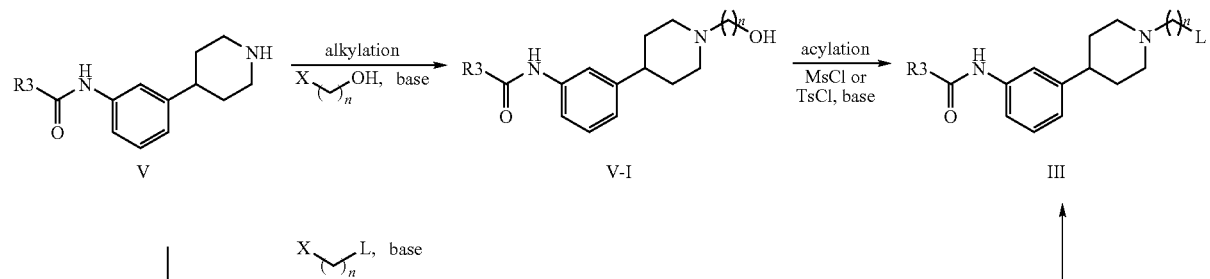

wherein, $R^3$ and n are the same as defined in formula (I), X is halogen, and L is a leaving group such as OMs, OTs and halogen.

In Reaction Scheme 1, the alkylation step may be conducted in a suitable solvent in the presence of a base, and

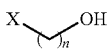

may be used in an equivalent or excessive amount.

Examples of the base which may be used in the alkylation include an organic base such as pyridine, triethylamine, N,N-diisopropylethylamine, 1,8-diazabicyclo-[5.4.0]undec-7-ene (DBU) and a mixture thereof; and an inorganic base such as NaOH, $Na_2CO_3$, $K_2CO_3$, $Cs_2CO_3$, and a mixture thereof. The base may be used in an equivalent or excessive amount.

Examples of the solvent which may be used in the alkylation include an ether such as tetrahydrofuran, dioxane, dichloromethane, and 1,2-dimethoxyethane; dimethyl formamide (DMF); dimethyl sulfoxide; acetonitrile; and a mixture thereof. The reaction may be conducted at a temperature ranging from 0° C. to the boiling point of the solvent used.

In Reaction Scheme 1, the acylation step may be conducted in a proper solvent in the presence of a base, and MsCl or TsCl may be used in an equivalent or excessive amount. The solvent and base may be the same as those used in the alkylation step. The reaction may be conducted at a temperature ranging from 0° C. to the boiling point of the solvent used.

Reaction Scheme 2

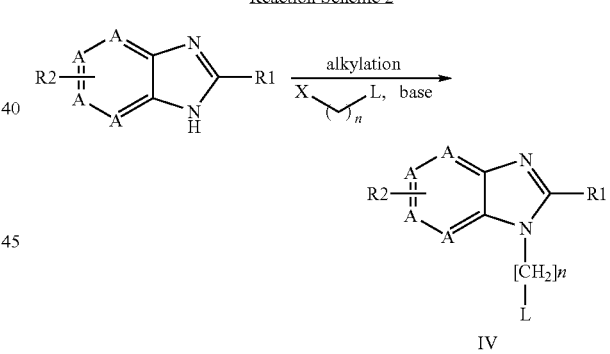

wherein, $R^1$, $R^2$, A and n are the same as defined in formula (I), X is halogen, and L is a leaving group such as OMs, OTs and halogen.

In Reaction Scheme 2, the alkylation may be conducted in a proper solvent in the presence of a base. The solvent and base may be the same as those used in the alkylation step of Reaction Scheme 1. The reaction may be conducted at a temperature ranging from room temperature to the boiling point of the solvent used.

The compound of formula (I) having various $R^3$ may be prepared by deacetylating the compound of formula (I) in the presence of an acid or base to obtain an aniline derivative and subjecting the aniline derivative to a reaction with one of various acyl chloride or carboxylic acid compounds to form an amide compound, as shown in Reaction Scheme 3.

Reaction Scheme 3

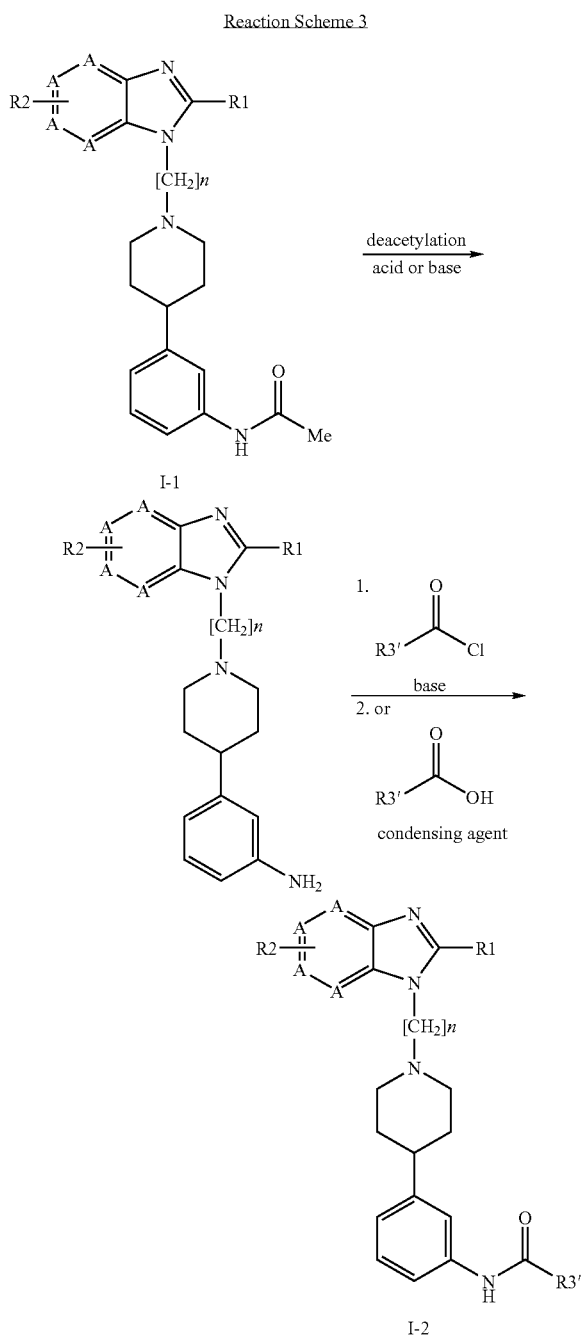

wherein, $R^1$, $R^2$, A and n are the same as defined in formula (I) and $R^{3'}$ represents $R^3$ of formula (I) excluding methyl.

In Reaction Scheme 3, the deacetylation step may be conducted in a suitable solvent in the presence of an acid or base. Examples of the acid include an inorganic acid such as hydrochloric acid and sulfuric acid in the form of an aqueous solution and an organic acid such as trifluoroacetic acid and methanesulfonic acid, in which the base may be used in an equivalent or excess amount. Examples of the base include NaOH, KOH, NaOMe, and NaOEt. Examples of the solvent include water, alcohol such as methanol, tetrahydrofuran, dioxane, acetonitrile, and a mixture thereof. Optionally, the solvent is not used. The reaction may be conducted at a temperature ranging from room temperature to the boiling point of the solvent used.

In Reaction Scheme 3, the amide forming step may be conducted by subjecting the aniline compound to a reaction with an acyl chloride in the presence of a base, or with a carboxylic acid derivative in the presence of a condensing agent, in a suitable solvent. Examples of the base include pyridine, triethylamine and N,N-diisopropylethylamine. Examples of the condensing agent include 1,3-dicyclohexylcarbodiimide (DCC), 1,3-diisopropylcarbodimide (DIC), 1-(3-dimethylaminopropyl)-3-ethylcarbodiimide hydrochloride (EDC), 1,1-carbonyldiimidazole (CDI). Also, the condensing agent may be used in the form of a mixture with an organic base such as 1-hydroxybenzotriazole (HOBT), 4-dimethylaminopyridine (DMAP), pyridine, triethylamine, N,N-diisopropylethylamine and 1,8-diazabicyclo-[5.4.0]undec-7-ene (DBU). Examples of the solvent include dichloromethane, chloroform, tetrahydrofuran, N,N-dimethyl formamide (DMF), acetonitrile, dimethyl sulfoxide (DMSO) and a mixture thereof. The reaction is preferably conducted at room temperature.

The present invention further provides a pharmaceutical composition for preventing or treating an MCH-related disease, comprising the inventive compound of formula (I) or a pharmaceutically acceptable salt thereof as an active ingredient.

Examples of the MCH-related disease include obesity, depression, anxiety, diabetes, metabolic disturbance, and schizophrenia.

The pharmaceutical composition of the present invention may be orally or parenterally administered and it may be formulated using conventional pharmaceutically acceptable diluents or excipients such as fillers, extenders, binders, wetting agents, disintegrants and surfactants.

The solid formulation for oral administration may contain at least one excipient such as starch, calcium carbonate, sucrose, lactose and gelatin, and lubricants such as magnesium stearate and talc. The liquid formulation for oral administration may take various forms such as suspension, solution, emulsion and syrup, which may contain diluents such as water and liquid paraffin, and various excipients such as wetting agents, sweetening agents, odorants and preservatives.

The formulation for parenteral administration may be in the form of steriled aqueous solution, non-aqueous solution, suspension, emulsion, freeze-dried product, and suppository. The non-aqueous solution or suspension form may contain propylene glycol, polyethylene glycol, vegetable oil such as olive oil, and injectable ester such as ethylolate. The suppository may be prepared by using a base such as witepsol, macrogol, Tween 61, cacao butter, laurin butter, and glycerol gelatin.

The amount of the inventive compound of formula (I) or a pharmaceutically salt thereof actually administered will be determined depending on various factors including the age, body weight, sex and condition of the patient and the chosen route of administration. The typical daily dosage of the compound of formula (I) is 0.1 to 1,000 mg, preferably 1 to 500 mg for an average 70 kg adult patient, and can be administered in a single dose or in divided doses.

The present invention will be described in further detail with reference to Examples. However, it should be understood that the present is not restricted by the specific Examples.

The molecular structures of the subject invention were confirmed by infrared spectrometry, NMR spectroscopy, mass spectroscopy, liquid chromatography, X-ray crystallography, rotation measurement, or comparison of ultimate analysis values for a representative compound with a real measurement values.

Preparation of Formula (V-1)

Preparation Examples 1 to 3

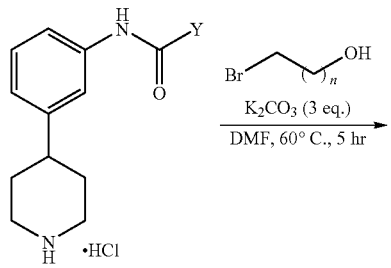

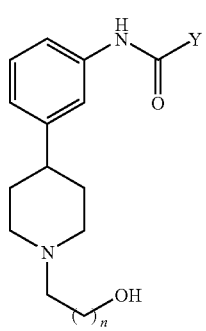

Preparation Example 1

Preparation of 3-[4-(3-acetylaminophenyl)piperidin-1-yl]propan-1-ol (Formula (V-1); n=2, Y=Me)

5.3 g (20.8 mmol) of 4-(3-acetylaminophenyl)piperidine hydrochloride was dissolved in 50 ml of N,N-dimethylformamide, and then 3.8 g (27.0 mmol) of 3-bromo-1-propanol and 8.6 g (62 mmol) of $K_2CO_3$ were added to the resulting solution, followed by treating the mixture at 60° C. for 5 hours. The reaction mixture was combined with 150 ml of water and extracted with ethylacetate (100 ml×5), and then the combined organic layer was dried over anhydrous sodium sulfate, and filtered. The solvent was removed from the filtrate under a reduced pressure, and the resulting residue was refined by silica gel column chromatography (10% methanol/ $CH_2Cl_2$) to obtain 4.8 g (yield 85%) of the title compound.
$^1$H-NMR (300 MHz, $CDCl_3$) δ 1.76-1.86 (m, 6H), 2.13 (m, 2H), 2.17 (s, 3H), 2.55 (m, 1H), 2.71 (t, 2H), 3.25 (brd, 2H), 3.84 (t, 2H), 6.95 (d, 1H), 7.19-7.31 (m, 3H), 7.43 (s, 1H, NH); MS (m/e, M$^+$): 276

Preparation Example 2

Preparation of 3-[4-(3-isobutyrylaminophenyl)piperidin-1-yl]propan-1-ol (Formula (V-1); n=2, Y=i-Pr)

3.05 g (yield 81%) of the title compound was obtained by repeating the procedure of Preparation Example 1 except for using 3.5 g (12.4 mmol) of 3-[4-(3-isobutyrylaminophenyl) piperidine]hydrochloride.
$^1$H-NMR (300 MHz, $CDCl_3$) δ 1.25 (d, 6H), 1.69-1.78 (m, 4H), 1.83 (brd, 2H), 2.05 (t, 2H), 2.50 (m, 1H), 2.55 (m, 1H), 2.66 (t, 2H), 3.17 (brd, 2H), 3.83 (t, 2H), 6.92 (d, 1H), 7.23 (dd, 1H), 7.35-7.38 (m, 2H), 7.40 (s, 1H, NH); MS (m/e, M$^+$): 304

Preparation Example 3

Preparation of 2-[4-(3-acetylaminophenyl)piperidin-1-yl]ethanol (Formula (V-1); n=1, Y=Me)

2.0 g (7.8 mmol) of 4-(3-acetylaminophenyl)piperidine hydrochloride was dissolved in 20 ml of N,N-dimethylformamide, and then 1.3 g (10.2 mmol) of 2-bromoethanol and 3.2 g (23.4 mmol) of $K_2CO_3$ were added to the resulting solution, followed by treating the mixture at 60° C. for 5 hours. The reaction mixture was combined with 100 ml of water and extracted with ethylacetate (70 ml×5), and then the combined organic layer was dried over anhydrous sodium sulfate, and filtered. The solvent was removed from the filtrate under a reduced pressure, and the resulting residue was refined by silica gel column chromatography (10% methanol/ $CH_2Cl_2$) to obtain 1.14 g (yield 56%) of the title compound.
$^1$H-NMR (300 MHz, $CDCl_3$) δ 1.73-1.82 (m, 4H), 2.09 (m, 2H), 2.18 (s, 3H), 2.40 (m, 1H), 2.57 (m, 2H), 3.05 (brd, 2H), 3.63 (t, 2H), 6.62 (d, 1H), 6.96-7.40 (m, 4H; MS (m/e, M$^+$): 262

Preparation of Formula (III)

Preparation Examples 4 to 6

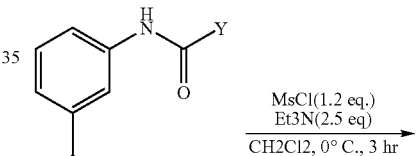

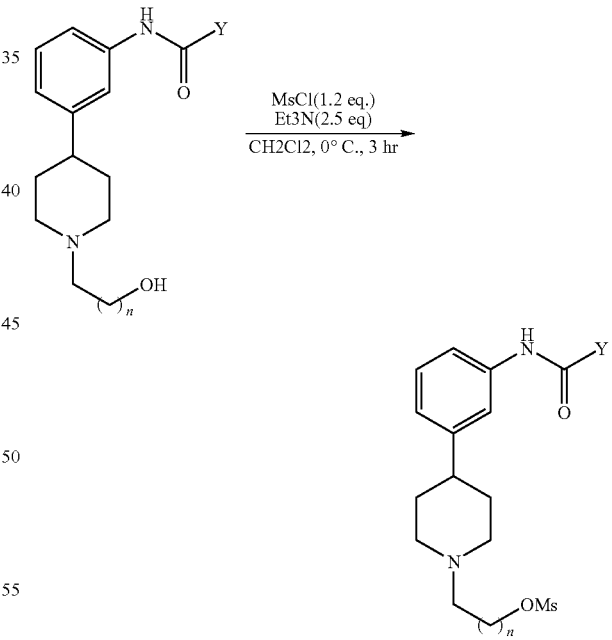

Preparation Example 4

Preparation of 3-[4-(3-acetylaminophenyl)piperidin-1-yl]propyl methanesulfonate (Formula (III); n=2, Y=Me)

4.5 g (16.3 mmol) of the compound obtained in Preparation Example 1 was dissolved in 70 ml of dichloromethane, and then cooled to 0° C. and 6.7 ml (48.0 mmol) of triethylamine was added to the resulting solution. Subsequently, 1.15 ml (19.5 mmol) of methanesulfonyl chloride, which was diluted in 10 ml of $CH_2Cl_2$, was slowly added to the solution, followed by mixing at 0° C. for 3 hours. The reaction mixture was combined with a mixture of 100 ml of water and saturated solution 30 ml of $NaHCO_3$ and extracted with $CH_2Cl_2$ (100 ml×2), and then a combined organic layer was dried over anhydrous sodium sulfate, and filtered. The solvent was removed from the filtrate under a reduced pressure to obtain 5.2 g (yield 90%) of the title compound. The resulting compound was used in a next reaction without further being refined.

$^1$H-NMR (300 MHz, $CDCl_3$) δ 1.90-2.03 (m, 4H), 2.21 (s, 3H), 2.39 (m, 1H), 2.43 (m, 2H), 2.80 (s, 3H), 2.82 (m, 2H), 3.07 (m, 2H), 3.58 (m, 2H), 4.40 (t, 2H), 6.93 (d, 1H), 7.20 (dd, 1H), 7.42 (brs, 1H, NH), 7.58 (d, 1H), 8.48 (s, 1H, NH); MS (m/e, M$^+$): 354

Preparation Example 5

Preparation of 3-[4-(3-isobutyrylaminophenyl)piperidin-1-yl]propyl methanesulfonate (Formula (III); n=2, Y=i-Pr)

3.5 g (yield 93%) of the title compound was obtained by repeating the procedure of Preparation Example 4 except for using 3.0 g (9.87 mmol) of the compound obtained by Preparation Example 2.

$^1$H-NMR (300 MHz, $CDCl_3$) δ 1.23 (d, 6H), 1.77-1.94 (m, 4H), 2.62 (m, 2H), 2.65 (m, 1H), 2.76 (m, 1H), 2.79 (s, 3H), 3.38 (m, 2H), 3.83 (brd, 2H), 4.32 (t, 2H), 4.40 (t, 2H), 6.74 (d, 1H), 7.17 (dd, 1H), 7.51 (s, 1H), 7.86 (d, 1H), 9.34 (s, 1H, NH); MS (m/e, M$^+$): 382

Preparation Example 6

Preparation of 2-[4-(3-acetylaminophenyl)piperidin-1-yl]ethyl methanesulfonate (Formula (III); n=1, Y=Me)

0.78 g (yield 75%) of the title compound was obtained by repeating the procedure of Preparation Example 4 except for using 0.8 g (3.05 mmol) of the compound obtained by Preparation Example 3. The resulting compound was used in a next reaction without further being refined.

$^1$H-NMR (300 MHz, $CDCl_3$) δ 1.75-1.86 (m, 4H), 2.19 (s, 3H), 2.45 (m, 1H), 2.76 (s, 3H), 3.01 (m, 2H), 3.14 (t, 2H), 3.40 (t, 2H), 3.48 (t, 2H), 6.88 (d, 1H), 7.17-7.49 (m, 4H); MS (m/e, M$^+$): 340

Preparation of Formula (IV)

Preparation Examples 7 to 10

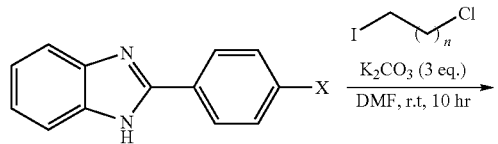

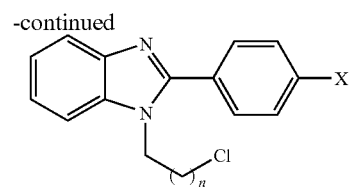

Preparation Example 7

Preparation of 1-(4-chlorobutyl)-2-phenyl-1H-benzimidazole (Formula (IV); n=3, X=H)

2.5 g (12.88 mmol) of 2-phenyl-benzimidazole was dissolved in 30 ml of N,N-dimethylformamide, and 5.3 g (38.6 mmol) of $K_2CO_3$ and 2.0 ml (16.7 mmol) of 1-chloro-4-iodobutane were added to the resulting solution, followed by mixing the mixture at a room temperature for 10 hours. The reactant was combined with 100 ml of water and extracted with ethylacetate (70 ml×5) being washed with water and a sodium hydroxide solution, and then the combined organic layer was dried over anhydrous sodium sulfate and filtered. The solvent was removed from the filtrate under a reduced pressure, and the resulting residue was refined by silica gel column chromatography (n-hexane/ethylacetate=2/1) to obtain 3.5 g (yield 96%) of the title compound.

$^1$H NMR (300 MHz, $CDCl_3$) δ 1.69 (m, 2H), 2.00 (m, 2H), 3.43 (t, 2H), 4.29 (t, 2H), 7.30-7.50 (m, 3H), 7.55 (m, 3H), 7.72 (m, 2H), 7.83 (m, 1H); MS (m/e, M$^+$): 285

Preparation Example 8

Preparation of 1-(4-chlorobutyl)-2-(4-chlorophenyl)-1H-benzimidazole (Formula (IV); n=3, X=Cl)

2.6 g (yield 93%) of the title compound was obtained by repeating the procedure of Preparation Example 7 except for using 2.0 g (8.73 mmol) of 2-(4-chlorophenyl)benzimidazole.

$^1$H NMR (300 MHz, $CDCl_3$) δ 1.69 (m, 2H), 2.00 (m, 2H), 3.46 (t, 2H), 4.27 (t, 2H), 7.34 (m, 2H), 7.41 (m, 1H), 7.51 (d, 2H), 7.66 (d, 2H), 7.81 (m, 1H); MS (m/e, M$^+$): 319, 283, 255, 206

Preparation Example 9

Preparation of 1-(5-chloropentyl)-2-phenyl-1H-benzimidazole (Formula (IV); n=4, X=H)

2.5 g (12.88 mmol) of 2-phenyl-benzimidazole was dissolved in 30 ml of N,N-dimethylformamide, and 5.3 g (38.6 mmol) of $K_2CO_3$ and 2.3 ml (16.7 mmol) of 1-chloro-5-iodopetane were added to the resulting solution, followed by mixing the solution at a room temperature for 10 hours. The reaction mixture was combined with 100 ml of water and extracted with ethylacetate (70 ml×5) being washed with water and a sodium hydroxide solution, and then the combined organic layer was dried over anhydrous sodium sulfate, and filtered. The solvent was removed under a reduced pressure, and the resulting residue was refined by silica gel column chromatography (n-hexane/ethylacetate=3/1) to obtain 3.16 g (yield 82%) of the title compound.

¹H NMR (300 MHz, CDCl₃) δ 1.35 (m, 2H), 1.67-1.87 (m, 4H), 3.41 (t, 2H), 4.25 (t, 2H), 7.31 (m, 2H), 7.39 (m, 1H), 7.51-7.55 (m, 3H), 7.70 (m, 2H), 7.81 (m, 1H); MS (m/e, M⁺): 298

Preparation Example 10

Preparation of 1-(5-chloropentyl)-2-(4-chlorophenyl)-1H-benzimidazole (Formula (IV); n=4, X=Cl)

2.9 g (yield 80%) of the title compound was obtained by repeating the procedure of Preparation Example 8 except for using 2.5 g (10.92 mmol) of 2-(4-chlorophenyl)benzimidazole.
¹H NMR (300 MHz, CDCl₃) δ 1.35 (m, 2H), 1.68-1.87 (m, 4H), 3.43 (t, 2H), 4.24 (t, 2H), 7.29-7.41 (m, 3H), 7.50 (d, 2H), 7.64 (d, 2H), 7.82 (m, 1H); MS (m/e, M⁺): 333

Preparation of Imidazole Derivative

Examples 1 to 4

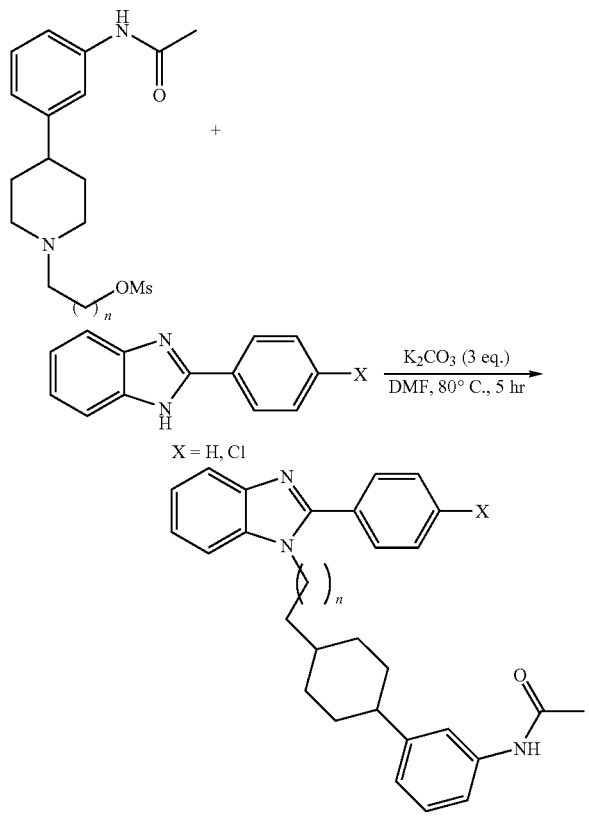

X = H, Cl

Example 1

2-phenyl-1-{2-[4-(3-acetylaminophenyl)piperidin-1-yl]ethyl}-1H-benzimidazole 70 mg (0.36 mmol) of 2-phenylbenzimidazole was dissolved in 5 ml of N,N-dimethylformamide, and 122 mg (0.36 mmol) of 2-[4-(3-acetylaminophenyl)piperidin-1-yl]ethyl-methanesulfonate obtained by Preparation Example 6 and 150 mg (1.08 mmol) of K₂CO₃ were added to the resulting solution, followed by treating the mixture at 80° C. for 5 hours. The reaction mixture was combined with 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (5% MeOH/CH₂Cl₂) to obtain 56 mg (yield 36%) of the title compound.
¹H NMR (300 MHz, CDCl₃) δ 1.55 (-1.77 (m, 6H), 2.06 (m, 2H), 2.16 (m, 3H), 2.43 (m, 1H), 2.78 (t, 2H), 2.85 (br-d, 2H), 4.39 (t, 2H), 6.92 (d, 1H), 7.23-7.38 (m, 5H), 7.50-7.54 (m, 4H), 7.79-7.83 (m, 3H); MS (m/e, M⁺): 438, 231, 207, 188, 160, 146

Example 2

2-(4-chlorophenyl)-1-{2-[4-(3-acetylaminophenyl)piperidin-1-yl]ethyl}-1H-benzimidazole 45 mg (yield 31%) of the title compound was obtained by repeating the procedure of Example 1 except for using 70 mg (0.31 mmol) of 2-(4-chlorophenyl)benzimidazole.
¹H NMR (300 MHz, CDCl₃) δ 1.50 (-1.79 (m, 6H), 2.08 (m, 2H), 2.17 (m, 3H), 2.45 (m, 1H), 2.78 (t, 2H), 2.85 (br-d, 2H), 4.37 (t, 2H), 6.92 (d, 1H), 7.24-7.37 (m, 5H), 7.45 (m, 1H), 7.50 (d, 2H, J=8.4 Hz), 7.78 (d, 2H, J=8.4 Hz), 7.84 (m, 1H); MS (m/e, M⁺): 472, 231, 188, 160, 146

Example 3

2-phenyl-1-{3-[4-(3-acetylaminophenyl)piperidin-1-yl]propyl}-1H-benzimidazole 70 mg (0.36 mmol) of 2-phenylbenzimidazole was dissolved in 5 ml of N,N-dimethylformamide, and 127 mg (0.36 mmol) of 3-[4-(3-acetylaminophenyl)piperidin-1-yl]propyl-methanesulfonate obtained by Preparation Example 4 and 150 mg (1.08 mmol) of K₂CO₃ were added to the resulting solution, followed by mixing the solution at 80° C. for 5 hours. The reaction mixture was combined with 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (5% MeOH/CH₂Cl₂) to obtain 75 mg (yield 46%) of the title compound.
¹H NMR (300 MHz, CDCl₃) δ 1.61-1.77 (m, 4H), 1.89-2.01 (m, 4H), 2.15 (s, 3H), 2.28 (t, 2H), 2.42 (m, 1H), 2.83 (brd, 2H), 4.37 (t, 2H), 6.94 (d, 1H, J=7.3 Hz), 7.24-7.32 (m, 4H), 7.46 (m, 2H), 7.47-7.53 (m, 4H), 7.73 (m, 2H), 7.80 (m, 1H); MS (m/e, M⁺): 452, 424, 367, 257, 231

Example 4

2-(4-chlorophenyl)-1-{3-[4-(3-acetylaminophenyl)piperidin-1-yl]propyl}-1H-benzimidazole 77 mg (yield 51%) of the title compound was obtained by repeating the procedure of Example 3 except for using 70 mg (0.31 mmol) of 2-(4-chlorophenyl)benzimidazole.
¹H NMR (300 MHz, CDCl₃) δ 1.59-1.79 (m, 4H), 1.90-2.01 (m, 4H), 2.16 (s, 3H), 2.26 (t, 2H), 2.43 (m, 1H), 2.82 (brd, 2H), 4.37 (t, 2H), 6.95 (d, 1H, J=7.5 Hz), 7.24-7.37 (m, 5H), 7.46 (m, 1H), 7.52 (d, 2H, J=8.4 Hz), 7.71 (d, 2H, J=8.4 Hz), 7.80 (m, 1H); MS (m/e, M⁺): 486, 458, 311, 270, 257, 231

Preparation of Imidazole Derivative

Examples 5 to 8

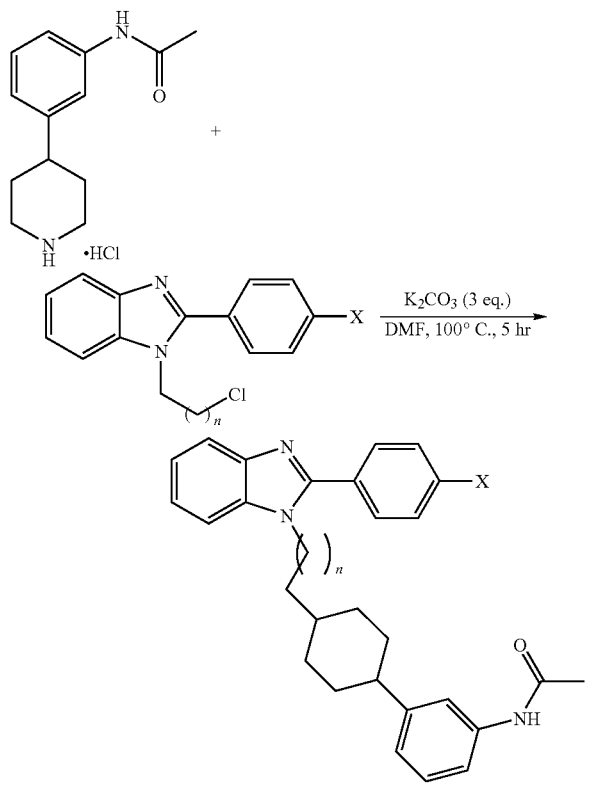

Example 5

2-phenyl-1-{4-[4-(3-acetylaminophenyl)piperidin-1-yl]butyl}-1H-benzimidazole 100 mg (0.39 mmol) of 4-(3-acetylaminophenyl)piperidine hydrochloride was dissolved in 5 ml of N,N-dimethylformamide, and 112 mg (0.39 mmol) of 1-(4-chlorobutyl)-2-phenyl-1H-benzimidazole obtained by Preparation Example 7, 163 mg (1.17 mmol) of $K_2CO_3$ and 20 mg (0.12 mmol) of KI were added to the resulting solution, followed by mixing the solution at 100° C. for 5 hours. The reaction mixture was combined in 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (10% MeOH/$CH_2Cl_2$) to obtain 104 mg (yield 57%) of the title compound.

¹H NMR (300 MHz, $CDCl_3$) δ 1.48 (m, 2H), 1.69-1.99 (m, 8H), 2.15 (s, 3H), 2.30 (t, 2H), 2.45 (m, 1H), 2.90 (br, 2H), 4.28 (t, 2H), 7.23-7.38 (m, 6H), 7.45-7.53 (m, 4H), 7.72 (m, 2H), 7.81 (m, 1H); MS (m/e, M⁺): 467

Example 6

2-(4-chlorophenyl)-1-{4-[4-(3-acetylaminophenyl)piperidin-1-yl]butyl}-1H-benzimidazole 127 mg (yield 65%) of the title compound was obtained by repeating the procedure of Example 5 except for using 100 mg (0.39 mmol) of 4-(3-acetylaminophenyl)piperidine hydrochloride, and 90 mg (0.39 mmol) of 1-(4-chlorobutyl)-2-(4-chlorophenyl)-1H-benzimidazole resulting from Preparation Example 8.

¹H NMR (300 MHz, $CDCl_3$) δ 1.48 (m, 2H), 1.71-2.00 (m, 8H), 2.15 (s, 3H), 2.30 (t, 2H), 2.42 (m, 1H), 2.91 (br, 2H), 4.26 (t, 2H), 6.95 (d, 1H), 7.23-7.38 (m, 6H), 7.45-7.52 (m, 3H), 7.67 (d, 2H), 7.80 (m, 1H); MS (m/e, M⁺): 500, 458, 324, 284,

Example 7

2-phenyl-1-{5-[4-(3-acetylaminophenyl)piperidin-1-yl]pentyl}-1H-benzimidazole 120 mg (yield 55%) of the title compound was obtained by repeating the procedure of Example 5 except for using 100 mg (0.39 mmol) of 4-(3-acetylaminophenyl)piperidine hydrochloride, and 103 mg (0.39 mmol) of 1-(5-chloropentyl)-2-phenyl-1H-benzimidazole resulting from Preparation Example 9.

5 g: ¹H NMR (300 MHz, $CDCl_3$) δ 1.26 (m, 2H), 1.47 (m, 2H), 1.73-1.96 (m, 8H), 2.16 (s, 3H), 2.27 (t, 2H), 2.45 (m, 1H), 2.93 (brd, 2H), 4.25 (t, 2H), 6.95 (d, 1H), 7.26-7.41 (m, 7H), 7.51 (m, 3H), 7.70 (m, 2H), 7.80 (m, 1H); MS (m/e, M⁺): 480

Example 8

2-(4-chlorophenyl)-1-{5-[4-(3-acetylaminophenyl)piperidin-1-yl]pentyl}-1H-benzimidazole 118 mg (yield 59%) of the title compound was obtained by repeating the procedure of Example 5 except for using 100 mg (0.39 mmol) of 4-(3-acetylaminophenyl)piperidine hydrochloride, and 130 mg (0.39 mmol) of 1-(5-chloropentyl)-2-(4-chlorophenyl)-1H-benzimidazole resulting from Preparation Example 10.

¹H NMR (300 MHz, $CDCl_3$) δ 1.27 (m, 2H), 1.48 (m, 2H), 1.72-1.86 (m, 6H), 1.99 (m, 2H), 2.16 (s, 3H), 2.28 (t, 2H), 2.46 (m, 1H), 2.94 (brd, 2H), 4.24 (t, 2H), 6.97 (d, 1H), 7.23-7.41 (m, 7H), 7.50 (d, 2H), 7.66 (d, 2H), 7.68 (m, 1H); MS (m/e, M⁺): 515

Preparation of Imidazole Derivative

Examples 9 to 63

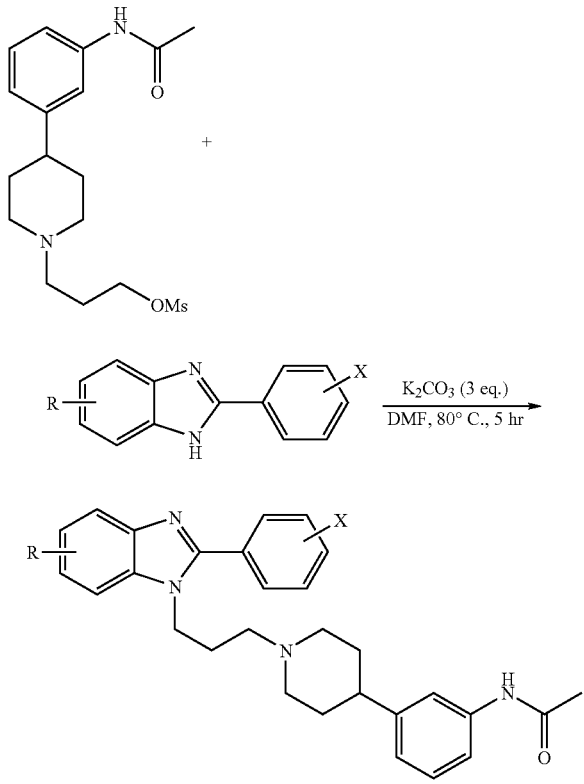

Example 9

2-(2-chlorophenyl)-1-{3-[4-(3-acetylaminophenyl)piperidin-1-yl]propyl}-1H-benzimidazole 70 mg (0.31 mmol) of 2-(2-chlorophenyl)-1H-benzimidazole was dissolved in 5 ml of N,N-dimethylformamide, and 110 mg (0.31 mmol) of 3-[4-(3-acetylaminophenyl)piperidin-1-yl]propyl methanesulfonate obtained by Preparation Example 4 and 130 mg (0.93 mmol) of $K_2CO_3$ were added to the resulting solution, followed by mixing the solution at 80° C. for 5 hours. The reaction mixture was combined in 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (5% MeOH/$CH_2Cl_2$) to obtain 87 mg (yield 58%) of the title compound.

$^1$H NMR (300 MHz, $CDCl_3$) δ 1.59-1.75 (m, 4H), 1.85-1.90 (m, 4H), 2.16 (s, 3H), 2.23 (t, 2H), 2.38 (m, 1H), 2.78 (brd, 2H), 4.17 (t, 2H), 6.93 (d, 1H, J=7.5 Hz), 7.24-7.56 (m, 11H), 7.83 (m, 1H); MS (m/e, M$^+$): 486, 451, 375, 346, 269, 257

Example 10

2-(3-chlorophenyl)-1-{3-[4-(3-acetylaminophenyl)piperidin-1-yl]propyl}-1H-benzimidazole 83 mg (yield 55%) of the title compound was obtained by repeating the procedure of Example 9 except for using 70 mg (0.31 mmol) of 2-(3-chlorophenyl)-1H-benzimidazole.

$^1$H NMR (300 MHz, $CDCl_3$) δ 1.59 (−1.78 (m, 4H), 1.89-1.99 (m, 4H), 2.16 (m, 3H), 2.27 (t, 2H), 2.46 (m, 1H), 2.82 (br-d, 2H), 4.38 (t, 2H), 6.94 (d, 1H), 7.24-7.50 (m, 9H), 7.65 (d, 1H), 7.78 (s, 1H, NH), 7.83 (d, 1H); MS (m/e, M$^+$): 487

Example 11

2-(4-bromophenyl)-1-{3-[4-(3-acetylaminophenyl)piperidin-1-yl]propyl}-1H-benzimidazole 70 mg (yield 51%) of the title compound was obtained by repeating the procedure of Example 9 except for using 70 mg (0.25 mmol) of 2-(4-bromophenyl)-1H-benzimidazole.

$^1$H NMR (300 MHz, $CDCl_3$) δ 1.62 (m, 2H), 1.74 (m, 2H), 1.93 (m, 4H), 2.16 (s, 3H), 2.26 (t, 2H), 2.43 (m, 1H), 2.79 (brd, 2H), 4.36 (t, 2H), 6.94 (d, 1H), 7.25-7.37 (m, 6H), 7.46 (m, 1H), 7.66 (m, 4H), 7.81 (m, 1H); MS (m/e, M$^+$): 531

Example 12

2-(3,4-dichlorophenyl)-1-{3-[4-(3-acetylaminophenyl)piperidin-1-yl]propyl}-1H-benzimidazole 67 mg (yield 48%) of the title compound was obtained by repeating the procedure of Example 9 except for using 70 mg (0.27 mmol) of 2-(3,4-dichlorophenyl)-1H-benzimidazole.

$^1$H NMR (300 MHz, $CDCl_3$) δ 1.55-1.64 (m, 2H), 1.76 (m, 2H), 1.89-1.99 (m, 4H), 2.17 (m, 3H), 2.26 (t, 2H), 2.42 (m, 1H), 2.80 (br-d, 2H), 4.39 (t, 2H), 6.94 (d, 1H), 7.24-7.35 (m, 6H), 7.48 (m, 1H), 7.50 (m, 2H) 7.82 (d, 1H), 7.92 (s, 1H); MS (m/e, M$^+$): 521, 479, 345, 304, 289, 257, 231

Example 13

2-(3-bromophenyl)-1-{3-[4-(3-acetylaminophenyl)piperidin-1-yl]propyl}-1H-benzimidazole 67 mg (yield 50%) of the title compound was obtained by repeating the procedure of Example 9 except for using 70 mg (0.25 mmol) of 2-(3-bromophenyl)-1H-benzimidazole.

$^1$H NMR (300 MHz, $CDCl_3$) δ 1.59-1.78 (m, 4H), 1.89-1.99 (m, 4H), 2.16 (m, 3H), 2.27 (t, 2H), 2.46 (m, 1H), 2.83 (br-d, 2H), 4.38 (t, 2H), 6.96 (d, 1H), 7.24-7.47 (m, 8H), 7.62-7.71 (m, 2H), 7.80 (d, 1H), 7.94 (s, 1H); MS (m/e, M$^+$): 531, 451, 357, 316, 257, 231

Example 14

2-(2-iodophenyl)-1-{3-[4-(3-acetylaminophenyl)piperidin-1-yl]propyl}-1H-benzimidazole 88 mg (yield 49%) of the title compound was obtained by repeating the procedure of Example 9 except for using 100 mg (0.31 mmol) of 2-(2-iodophenyl)-1H-benzimidazole.

$^1$H NMR (300 MHz, $CDCl_3$) δ 1.65-1.82 (m, 4H), 1.92-2.05 (m, 4H), 2.15 (m, 3H), 2.37 (m, 2H), 2.45 (m, 1H), 2.92 (br-d, 2H), 4.16 (t, 2H), 6.91 (d, 1H, J=6.7 Hz), 7.20-7.53 (m, 10H), 7.83 (d, 1H, J=7.3 Hz), 7.98 (d, 1H); MS (m/e, M$^+$): 578, 451, 347, 256, 231

Example 15

2-(2-fluorophenyl)-1-{3-[4-(3-acetylaminophenyl)piperidin-1-yl]propyl}-1H-benzimidazole 103 mg (yield 47%) of the title compound was obtained by repeating the procedure of Example 9 except for using 100 mg (0.47 mmol) of 2-(2-fluorophenyl)-1H-benzimidazole.

$^1$H NMR (300 MHz, CDCl$_3$) δ 1.58 (m, 2H), 1.72 (m, 2H), 1.91 (m, 4H), 2.17 (s, 3H), 2.23 (t, 2H), 2.37 (m, 1H), 2.81 (brd, 2H), 4.24 (t, 2H), 6.92 (d, 1H), 7.21-7.34 (m, 7H), 7.39 (s, 1H), 7.48 (m, 2H), 7.66 (t, 1H), 7.82 (dd, 1H); MS (m/e, M$^+$): 470

Example 16

2-(2,4-dichlorophenyl)-1-{3-[4-(3-acetylaminophenyl)piperidin-1-yl]propyl}-1H-benzimidazole 110 mg (yield 56%) of the title compound was obtained by repeating the procedure of Example 9 except for using 100 mg (0.38 mmol) of 2-(2,4-dichlorophenyl)-1H-benzimidazole.

$^1$H NMR (300 MHz, CDCl$_3$) δ 1.57 (m, 2H), 1.65 (m, 2H), 1.91 (m, 4H), 2.17 (s, 3H), 2.25 (t, 2H), 2.43 (m, 1H), 2.84 (brd, 2H), 4.16 (t, 2H), 6.93 (d, 1H), 7.25-7.37 (m, 8H), 7.43 (d, 1H), 7.49 (d, 1H), 7.59 (d, 1H), 7.82 (d, 1H); MS (m/e, M$^+$): 521

Example 17

2-(2-methoxyphenyl)-1-{3-[4-(3-acetylaminophenyl)piperidin-1-yl]propyl}-1H-benzimidazole 98 mg (yield 46%) of the title compound was obtained by repeating the procedure of Example 9 except for using 100 mg (0.44 mmol) of 2-(2-methoxyphenyl)-1H-benzimidazole.

$^1$H NMR (300 MHz, CDCl$_3$) δ 1.66-1.83 (m, 4H), 1.84-2.04 (m, 4H), 2.17 (s, 3H), 2.35 (t, 2H), 2.37 (m, 1H), 2.89 (br, 2H), 3.69 (s, 3H), 4.07 (t, 2H), 6.90 (d, 1H), 7.05 (d, 1H), 7.13 (dd, 1H), 7.23-7.37 (m, 4H), 7.42-7.45 (m, 2H), 7.50 (dd, 1H), 7.57 (d, 1H), 7.79 (d, 1H); MS (m/e, M$^+$): 482

Example 18

2-(3-methoxyphenyl)-1-{3-[4-(3-acetylaminophenyl)piperidin-1-yl]propyl}-1H-benzimidazole 102 mg (yield 48%) of the title compound was obtained by repeating the procedure of Example 9 except for using 100 mg (0.44 mmol) of 2-(3-methoxyphenyl)-1H-benzimidazole.

$^1$H NMR (300 MHz, CDCl$_3$) δ 1.58 (m, 2H), 1.71 (m, 2H), 1.90 (m, 4H), 2.12 (s, 3H), 2.26 (t, 2H), 2.39 (m, 1H), 2.78 (d, 2H), 3.84 (s, 3H), 4.37 (t, 2H), 6.94 (d, 1H), 7.04 (d, 1H), 7.21-7.45 (m, 9H), 7.79 (dd, 1H), 7.98 (s, 1H); MS (m/e, M$^+$): 482

Example 19

2-(4-methoxyphenyl)-1-{3-[4-(3-acetylaminophenyl)piperidin-1-yl]propyl}-1H-benzimidazole 98 mg (yield 46%) of the title compound was obtained by repeating the procedure of Example 9 except for using 100 mg (0.44 mmol) of 2-(4-methoxyphenyl)-1H-benzimidazole.

$^1$H NMR (300 MHz, CDCl$_3$) δ 1.61 (m, 2H), 1.72 (m, 2H), 1.96 (m, 4H), 2.15 (s, 3H), 2.24 (t, 2H), 2.37 (m, 1H), 2.79 (d, 2H), 3.85 (s, 3H), 4.36 (t, 2H), 6.92 (d, 1H), 7.02 (d, 2H), 7.23-7.43 (m, 6H), 7.68 (d, 2H), 7.71 (dd, 1H); MS (m/e, M$^+$): 482

Example 20

2-(4-isopropylphenyl)-1-{3-[4-(3-acetylaminophenyl)piperidin-1-yl]propyl}-1H-benzimidazole 114 mg (yield 55%) of the title compound was obtained by repeating the procedure of Example 9 except for using 100 mg (0.42 mmol) of 2-(4-isopropylphenyl)-1H-benzimidazole.

$^1$H NMR (300 MHz, CDCl$_3$) δ 1.27 (d, 3H), 1.29 (d, 3H), 1.63 (m, 2H), 1.74 (m, 2H), 1.94 (m, 4H), 2.14 (s, 3H), 2.30 (t, 2H), 2.54 (m, 1H), 2.84 (brd, 2H), 2.97 (m, 1H), 4.36 (t, 2H), 6.93 (d, 1H), 7.23-7.38 (m, 6H), 7.44 (m, 1H), 7.47 (s, 1H), 7.65 (d, 2H), 7.80 (m, 1H); MS (m/e, M$^+$): 492

Example 21

2-phenyl-1-{3-[4-(3-acetylaminophenyl)piperidin-1-yl]propyl}-5,6-dimethyl-1H-benzimidazole 123 mg (yield 57%) of the title compound was obtained by repeating the procedure of Example 9 except for using 100 mg (0.45 mmol) of 2-phenyl-5,6-dimethyl-1H-benzimidazole.

$^1$H NMR (300 MHz, CDCl$_3$) δ 1.65 (m, 2H), 1.70 (m, 2H), 1.91 (m, 4H), 2.10 (s, 3H), 2.26 (t, 2H), 2.38 (s, 3H), 2.40 (s, 3H), 2.45 (m, 1H), 2.80 (brd, 2H), 4.29 (t, 2H), 6.92 (d, 1H), 7.19 (dd, 2H), 7.32 (d, 1H), 7.41 (s, 1H), 7.47 (m, 3H), 7.56 (s, 1H), 7.71 (dd, 2H), 7.95 (s, 1H); MS (m/e, M$^+$): 480

Example 22

2-(4-chlorophenyl)-1-{3-[4-(3-acetylaminophenyl)piperidin-1-yl]propyl}-5,6-dimethyl-1H-benzimidazole 118 mg (yield 59%) of the title compound was obtained by repeating the procedure of Example 9 except for using 100 mg (0.39 mmol) of 2-(4-chlorophenyl)-5,6-dimethyl-1H-benzimidazole.

$^1$H NMR (300 MHz, CDCl$_3$) δ 1.58 (m, 2H), 1.74 (m, 2H), 1.92 (m, 4H), 2.13 (s, 3H), 2.24 (t, 2H), 2.38 (s, 3H), 2.40 (s, 3H), 2.46 (m, 1H), 2.79 (brd, 2H), 4.30 (t, 2H), 6.93 (d, 1H), 7.22 (d, 2H), 7.33 (s, 1H), 7.35 (d, 1H), 7.46 (s, 2H), 7.55 (s, 1H), 7.66 (d, 3H): MS (m/e, M$^+$): 515

Example 23

2-phenyl-1-{3-[4-(3-acetylaminophenyl)piperidin-1-yl]propyl}-6-methyl-1H-benzimidazole 103 mg (yield 46%) of the title compound was obtained by repeating the procedure of Example 9 except for using 100 mg (0.48 mmol) of 2-phenyl-5-methyl-1H-benzimidazole.

$^1$H NMR (300 MHz, CDCl$_3$) δ 1.60-1.74 (m, 4H), 1.89-1.98 (m, 4H), 2.14 (m, 3H), 2.27 (t, 2H), 2.42 (m, 1H), 2.49 (s, 3H), 2.84 (br-d, 2H), 4.32 (t, 2H), 6.95 (d, 1H), 7.13 (m, 1H), 7.23-7.40 (m, 5H), 7.49-7.59 (m, 4H), 7.70-7.74 (m, 3H); MS (m/e, M+): 466, 438, 360, 291, 250, 231

Example 24

2-(4-chlorophenyl)-1-{3-[4-(3-acetylaminophenyl)piperidin-1-yl]propyl}-6-methyl-1H-benzimidazole 101 mg (yield 49%) of the title compound was obtained by repeating the procedure of Example 9 except for using 100 mg (0.41 mmol) of 2-(4-chlorophenyl)-5-methyl-1H-benzimidazole.
$^1$H NMR (300 MHz, CDCl$_3$) δ 1.61 (m, 2H), 1.73 (m, 2H), 1.92 (m, 4H), 2.14 (s, 3H), 2.23 (t, 2H), 2.45 (m, 1H), 2.49 (s, 3H), 2.51 (s, 3H), 2.81 (brd, 2H), 4.31 (t, 2H), 6.92 (brd, 1H), 7.13 (dd, 1H), 7.23 (d, 2H), 7.35 (dd, 2H), 7.48 (d, 2H), 7.59 (s, 1H), 7.67 (d, 3H): MS (m/e, M+): 501

Example 25

2-(4-chlorophenyl)-1-{3-[4-(3-acetylaminophenyl)piperidin-1-yl]propyl}-6-chloro-1H-benzimidazole 109 mg (yield 55%) of the title compound was obtained by repeating the procedure of Example 9 except for using 100 mg (0.38 mmol) of 2-(4-chlorophenyl)-5-chloro-1H-benzimidazole.
$^1$H NMR (300 MHz, CDCl$_3$) δ 1.55 (m, 2H), 1.74 (m, 2H), 1.92 (m, 4H), 2.16 (s, 3H), 2.23 (t, 2H), 2.42 (m, 1H), 2.76 (d, 2H), 4.35 (t, 2H), 6.95 (d, 1H), 7.24-7.41 (m, 6H), 7.50 (d, 2H), 7.69 (d, 2H), 7.77 (d, 1H): MS (m/e, M+): 521

Example 26

2-phenyl-1-{3-[4-(3-acetylaminophenyl)piperidin-1-yl]propyl}-6-fluoro-1H-benzimidazole 121 mg (yield 55%) of the title compound was obtained by repeating the procedure of Example 9 except for using 100 mg (0.47 mmol) of 2-phenyl-5-fluoro-1H-benzimidazole.
$^1$H NMR (300 MHz, CDCl$_3$) δ 1.62 (m, 2H), 1.74 (m, 2H), 1.92 (m, 4H), 2.15 (s, 3H), 2.26 (t, 2H), 2.42 (d, 2H), 4.34 (t, 2H), 6.87 (d, 1H), 7.03 (dd, 1H), 7.21-7.53 (m, 9H), 7.70-7.74 (m, 2H): MS (m/e, M+): 470

Example 27

2-phenyl-1-{3-[4-(3-acetylaminophenyl)piperidin-1-yl]propyl}-6-methoxy-1H-benzimidazole 114 mg (yield 53%) of the title compound was obtained by repeating the procedure of Example 9 except for using 100 mg (0.45 mmol) of 2-phenyl-5-methoxy-1H-benzimidazole.
$^1$H NMR (300 MHz, CDCl$_3$) δ 1.62 (m, 4H), 1.91 (m, 4H), 2.18 (s, 3H), 2.25 (t, 2H), 2.39 (m, 1H), 2.82 (brd, 2H), 3.88 (d, 3H), 4.33 (t, 2H), 6.90-6.94 (m, 2H), 7.22-7.33 (m, 4H), 7.49 (m, 3H), 7.67-7.73 (m, 3H): MS (m/e, M+): 482

Example 28

2-(4-chlorophenyl)-1-{3-[4-(3-acetylaminophenyl)piperidin-1-yl]propyl}-6-methoxy-1H-benzimidazole 108 mg (yield 54%) of the title compound was obtained by repeating the procedure of Example 9 except for using 100 mg (0.38 mmol) of 2-(4-chlorophenyl)-5-methoxy-1H-benzimidazole.
$^1$H NMR (300 MHz, CDCl$_3$) δ 1.76 (m, 4H), 1.91 (m, 4H), 2.18 (s, 3H), 2.25 (t, 2H), 2.39 (m, 1H), 2.82 (brd, 2H), 3.89 (d, 3H), 4.33 (t, 2H), 6.93-6.98 (m, 2H), 7.28-7.38 (m, 5H), 7.51 (d, 2H), 7.71 (m, 2H): MS (m/e, M+): 517

Example 29

2-phenyl-1-{3-[4-(3-acetylaminophenyl)piperidin-1-yl]propyl}-6-chloro-1H-benzimidazole 106 mg (yield 51%) of the title compound was obtained by repeating the procedure of Example 9 except for using 100 mg (0.43 mmol) of 2-phenyl-5-chloro-1H-benzimidazole.
$^1$H NMR (300 MHz, CDCl$_3$) δ NMR (300 MHz, CDCl$_3$) δ 1.65-1.81 (m, 4H), 1.90-2.00 (m, 4H), 2.15 (s, 3H), 2.25 (t, 2H), 2.45 (m, 1H), 2.82 (br-d, 2H), 4.30 (t, 2H), 6.92 (d, 1H, J=6.8 Hz), 7.24-7.53 (m, 9H), 7.69-7.79 (m, 3H); MS (m/e, M+): 487

Example 30

2-(4-fluorophenyl)-1-{3-[4-(3-acetylaminophenyl)piperidin-1-yl]propyl}-6-chloro-1H-benzimidazole 70 mg (yield 35%) of the title compound was obtained by repeating the procedure of Example 9 except for using 100 mg (0.40 mmol) of 2-(4-fluorophenyl)-5-chloro-1H-benzimidazole.
$^1$H NMR (300 MHz, CDCl$_3$) δ 1.61 (m, 2H), 1.75 (m, 2H), 1.89-1.97 (m, 4H), 2.17 (s, 3H), 2.26 (t, 2H), 2.45 (m, 1H), 2.80 (br-d, 2H), 4.32 (t, 2H), 6.95 (d, 1H), 7.21-7.38 (m, 7H), 7.69-7.78 (m, 3H); MS (m/e, M+): 504

Example 31

2-(4-chlorophenyl)-1-{3-[4-(3-acetylaminophenyl)piperidin-1-yl]propyl}-6-fluoro-1H-benzimidazole 67 mg (yield 33%) of the title compound was obtained by repeating the procedure of Example 9 except for using 100 mg (0.40 mmol) of 2-(4-chlorophenyl)-5-chloro-1H-benzimidazole.
$^1$H NMR (300 MHz, CDCl$_3$) δ 1.60 (m, 2H), 1.75 (m, 2H), 1.89-1.97 (m, 4H), 2.17 (s, 3H), 2.25 (t, 2H), 2.44 (m, 1H), 2.80 (br-d, 2H), 4.32 (t, 2H), 6.97 (d, 1H), 7.05 (m, 1H), 7.15-7.40 (m, 5H), 7.51 (d, 2H), 7.68 (d, 2H); MS (m/e, M+): 505

Example 32

2-phenyl-1-{3-[4-(3-acetylaminophenyl)piperidin-1-yl]propyl}-6-nitro-1H-benzimidazole 86 mg (yield 43%) of the title compound was obtained by repeating the procedure of Example 9 except for using 100 mg (0.42 mmol) of 2-phenyl-5-nitro-1H-benzimidazole.
$^1$H NMR (300 MHz, CDCl$_3$) δ 1.55 (m, 2H), 1.72 (m, 2H), 1.87-1.97 (m, 4H), 2.19 (s, 3H), 2.26 (t, 2H), 2.41 (m, 1H), 2.76 (br-d, 2H), 4.45 (t, 2H), 6.92 (d, 1H), 7.24-7.32 (m, 3H), 7.38 (s, 1H, NH), 7.57-7.59 (m, 4H), 7.76 (m, 2H), 8.25 (dd, 1H), 8.72 (d, 1H); MS (m/e, M+): 483

Example 33

2-(2-fluorophenyl)-1-{3-[4-(3-acetylaminophenyl) piperidin-1-yl]propyl}-6-chloro-1H-benzimidazole 110 mg (yield 56%) of the title compound was obtained by repeating the procedure of Example 9 except for using 100 mg (0.40 mmol) of 2-(2-s fluorophenyl)-5-chloro-1H-benzimidazole.

$^1$H NMR (300 MHz, CDCl$_3$) δ 1.62 (m, 2H), 1.71 (m, 2H), 1.85-1.93 (m, 4H), 2.15 (s, 3H), 2.20 (t, 2H), 2.42 (m, 1H), 2.76 (br, 2H), 4.23 (t, 2H), 6.94 (d, 1H), 7.24-7.80 (m, 11H); MS (m/e, M+): 504, 288, 257, 231

Example 34

2-(3-fluorophenyl)-1-{3-[4-(3-acetylaminophenyl) piperidin-1-yl]propyl}-6-chloro-1H-benzimidazole 108 mg (yield 54%) of the title compound was obtained by repeating the procedure of Example 9 except for using 100 mg (0.40 mmol) of 2-(3-fluorophenyl)-5-chloro-1H-benzimidazole.

$^1$H NMR (300 MHz, CDCl$_3$) δ 1.64 (m, 2H), 1.77 (m, 2H), 1.87-1.95 (m, 4H), 2.17 (s, 3H), 2.26 (t, 2H), 2.42 (m, 1H), 2.82 (br, 2H), 4.35 (t, 2H), 6.94 (d, 1H), 7.25-7.79 (m, 11H); MS (m/e, M+): 504, 476, 380, 329, 288, 257, 231

Example 35

2-(3-chlorophenyl)-1-{3-[4-(3-acetylaminophenyl) piperidin-1-yl]propyl}-6-chloro-1H-benzimidazole 100 mg (yield 51%) of the title compound was obtained by repeating the procedure of Example 9 except for using 100 mg (0.38 mmol) of 2-(3-chlorophenyl)-5-chloro-1H-benzimidazole.

$^1$H NMR (300 MHz, CDCl$_3$) δ 1.61-1.75 (m, 4H), 1.88-1.96 (m, 4H), 2.17 (s, 3H), 2.26 (t, 2H), 2.42 (m, 1H), 2.81 (brd, 2H), 4.35 (t, 2H), 6.96 (d, 1H), 7.25-7.79 (m, 11H); MS (m/e, M+): 520, 492, 409, 380, 302, 257, 231

Example 36

2-(4-chlorophenyl)-1-{3-[4-(3-acetylaminophenyl) piperidin-1-yl]propyl}-6-bromo-1H-benzimidazole 92 mg (yield 50%) of the title compound was obtained by repeating the procedure of Example 9 except for using 100 mg (0.32 mmol) of 2-(4-chlorophenyl)-5-bromo-1H-benzimidazole.

$^1$H NMR (300 MHz, CDCl$_3$) δ 1.60-1.77 (m, 4H), 1.88-1.98 (m, 4H), 2.16 (s, 3H), 2.23 (t, 2H), 2.42 (m, 1H), 2.80 (brd, 2H), 4.34 (t, 2H), 6.96 (d, 1H), 7.23-7.43 (m, 6H), 7.50 (d, 2H), 7.64 (m, 1H), 7.69 (d, 2H); MS (m/e, M+): 566, 536, 485, 348, 257, 231

Example 37

2-(2-chlorophenyl)-1-{3-[4-(3-acetylaminophenyl) piperidin-1-yl]propyl}-5,6-dimethyl-1H-benzimidazole 106 mg (yield 53%) of the title compound was obtained by repeating the procedure of Example 9 except for using 100 mg (0.39 mmol) of 2-(2-chlorophenyl)-5,6-dimethyl-1H-benzimidazole.

$^1$H NMR (300 MHz, CDCl$_3$) δ 1.58-1.75 (m, 4H), 1.82-1.91 (m, 4H), 2.14 (s, 3H), 2.21 (t, 2H), 2.38 (m, 1H), 2.39 (s, 3H), 2.42 (s, 3H), 2.76 (br, 2H), 4.10 (t, 2H), 6.94 (d, 1H), 7.22-7.30 (m, 3H), 7.39-7.58 (m, 7H); MS (m/e, M+): 514, 499, 479, 374, 339, 283, 231

Example 38

2-(3-chlorophenyl)-1-{3-[4-(3-acetylaminophenyl) piperidin-1-yl]propyl}-5,6-dimethyl-1H-benzimidazole 110 mg (yield 55%) of the title compound was obtained by repeating the procedure of Example 9 except for using 100 mg (0.39 mmol) of 2-(3-chlorophenyl)-5,6-dimethyl-1H-benzimidazole.

$^1$H NMR (300 MHz, CDCl$_3$) δ 1.62-1.78 (m, 4H), 1.90-1.98 (m, 4H), 2.16 (s, 3H), 2.27 (t, 2H), 2.38 (m, 1H), 2.39 (s, 3H), 2.42 (s, 3H), 2.84 (br, 2H), 4.32 (t, 2H), 6.94 (d, 1H), 7.23-7.46 (m, 7H), 7.56 (s, 1H), 7.61 (m, 1H), 7.76 (s, 1H); MS (m/e, M+): 514

Example 39

2-(4-chlorophenyl)-1-{3-[4-(3-acetylaminophenyl) piperidin-1-yl]propyl}-4,5-dimethyl-1H-benzimidazole 90 mg (yield 45%) of the title compound was obtained by repeating the procedure of Example 9 except for using 100 mg (0.39 mmol) of 2-(3-chlorophenyl)-4,5-dimethyl-1H-benzimidazole.

$^1$H NMR (300 MHz, CDCl$_3$) δ 1.58-1.78 (m, 4H), 1.88-1.96 (m, 4H), 2.16 (s, 3H), 2.24 (t, 2H), 2.41 (s, 3H), 2.43 (m, 1H), 2.62 (s, 3H), 2.82 (br, 2H), 4.28 (t, 2H), 6.94 (d, 1H), 7.11-7.35 (m, 6H), 7.48 (d, 2H), 7.68 (d, 2H); MS (m/e, M+): 514, 486, 403, 339, 298, 257, 231

Example 40

2-(2-chlorophenyl)-1-{3-[4-(3-acetylaminophenyl) piperidin-1-yl]propyl}-5-nitro-1H-benzimidazole 83 mg (yield 43%) of the title compound was obtained by repeating the procedure of Example 9 except for using 100 mg (0.36 mmol) of 2-(2-chlorophenyl)-5-nitro-1H-benzimidazole.

$^1$H NMR (300 MHz, CDCl$_3$) δ 1.60-1.80 (m, 4H), 1.83-1.92 (m, 4H), 2.19 (s, 3H), 2.23 (t, 2H), 2.40 (m, 1H), 2.74 (brd, 2H), 4.27 (t, 2H), 6.94 (d, 1H), 7.23-7.63 (m, 8H), 7.63 (d, 1H), 8.28 (dd, 1H), 8.58 (d, 1H); MS (m/e, M+): 532

Example 41

2-(3-chlorophenyl)-1-{3-[4-(3-acetylaminophenyl) piperidin-1-yl]propyl}-5-nitro-1H-benzimidazole 80 mg (yield 41%) of the title compound was obtained by repeating the procedure of Example 9 except for using 100 mg (0.36 mmol) of 2-(3-chlorophenyl)-5-nitro-1H-benzimidazole.

$^1$H NMR (300 MHz, CDCl$_3$) δ 8.75 (d, 1H), 8.29 (dd, 1H), 7.63~7.23 (m, 8H), 7.15 (d, 1H), 6.94 (dd, 1H), 4.27 (t, 2H), 2.74 (brd, 2H), 2.41 (m, 1H), 2.22 (t, 2H), 2.19 (s, 3H), 1.89~1.96 (m, 4H), 1.57~1.80 (m, 4H); MS (m/e, M+): 532

Example 42

2-(4-chlorophenyl)-1-{3-[4-(3-acetylaminophenyl) piperidin-1-yl]propyl}-5-nitro-1H-benzimidazole 57 mg (yield 30%) of the title compound was obtained by repeating the procedure of Example 9 except for using 100 mg (0.36 mmol) of 2-(4-chlorophenyl)-5-nitro-1H-benzimidazole.
$^1$H NMR (300 MHz, CDCl$_3$) δ 8.73 (d, 1H), 8.29 (dd, 1H), 8.03 (d, 1H), 7.73~7.51 (m, 4H), 7.34~7.20 (m, 4H), 6.94 (dd, 1H), 4.27 (t, 2H), 2.74 (brd, 2H), 2.41 (m, 1H), 2.22 (t, 2H), 2.19 (s, 3H), 1.89~1.96 (m, 4H), 1.57~1.80 (m, 4H); MS (m/e, M+): 532

Example 43

2-phenyl-1-{3-[4-(3-acetylaminophenyl)piperidin-1-yl]propyl}-5-bromo-1H-benzimidazole 97 mg (yield 50%) of the title compound was obtained by repeating the procedure of Example 9 except for using 100 mg (0.36 mmol) of 2-phenyl-5-bromo-1H-benzimidazole.
$^1$H NMR (300 MHz, CDCl$_3$) δ 7.75 (m, 3H), 7.68 (m, 3H), 7.22~7.43 (m, 6H), 6.96 (d, 1H), 4.35 (t, 2H), 2.81 (brd, 2H), 2.43 (m, 1H), 2.25 (t, 2H), 2.19 (s, 3H), 1.89~1.96 (m, 4H), 1.66~1.80 (m, 4H); MS (m/e, M+): 531

Example 44

2-(2,3,4,5-tetrafluorophenyl)-1-{3-[4-(3-acetylaminophenyl)piperidin-1-yl]propyl}-1H-benzimidazole 92 mg (yield 47%) of the title compound was obtained by repeating the procedure of Example 9 except for using 100 mg (0.37 mmol) of 2-(2,3,4,5-tetrafluorophenyl)-1H-benzimidazole.
$^1$H NMR (300 MHz, CDCl$_3$) δ 7.85 (m, 1H), 7.53 (m, 1H), 7.19~7.51 (m, 7H), 6.94 (d, 1H), 4.27 (t, 2H), 2.80 (brd, 2H), 2.42 (m, 1H), 2.22 (t, 2H), 2.19 (s, 3H), 1.89~1.96 (m, 4H), 1.57~1.80 (m, 4H); MS (m/e, M+): 524

Example 45

2-(4-trifluoromethylphenyl)-1-{3-[4-(3-acetylaminophenyl)piperidin-1-yl]propyl}-1H-benzimidazole 103 mg (yield 52%) of the title compound was obtained by repeating the procedure of Example 9 except for using 100 mg (0.38 mmol) of 2-(4-trifluoromethylphenyl)-1H-benzimidazole.
$^1$H NMR (300 MHz, CDCl$_3$) δ 1.53-1.64 (m, 2H), 1.75 (m, 2H), 1.89-2.02 (m, 4H), 2.14 (s, 3H), 2.26 (br t, 2H, J=6.4 Hz), 2.41 (m, 1H), 2.80 (m, 2H), 4.39 (br t, 2H, J=7.1 Hz), 6.92 (m, 1H), 7.22 (t, 1H, J=7.7 Hz), 7.32-7.38 (m, 4H), 7.50 (m, 1H), 7.68 (br s, 1H), 7.79 (d, 2H, J=8.0 Hz), 7.83 (m, 1H), 7.91 (d, 2H, J=8.2 Hz); MS (m/e, M+): 520 (M+), 231

Example 46

2-(4-biphenyl)-1-{3-[4-(3-acetylaminophenyl)piperidin-1-yl]propyl}-1H-benzimidazole 105 mg (yield 54%) of the title compound was obtained by repeating the procedure of Example 9 except for using 100 mg (0.37 mmol) of 2-(4-biphenyl)-1H-benzimidazole.
$^1$H NMR (300 MHz, CDCl$_3$) δ 1.59-1.75 (m, 4H), 1.89-2.03 (m, 4H), 2.21 (s, 3H), 2.30 (m, 2H), 2.40 (m, 1H), 2.83 (m, 2H), 4.42 (m, 2H), 6.89 (m, 1H), 7.17 (m, 1H), 7.26-7.47 (m, 8H), 7.57 (br s, 1H), 7.63 (m, 2H), 7.75 (m, 2H), 7.83 (m, 3H); MS (m/e, M+): 528 (M+), 297, 231, 70

Example 47

2-(4-phenoxyphenyl)-1-{3-[4-(3-acetylaminophenyl) piperidin-1-yl]propyl}-1H-benzimidazole 95 mg (yield 50%) of the title compound was obtained by repeating the procedure of Example 9 except for using 100 mg (0.35 mmol) of 2-(4-phenoxyphenyl)-1H-benzimidazole.
$^1$H NMR (300 MHz, CDCl$_3$) δ 1.67 (m, 2H), 1.76 (m, 2H), 1.90-2.03 (m, 4H), 2.12 (s, 3H), 2.28 (br t, 2H, J=6.6 Hz), 2.43 (m, 1H), 2.84 (m, 2H), 4.38 (br t, 2H, J=7.2 Hz), 6.95 (m, 1H), 7.04-7.40 (m, 12H), 7.47 (m, 1H), 7.53 (m, 1H), 7.72 (m, 2H), 7.81 (m, 1H); MS (m/e, M+): 544 (M+), 327, 231, 70

Example 48

2-(4-fluorophenyl)-1-{3-[4-(3-acetylaminophenyl) piperidin-1-yl]propyl}-1H-benzimidazole 98 mg (yield 44%) of the title compound was obtained by repeating the procedure of Example 9 except for using 100 mg (0.47 mmol) of 2-(4-fluorophenyl)-1H-benzimidazole.
$^1$H NMR (300 MHz, CDCl$_3$) δ 7.73~7.83 (m, 2H), 7.20~7.73 (m, 10H), 6.96 (d, 1H), 4.35 (t, 2H), 2.81 (brd, 2H), 2.43 (m, 1H), 2.25 (t, 2H), 2.19 (s, 3H), 1.88~1.96 (m, 4H), 1.55~1.78 (m, 4H); MS (m/e, M+): 470

Example 49

2-(4-chlorophenyl)-1-{3-[4-(3-acetylaminophenyl) piperidin-1-yl]propyl}-4,6-dimethyl-1H-benzimidazole 100 mg (yield 43%) of the title compound was obtained by repeating the procedure of Example 9 except for using 100 mg (0.45 mmol) of 2-(3-chlorophenyl)-4,6-dimethyl-1H-benzimidazole.
$^1$H NMR (300 MHz, CDCl$_3$) δ 1.58-1.79 (m, 4H), 1.87-1.96 (m, 4H), 2.16 (s, 3H), 2.24 (t, 2H), 2.43 (m, 1H), 2.48 (s, 3H), 2.65 (s, 3H), 2.80 (br, 2H), 4.27 (t, 2H), 6.93 (s, 1H), 6.94 (d, 1H), 7.08 (s, 1H), 7.24-7.37 (m, 4H), 7.47 (d, 2H), 7.47 (d, 2H); MS (m/e, M+): 514

Example 50

2-(3,4-difluorophenyl)-1-{3-[4-(3-acetylaminophenyl)piperidin-1-yl]propyl}-1H-benzimidazole 107 mg (yield 51%) of the title compound was obtained by repeating the procedure of Example 9 except for using 100 mg (0.43 mmol) of 2-(3,4-difluorophenyl)-1H-benzimidazole.
$^1$H NMR (300 MHz, CDCl$_3$) δ 1.64 (m, 2H), 1.76 (brd, 2H), 1.90-2.04 (m, 4H), 2.17 (s, 3H), 2.27 (t, 2H), 2.44 (m, 1H), 2.82 (br, 2H), 4.38 (t, 2H), 6.94 (d, 1H), 7.24-7.38 (m, 7H), 7.45-7.59 (m, 2H), 7.65 (m, 1H), 7.80 (m, 1H); MS (m/e, M+): 488

Example 51

2-(4-cyanophenyl)-1-{3-[4-(3-acetylaminophenyl) piperidin-1-yl]propyl}-1H-benzimidazole 103 mg (yield 48%) of the title compound was obtained by repeating the procedure of Example 9 except for using 100 mg (0.45 mmol) of 2-(4-cyanophenyl)-1H-benzimidazole.

$^1$H NMR (300 MHz, CDCl$_3$) δ 1.43 (m, 2H), 1.71 (brd, 2H), 1.85-2.01 (m, 4H), 2.18 (s, 3H), 2.16 (t, 2H), 2.41 (m, 1H), 2.72 (br, 2H), 4.44 (t, 2H), 6.91 (d, 1H), 7.23-7.32 (m, 4H), 7.49-7.53 (m, 3H), 7.83 (m, 1H), 7.85 (d, 2H), 7.94 (d, 2H); MS (m/e, M+): 477

Example 52

2-(3-cyanophenyl)-1-{3-[4-(3-acetylaminophenyl) piperidin-1-yl]propyl}-1H-benzimidazole 96 mg (yield 45%) of the title compound was obtained by repeating the procedure of Example 9 except for using 100 mg (0.45 mmol) of 2-(3-cyanophenyl)-1H-benzimidazole.

$^1$H NMR (300 MHz, CDCl$_3$) δ 1.55 (m, 2H), 1.71 (brd, 2H), 1.86-1.99 (m, 4H), 2.17 (s, 3H), 2.24 (t, 2H), 2.41 (m, 1H), 2.72 (br, 2H), 4.43 (t, 2H), 6.92 (d, 1H), 7.24-7.49 (m, 7H), 7.67 (dd, 1H), 7.80 (m, 2H), 8.05-8.11 (m, 2H); MS (m/e, M$^+$): 477

Example 53

2-(4-chloro-2-fluorophenyl)-1-{3-[4-(3-acetylaminophenyl)piperidin-1-yl]propyl}-1H-benzimidazole 93 mg (yield 46%) of the title compound was obtained by repeating the procedure of Example 9 except for using 100 mg (0.40 mmol) of 2-(4-chloro-2-fluorophenyl)-1H-benzimidazole.

$^1$H NMR (300 MHz, CDCl$_3$) δ 1.60 (m, 2H), 1.74 (brd, 2H), 1.85-1.96 (m, 4H), 2.16 (s, 3H), 2.21 (t, 2H), 2.41 (m, 1H), 2.77 (br, 2H), 4.24 (t, 2H), 6.94 (d, 1H), 7.24-7.37 (m, 8H), 7.49 (d, 1H), 7.60 (dd, 1H), 7.82 (d, 1H); MS (m/e, M$^+$): 505

Example 54

2-(2-chloro-4-fluorophenyl)-1-{3-[4-(3-acetylaminophenyl)piperidin-1-yl]propyl}-1H-benzimidazole 86 mg (yield 43%) of the title compound was obtained by repeating the procedure of Example 9 except for using 100 mg (0.40 mmol) of 2-(2-chloro-4-fluorophenyl)-1H-benzimidazole.

$^1$H NMR (300 MHz, CDCl$_3$) δ 1.62 (m, 2H), 1.74 (brd, 2H), 1.84-1.94 (m, 4H), 2.16 (s, 3H), 2.23 (t, 2H), 2.42 (m, 1H), 2.78 (br, 2H), 4.16 (t, 2H), 6.95 (d, 1H), 7.16-7.37 (m, 8H), 7.52 (m, 2H), 7.82 (d, 1H); MS (m/e, M$^+$): 505

Example 55

2-(3-nitrophenyl)-1-{3-[4-(3-acetylaminophenyl) piperidin-1-yl]propyl}-1H-benzimidazole 97 mg (yield 47%) of the title compound was obtained by repeating the procedure of Example 9 except for using 100 mg (0.42 mmol) of 2-(3-nitrophenyl)-1H-benzimidazole.

$^1$H NMR (300 MHz, CDCl$_3$) δ 1.48 (m, 2H), 1.72 (brd, 2H), 1.88-2.04 (m, 4H), 2.19 (s, 3H), 2.27 (t, 2H), 2.41 (m, 1H), 2.78 (br, 2H), 4.45 (t, 2H), 6.89 (d, 1H), 7.24-7.39 (m, 5H), 7.51 (d, 1H), 7.75 (dd, 1H), 7.84 (d, 1H), 8.19 (d, 1H), 8.37 (d, 1H), 8.66 (s, 1H); MS (m/e, M$^+$): 497

Example 56

2-(5-chloro-2-methoxyphenyl)-1-{3-[4-(3-acetylaminophenyl)piperidin-1-yl]propyl}-1H-benzimidazole 62 mg (yield 31%) of the title compound was obtained by repeating the procedure of Example 9 except for using 100 mg (0.38 mmol) of 2-(5-chloro-2-methoxyphenyl)-1H-benzimidazole.

$^1$H NMR (300 MHz, CDCl$_3$) δ 1.68-1.82 (m, 4H), 1.84-2.03 (m, 4H), 2.17 (s, 3H), 2.35 (t, 2H), 2.38 (m, 1H), 2.88 (br, 2H), 3.70 (s, 3H), 4.06 (t, 2H), 6.95 (d, 1H), 6.99 (d, 1H), 7.23-7.47 (m, 7H), 7.58 (s, 1H), 7.80 (d, 1H); MS (m/e, M$^+$): 517

Example 57

2-(2-chloro-4-nitrophenyl)-1-{3-[4-(3-acetylaminophenyl)piperidin-1-yl]propyl}-1H-benzimidazole 96 mg (yield 50%) of the title compound was obtained by repeating the procedure of Example 9 except for using 100 mg (0.36 mmol) of 2-(2-chloro-4-nitrophenyl)-1H-benzimidazole.

$^1$H NMR (300 MHz, CDCl$_3$) δ 1.46 (m, 2H), 1.72 (brd, 2H), 1.84-1.94 (m, 4H), 2.17 (s, 3H), 2.18 (t, 2H), 2.41 (m, 1H), 2.88 (br, 2H), 4.20 (t, 2H), 6.87 (d, 1H), 7.16 (s, 1H), 7.23 (d, 1H), 7.35-7.42 (m, 4H) 7.52 (d, 1H), 7.79 (d, 1H), 7.85 (d, 1H), 8.30 (dd, 1H), 8.47 (s, 1H); MS (m/e, M$^+$): 532

Example 58

2-(2,4-dimethoxyphenyl)-1-{3-[4-(3-acetylaminophenyl)piperidin-1-yl]propyl}-1H-benzimidazole 54 mg (yield 27%) of the title compound was obtained by repeating the procedure of Example 9 except for using 100 mg (0.39 mmol) of 2-(2,4-dimethoxyphenyl)-1H-benzimidazole.

$^1$H NMR (300 MHz, CDCl$_3$) δ 1.66-1.82 (m, 4H), 1.84-1.99 (m, 4H), 2.16 (s, 3H), 2.34 (t, 2H), 2.36 (m, 1H), 2.89 (br, 2H), 3.67 (s, 3H), 3.87 (s, 3H), 4.04 (t, 2H), 6.60 (d, 1H, J=2.1 Hz), 6.64 (dd, 1H, J=8.4 Hz, 2.1 Hz), 6.97 (d, 1H), 7.21-7.42 (m, 6H), 7.50 (d, 1H, J=8.4 Hz), 7.78 (m, 1H); MS (m/e, M$^+$): 512

Example 59

2-(4-chloro-2-fluorophenyl)-1-{3-[4-(3-acetylaminophenyl)piperidin-1-yl]propyl}-5,6-dimethyl-1H-benzimidazole 92 mg (yield 48%) of the title compound was obtained by repeating the procedure of Example 9 except for using 100 mg (0.36 mmol) of 2-(4-chloro-2-fluorophenyl)-5,6-dimethyl-1H-benzimidazole.

$^1$H NMR (300 MHz, CDCl$_3$) δ 1.59 (m, 2H), 1.75 (brd, 2H), 1.86-1.94 (m, 4H), 2.16 (s, 3H), 2.20 (t, 2H), 2.39 (s, 3H), 2.41 (m, 1H), 2.42 (s, 3H), 2.80 (br, 2H), 4.18 (t, 2H), 6.92 (d, 1H), 7.16-7.34 (m, 4H), 7.37 (s, 1H), 7.46 (s, 1H), 7.57-7.63 (m, 2H); MS (m/e, M$^+$): 533

Example 60

2-(4-chlorophenyl)-1-{3-[4-(3-acetylaminophenyl) piperidin-1-yl]propyl}-4-carbamoyl-1H-benzimidazole 46 mg (yield 24%) of the title compound was obtained by repeating the procedure of Example 9 except for using 100 mg (0.37 mmol) of 2-(4-chlorophenyl)-4-carbamoyl-1H-benzimidazole.

$^1$H NMR (300 MHz, CDCl$_3$) δ 1.28 (m, 2H), 1.62 (brd, 2H), 1.72-1.91 (m, 4H), 2.21 (s, 3H), 2.22 (t, 2H), 2.33 (m, 1H), 2.65 (brd, 2H) 4.43 (t, 2H), 4.84 (brs, 1H, NH$_2$), 5.70 (brs, 1H, NH$_2$), 6.88 (d, 1H, J=7.8 Hz), 7.24 (m, 2H), 7.48 (d, 1H), 7.53 (d, 2H, J=8.7 Hz), 7.57 (m, 1H), 7.71 (d, 2H, J=8.7 Hz), 7.80 (s, 1H), 7.90 (dd, 1H, J=8.7 Hz, 1.5 Hz), 8.32 (d, 1H, J=1.5 Hz); MS (m/e, M$^+$): 530

Example 61

2-(4-chlorophenyl)-1-{3-[4-(3-acetylaminophenyl) piperidin-1-yl]propyl}-5-carbamoyl-1H-benzimidazole 49 mg (yield 25%) of the title compound was obtained by repeating the procedure of Example 9 except for using 100 mg (0.37 mmol) of 2-(4-chlorophenyl)-5-carbamoyl-1H-benzimidazole.

$^1$H NMR (300 MHz, CDCl$_3$) δ 1.61 (m, 2H), 1.72 (brd, 2H), 1.86-2.04 (m, 4H), 2.18 (s, 3H), 2.22 (t, 2H), 2.41 (m, 1H), 2.74 (br, 2H) 4.44 (t, 2H), 4.83 (brs, 1H, NH$_2$), 5.85 (brs, 1H, NH$_2$), 6.92 (d, 1H, J=7.4 Hz), 7.23 (dd, 1H), 7.36 (s, 1H), 7.43 (d, 1H, J=7.8 Hz), 7.54 (d, 2H, J=8.7 Hz), 7.69 (m, 2H), 7.49 (d, 2H, J=8.7 Hz), 7.80 (d, 1H, J=8.6 Hz), 8.30 (s, 1H); MS (m/e, M$^+$): 530

Example 62

2-(3-carbamoylphenyl)-1-{3-[4-(3-acetylaminophenyl)piperidin-1-yl]propyl}-1H-benzimidazole 95 mg (yield 46%) of the title compound was obtained by repeating the procedure of Example 9 except for using 100 mg (0.42 mmol) of 2-(3-carbamoylphenyl)-1H-benzimidazole.

$^1$H NMR (300 MHz, CDCl$_3$) δ 1.05 (m, 2H), 1.51 (brd, 2H), 1.68-1.82 (m, 4H), 1.97 (m, 2H), 2.23 (m, 1H), 2.25 (s, 3H), 2.51 (brd, 2H) 4.05 (t, 2H), 5.98 (brs, 1H, NH$_2$), 6.79 (d, 1H, J=7.5 Hz), 6.87 (s, 1H), 7.18 (dd, 1H), 7.35-7.37 (m, 3H), 7.55 (dd, 1H), 7.48 (d, 1H), 7.83-7.88 (m, 2H), 7.99 (s, 1H), 8.01 (d, 1H, J=8.1 Hz), 8.78 (s, 1H); MS (m/e, M$^+$): 495

Example 63

2-(2-hydroxyphenyl)-1-{3-[4-(3-acetylaminophenyl) piperidin-1-yl]propyl}-1H-benzimidazole 50 mg (yield 23%) of the title compound was obtained by repeating the procedure of Example 9 except for using 100 mg (0.47 mmol) of 2-(2-hydroxyphenyl)-1H-benzimidazole.

$^1$H NMR (300 MHz, CDCl$_3$) δ 1.72-1.84 (m, 4H), 2.04 (m, 2H), 2.18 (s, 3H), 2.24 (t, 2H), 2.51 (m, 1H), 2.70 (m, 2H), 3.13 (brd, 2H), 4.38 (t, 2H), 6.93 (d, 1H, J=8.4 Hz), 7.07-7.29 (m, 7H), 7.36-7.42 (m, 2H), 7.71 (m, 2H), 8.55 (d, 1H); MS (m/e, M$^+$): 468

Preparation of Imidazole Derivative

Examples 64 to 67

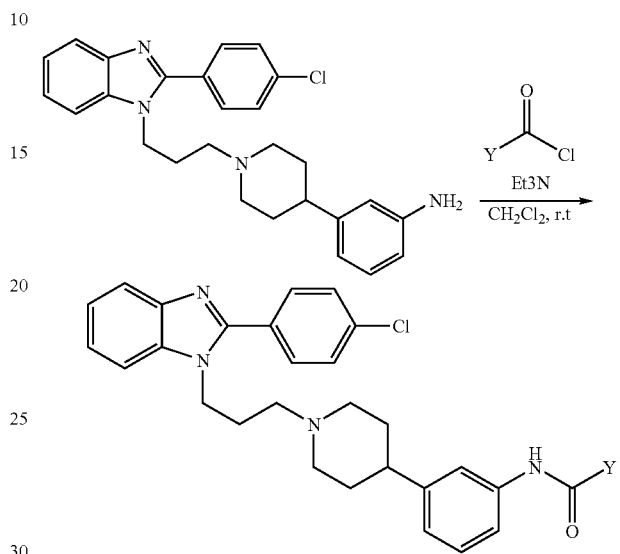

Example 64

2-(4-chlorophenyl)-1-{3-[4-(3-isobutyrylaminophenyl)piperidin-1-yl]propyl}-1H-benzimidazole Step 1) 2-(4-chlorophenyl)-1-{3-[4-(3-aminophenyl) piperidin-1-yl]propyl}-1H-benzimidazole

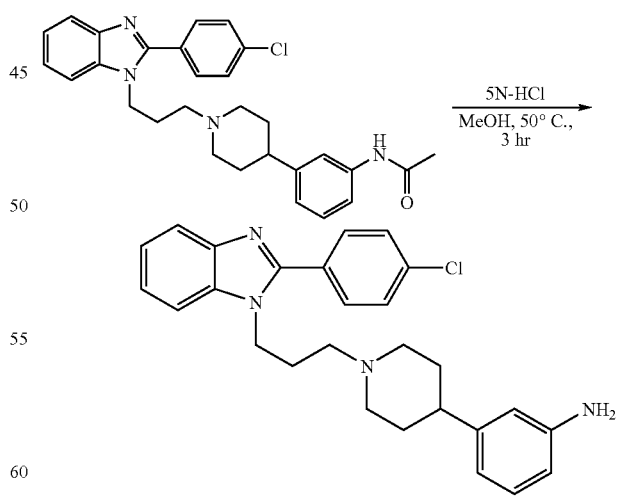

1.5 g (3.08 mmol) of 2-(4-chlorophenyl)-1-{3-[4-(3-acetylaminophenyl)piperidin-1-yl]propyl}-1H-benzimidazole obtained in Example 4 was dissolved in 30 ml of methanol, and 10 ml of 5N—HCl aqueous solution was added to the resulting solution, followed by mixing the solution at 50° C.

for 3 hours. The resulting solution was concentrated under a reduced pressure and 60 ml of water was added thereto. Then, pH of the solution was adjusted to 8 or more. The reaction mixture was extracted with ethylacetate (80 ml×2) being washed with water and a sodium hydroxide solution, and then the combined organic layer was dried over anhydrous sodium sulfate, and filtered. The solvent was removed under a reduced pressure, and the resulting residue was refined by silica gel column chromatography (n-hexane/ethylacetate=1/3) to obtain 1.19 g (yield 87%) of the title compound.

$^1$H NMR (300 MHz, CDCl$_3$) δ 1.62 (m, 2H), 1.74 (m, 2H), 1.88-1.99 (m, 4H), 2.25 (t, 2H), 2.35 (m, 1H), 2.82 (brs, 2H), 3.63 (brs, 2H, NH$_2$), 4.36 (t, 2H), 6.53 (m, 2H), 6.60 (d, 1H), 7.07 (dd, 1H), 7.29-7.33 (m, 2H), 7.47 (m, 1H), 7.52 (d, 2H), 7.71 (d, 1H), 7.81 (m, 1H); MS (m/e, M$^+$): 445

Step 2) 2-(4-chlorophenyl)-1-{3-[4-(3-isobutyrylaminophenyl)piperidin-1-yl]propyl}-1H-benzimidazole 70 g (0.157 mmol) of 2-(4-chlorophenyl)-1-{3-[4-(3-aminophenyl)piperidin-1-yl]propyl}-1H-benzimidazole obtained in the above step 1) was dissolved in 5 ml of dichloromethane, and 0.044 ml (0.31 mmol) of triethylamine and 0.02 ml (0.19 mmol) of isobutyrylchloride were slowly added to the resulting solution, followed by mixing the solution at room temperature for 1 hour. The reaction mixture was combined with 30 ml of water and extracted with dichloromethane (30 ml×2), and then the combined organic layer was dried over anhydrous sodium sulfate, and filtered. The solvent was removed under a reduced pressure, and the resulting residue was refined by silica gel column chromatography (5%-MeOH/CH$_2$Cl$_2$) to obtain 70 mg (yield 86%) of the title compound.

$^1$H NMR (300 MHz, CDCl$_3$) δ 1.71-1.85 (m, 4H), 1.97-2.06 (m, 4H), 2.17 (s, 3H), 2.34 (t, 2H), 2.48 (m, 1H), 2.65 (s, 3H), 2.95 (brd, 2H), 4.22 (t, 2H), 6.97 (d, 1H, J=7.5 Hz), 7.20-7.38 (m, 6H), 7.43 (brs, 1H, NH), 7.67 (m, 1H); MS (m/e, M$^+$): 515

Example 65

2-(4-chlorophenyl)-1-{3-[4-(3-benzoylaminophenyl)piperidin-1-yl]propyl}-1H-benzimidazole 77 mg (yield 90%) of the title compound was obtained by repeating the procedure of Example 64 except for using 70 mg (0.157 mmol) of 2-(4-chlorophenyl)-1-{3-[4-(3-aminophenyl)piperidin-1-yl]propyl}-1H-benzimidazole obtained in step 1) of Example 64, and 0.022 ml (0.19 mmol) of benzoylchloride.

$^1$H NMR (300 MHz, CDCl$_3$) δ 1.71 (t, 2H), 1.80 (d, 2H), 1.96 (m, 2H), 2.01 (m, 2H), 2.27 (t, 2H), 2.48 (m, 1H), 2.84 (br-d, 2H), 4.37 (t, J=14.4, 2H), 7.01 (d, J=7.5, 1H) 7.31 (m, 3H), 7.51 (m, 7H), 7.72 (d, 2H), 7.86 (m, 4H); MS (m/e, M$^+$): 549, 490, 443, 408

Example 66

2-(4-chlorophenyl)-1-{3-[4-(3-(3-chlorobenzoylamino)phenyl)piperidin-1-yl]propyl}-1H-benzimidazole 84 mg (yield 92%) of the title compound was obtained by repeating the procedure of Example 64 except for using 70 mg (0.157 mmol) of 2-(4-chlorophenyl)-1-{3-[4-(3-aminophenyl)piperidin-1-yl]propyl}-1H-benzimidazole obtained in step 1) of Example 64, and 0.024 ml (0.19 mmol) of 4-chlorobenzoylchloride.

$^1$H NMR (300 MHz, CDCl$_3$) δ 1.62 (m, 2H), 1.78 (d, 2H), 1.91 (m, 2H), 1.96 (m, 2H), 2.04 (s, 3H) 2.26 (t, 2H), 2.47 (m, 1H) 2.85 (br-d, 2H), 4.37 (t, J=14.7, 2H), 7.00 (d, J=37.8 Hz, 1H) 7.33 (m, 5H), 7.52 (m, 5H), 7.85 (m, 6H); MS (m/e, M$^+$): 584, 529, 475, 441

Example 67

2-(4-chlorophenyl)-1-{3-[4-(3-(4-methylbenzoylamino)phenyl)piperidin-1-yl]propyl}-1H-benzimidazole 77 mg (yield 87%) of the title compound was obtained by repeating the procedure of Example 64 except for using 70 mg (0.157 mmol) of 2-(4-chlorophenyl)-1-{3-[4-(3-aminophenyl)piperidin-1-yl]propyl}-1H-benzimidazole obtained in step 1) of Example 64, and 0.025 ml (0.19 mmol) of p-toluoylchloride.

$^1$H NMR (300 MHz, CDCl$_3$) δ 1.71 (m, 2H), 1.80 (m, 2H), 1.98 (m, 2H), 2.03 (m, 2H), 2.31 (t, 2H), 2.42 (s, 3H) 2.47 (m, 1H) 2.89 (br-d, 2H), 4.37 (t, J=14.7, 2H), 7.00 (d, 1H) 7.32 (m, 5H), 7.50 (m, 5H), 7.80 (m, 6H); MS (m/e, M$^+$): 563, 532, 499, 458

Preparation of Imidazole Derivative

Examples 68 to 70

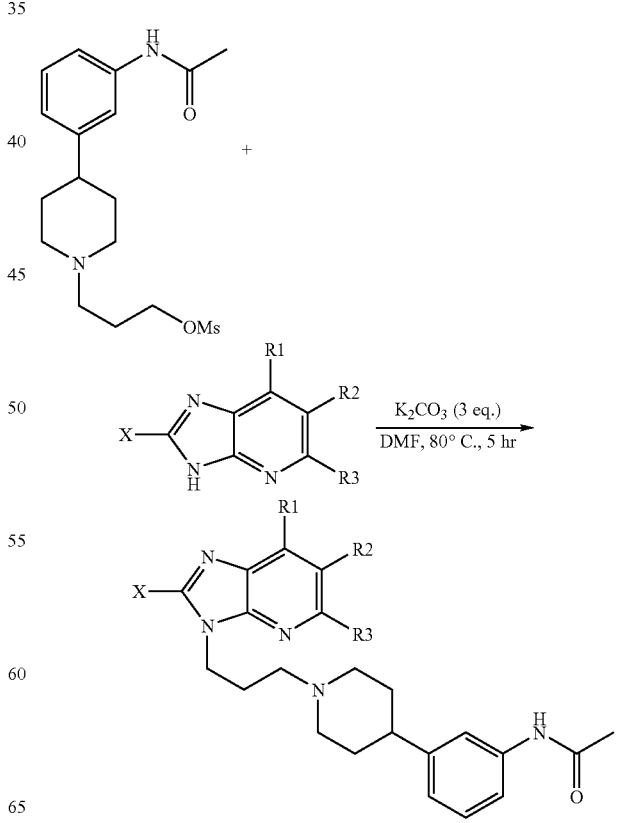

Example 68

6-bromo-5-methyl-2-phenyl-3-{3-[4-(3-acetylaminophenyl)piperidin-1-yl]propyl}-3H-imidazo[4,5-b]pyridine 100 mg (0.35 mmol) of 6-bromo-5-methyl-2-phenyl-3H-imidazo[4,5-b]pyridine was dissolved in 5 ml of N,N-dimethyl formamide, and 240 mg (0.68 mmol) of 3-[4-(3-acetylaminophenyl)piperidin-1-yl]propylmethanesulfonate obtained in Preparation Example 4 and 282 mg (2.04 mmol) of $K_2CO_3$ were added to the resulting solution, followed by mixing the solution at 80° C. for 5 hours. The reaction mixture was combined with 50 ml of water and extracted with ethylacetate (50 ml×2) being washed with water and a sodium hydroxide solution, and then the combined organic layer was dried over anhydrous sodium sulfate, and filtered. The solvent was removed under a reduced pressure, and the resulting residue was refined by silica gel column chromatography (5%-MeOH/$CH_2Cl_2$) to obtain 90 mg (yield 47%) of the title compound.

$^1$H NMR (300 MHz, $CDCl_3$) δ 1.57 (m, 2H), 1.72 (m, 2H), 2.01 (m, 2H), 2.17 (s, 3H), 2.35 (t, 2H), 2.37 (m, 1H), 2.77 (s, 3H), 2.84 (brd, 2H), 4.47 (t, 2H), 6.92 (d, 1H), 7.21-7.36 (m, 3H), 7.54 (t, 3H), 7.77 (t, 2H), 8.17 (s, 1H): MS (m/e, M$^+$): 546

Example 69

5-methyl-2-phenyl-3-{3-[4-(3-acetylaminophenyl)piperidin-1-yl]propyl}-3H-imidazo[4,5-b]pyridine 98 mg (yield 45%) of the title compound was obtained by repeating the procedure of Example 68 except for using 100 mg (0.47 mmol) of 5-methyl-2-phenyl-3H-imidazo[4,5-b]pyridine.

$^1$H NMR (300 MHz, $CDCl_3$) δ 1.59-1.75 (m, 4H), 1.90 (brt, 2H), 2.02 (m, 2H) 2.16 (s, 3H), 2.32 (t, 2H), 2.42 (m, 1H), 2.67 (s, 3H), 2.84 (br, 2H), 4.50 (t, 2H), 6.92 (d, 1H, J=7.2 Hz), 7.10 (d, 1H, J=8.1 Hz), 7.23-7.39 (m, 3H), 7.50-7.54 (m, 3H), 7.78 (m, 2H), 7.93 (d, 1H, J=8.1 Hz); MS (m/e, M$^+$): 467

Example 70

2-(benzo[1,3]dioxol-5-yl)-1-{3-[4-(3-acetylaminophenyl)piperidin-1-yl]propyl}-1H-benzimidazole 46 mg (yield 84%) of the title compound was obtained by repeating the procedure of Example 9 except for using 26.1 mg (0.11 mmol) of 2-(benzo[1,3]dioxol-5-yl)-1H-benzimidazole.

$^1$H NMR (300 MHz, $CDCl_3$) δ 1.61-1.78 (m, 4H), 1.89-2.01 (m, 4H), 2.15 (s, 3H), 2.28 (br t, 2H, J=6.6 Hz), 2.42 (m, 1H), 2.83 (m, 2H), 4.36 (br t, 2H, J=7.4 Hz), 6.02 (s, 2H), 6.95 (m, 2H), 7.20-7.38 (m, 7H), 7.45 (m, 1H), 7.71 (br s, 1H), 7.79 (m, 1H); MS (m/e, M$^+$): 496 (M$^+$), 265, 231, 70.

Preparation of Imidazole Derivative

Examples 71 and 87

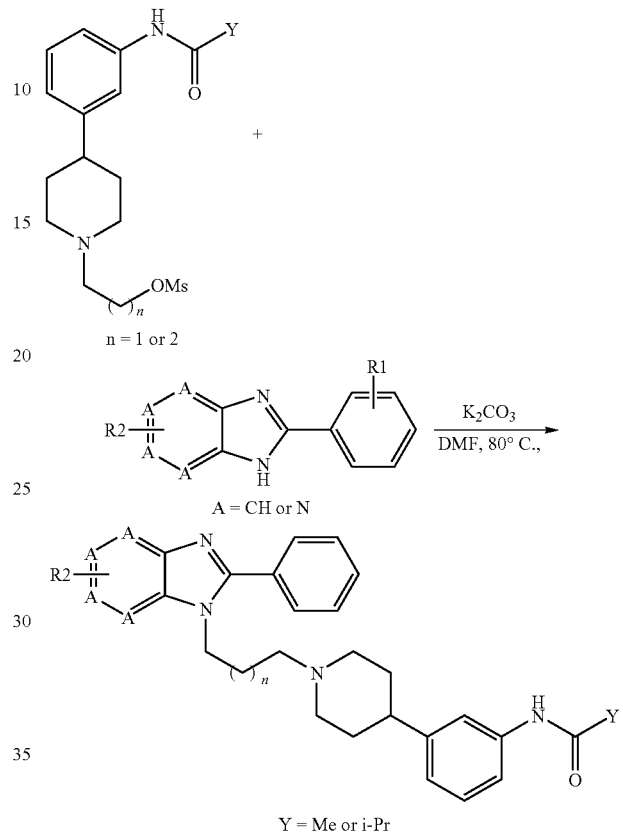

Example 71

2-(4-chlorophenyl)-1-{2-[4-(3-isobutyrylaminophenyl)piperidin-1-yl]ethyl}-1H-benzimidazole 45 mg (yield 31%) of the title compound was obtained by repeating the procedure of Example 1 except for using 115 mg (0.31 mmol) of 3-[4-(3-isoburyrylaminophenyl)piperidin-1-yl]ethylmethanesulfonate obtained by the procedure similar to Preparation Example 5, and 70 mg (0.31 mmol) of 2-(4-chlorophenyl)benzimidazole.

$^1$H NMR (300 MHz, $CDCl_3$) δ 1.25 (d, 6H), 1.52-1.86 (m, 4H), 2.12 (m, 2H), 2.46 (m, 1H), 2.52 (m, 1H), 2.79 (t, 2H), 2.86 (brd, 2H), 4.38 (t, 2H), 6.92 (d, 1H, J=7.2 Hz), 7.10 (s, 1H), 7.22-7.35 (m, 3H), 7.47 (m, 2H), 7.52 (d, 2H, J=8.4 Hz), 7.79 (d, 2H, J=8.4 Hz), 7.84 (m, 1H); MS (m/e, M$^+$): 500

Example 72

2-phenyl-3-{3-[4-(3-acetylaminophenyl)piperidin-1-yl]propyl}-3H-imidazo[4,5-c]pyridine 74 mg (yield 32%) of the title compound was obtained by repeating the procedure of Example 9 except for using 100 mg (0.51 mmol) of 2-phenyl-3H-imidazo[4,5-c]pyridine.

¹H NMR (300 MHz, CDCl₃) δ 1.64 (m, 2H), 1.78 (brd, 2H), 1.99 (brt, 2H), 2.17 (s, 3H), 2.36 (m, 1H), 2.37-2.48 (m, 4H), 2.94 (brd, 2H), 4.80 (t, 2H), 6.94 (d, 1H, J=7.6 Hz), 7.05 (dd, 1H), 7.25 (m, 1H), 7.35-7.50 (m, 5H), 7.74 (d, 2H, J=6.0 Hz), 8.18 (d, 1H, J=7.5 Hz), 8.50 (d, 2H); MS (m/e, M⁺): 453

Example 73

2-phenyl-3-{3-[4-(3-acetylaminophenyl)piperidin-1-yl]propyl}-3H-imidazo[4,5-d]pyridine 30 mg (yield 13%) of the title compound was obtained by repeating the procedure of Example 9 except for using 100 mg (0.51 mmol) of 2-phenyl-3H-imidazo[4,5-d]pyridine.

¹H NMR (300 MHz, CDCl₃) δ 1.57-1.75 (m, 4H), 1.93 (m, 2H), 2.07 (m, 2H), 2.17 (s, 3H), 2.34 (m, 1H), 2.41 (m, 2H), 2.83 (brd, 2H), 4.53 (t, 2H), 6.95 (d, 1H, J=7.6 Hz), 7.21-7.35 (m, 4H), 7.55 (m, 4H), 7.80 (m, 2H), 8.06 (d, 1H, J=8.1 Hz), 8.40 (d, 1H, J=4.8 Hz), 8.50 (d, 2H); MS (m/e, M⁺): 453

Example 74

5-bromo-6-methyl-2-phenyl-3-{3-[4-(3-acetylaminophenyl)piperidin-1-yl]propyl}-3H-imidazo[4,5-e]pyridine 15 mg (yield 8%) of the title compound was obtained by repeating the procedure of Example 9 except for using 100 mg (0.35 mmol) of 6-bromo-5-methyl-2-phenyl-3H-imidazo[4,5-b]pyridine.

¹H NMR (300 MHz, CDCl₃) δ 1.61 (m, 2H), 1.73 (brd, 2H), 1.86-2.03 (m, 4H), 2.16 (s, 3H), 2.22 (t, 2H), 2.39 (m, 1H), 2.78 (s, 3H), 2.83 (brd, 2H), 4.37 (t, 2H), 6.93 (d, 1H, J=7.5 Hz), 7.21-7.37 (m, 3H), 7.51-7.55 (m, 4H), 7.78 (m, 2H), 8.02 (s, 1H); MS (m/e, M⁺): 546

Example 75

6-methyl-2-phenyl-3-{3-[4-(3-acetylaminophenyl)piperidin-1-yl]propyl}-3H-imidazo[4,5-e]pyridine 13 mg (yield 6%) of the title compound was obtained by repeating the procedure of Example 9 except for using 100 mg (0.47 mmol) of 5-methyl-2-phenyl-3H-imidazo[4,5-b]pyridine.

¹H NMR (300 MHz, CDCl₃) δ 1.59-1.75 (m, 4H), 1.90 (brt, 2H), 2.02 (m, 2H) 2.16 (s, 3H), 2.32 (t, 2H), 2.42 (m, 1H), 2.68 (s, 3H), 2.84 (br, 2H), 4.39 (t, 2H), 6.92 (d, 1H, J=7.2 Hz), 7.23-7.39 (m, 3H), 7.50-7.54 (m, 4H), 7.70 (d, 1H, J=8.1 Hz), 7.78 (m, 2H); MS (m/e, M⁺): 467

Example 76

2-(3-methoxycarbonylphenyl)-1-{3-[4-(3-acetylaminophenyl)piperidin-1-yl]propyl}-1H-benzimidazole 85 mg (yield 43%) of the title compound was obtained by repeating the procedure of Example 9 except for using 100 mg (0.39 mmol) of 2-(3-methoxycarbonylphenyl)-1H-benzimidazole.

¹H NMR (300 MHz, CDCl₃) δ 1.41 (m, 2H), 1.66 (brd, 2H), 1.82-2.00 (m, 4H), 2.20 (t, 2H), 2.21 (s, 3H), 2.35 (m, 1H), 2.72 (brd, 2H), 3.95 (s, 3H), 4.44 (t, 2H), 6.89 (d, 1H, J=7.5 Hz), 7.10 (s, 1H), 7.23-7.35 (m, 3H), 7.48 (m, 2H), 7.63 (dd, 1H, J=7.5 Hz, 7.8 Hz), 7.78 (brs, 1H, NH), 7.82 (m, 1H), 8.00 (d, 1H, J=7.5 Hz), 8.20 (d, 1H, J=7.8 Hz), 8.44 (d, 1H, J=1.6 Hz); MS (m/e, M⁺): 510

Example 77

2-(4-ethylphenyl)-1-{3-[4-(3-acetylaminophenyl)piperidin-1-yl]propyl}-1H-benzimidazole 117 mg (yield 54%) of the title compound was obtained by repeating the procedure of Example 9 except for using 100 mg (0.45 mmol) of 2-(4-ethylphenyl)-1H-benzimidazole.

¹H NMR (300 MHz, CDCl₃) δ 1.27 (t, 3H), 1.68 (m, 4H), 1.98 (m, 4H), 2.16 (s, 3H), 2.30 (t, 2H), 2.40 (m, 1H), 2.72 (q, 2H), 2.83 (brd, 2H), 4.36 (t, 2H), 6.95 (d, 1H, J=7.5 Hz), 7.24-7.39 (m, 7H), 7.45 (m, 1H), 7.67 (d, 2H, J=8.1 Hz), 7.80 (m, 1H); MS (m/e, M⁺): 480

Example 78

2-(4-cyanophenyl)-1-{3-[4-(3-acetylaminophenyl)piperidin-1-yl]propyl}-5,6-dimethyl-1H-benzimidazole 113 mg (yield 56%) of the title compound was obtained by repeating the procedure of Example 9 except for using 100 mg (0.40 mmol) of 2-(4-cyanophenyl)-5,6-dimethyl-1H-benzimidazole.

¹H NMR (300 MHz, CDCl₃) δ 1.40-1.45 (m, 2H), 1.72 (m, 2H), 1.85-2.04 (m, 4H), 2.14 (t, 2H), 2.17 (s, 3H), 2.35 (m, 1H), 2.40 (s, 3H), 2.43 (s, 3H), 2.74 (brd, 2H), 4.38 (t, 2H), 6.91 (d, 1H, J=7.6 Hz), 7.17-7.28 (m, 2H), 7.47 (d, 1H, J=7.8 Hz), 7.60 (d, 2H, J=10.9 Hz), 7.78-7.85 (m, 2H), 7.92 (d, 2H, J=8.1 Hz); MS (m/e, M⁺): 505

Example 79

2-(m-tolyl)-1-{3-[4-(3-acetylaminophenyl)piperidin-1-yl]propyl}-1H-benzimidazole 132 mg (yield 59%) of the title compound was obtained by repeating the procedure of Example 9 except for using 100 mg (0.48 mmol) of 2-(m-tolyl)-1H-benzimidazole.

¹H NMR (300 MHz, CDCl₃) δ 1.67 (m, 4H), 1.96 (m, 4H), 2.15 (s, 3H), 2.29 (t, 2H), 2.43 (s, 3H) 2.84 (brd, 2H), 4.36 (t, 2H), 6.94 (d, 1H, J=7.5 Hz), 7.24 (m, 2H), 7.29-7.51 (m, 7H) 7.58 (s, 1H), 7.80 (d, 1H, J=4.2 Hz); MS (m/e, M⁺): 505

Example 80

2-(2-chloro-4-fluorophenyl)-1-{3-[4-(3-acetylaminophenyl)piperidin-1-yl]propyl}-5,6-dimethyl-1H-benzimidazole 86 mg (yield 45%) of the title compound was obtained by repeating the procedure of Example 9 except for using 100 mg (0.36 mmol) of 2-(2-chloro-4-fluorophenyl)-5,6-dimethyl-1H-benzimidazole.

¹H NMR (300 MHz, CDCl₃) δ 1.66-1.80 (m, 4H), 1.89-1.95 (m, 4H), 2.17 (s, 3H), 2.23 (t, 2H), 2.40 (s, 3H), 2.43 (s, 3H), 2.47 (m, 1H), 2.82 (brd, 2H), 4.10 (t, 2H), 6.96 (d, 1H, J=7.5 Hz), 7.16 (m, 1H), 7.24-7.32 (m, 4H), 7.37 (s, 1H), 7.51-7.58 (m, 2H); MS (m/e, M⁺): 533

Example 81

2-(4-chlorophenyl)-1-{3-[4-(3-acetylaminophenyl)piperidin-1-yl]propyl}-5-cyano-1H-benzimidazole 30 mg (yield 15%) of the title compound was obtained by repeating the procedure of Example 9 except for using 100 mg (0.39 mmol) of 2-(4-chlorophenyl)-5-cyano-1H-benzimidazole.

$^1$H NMR (300 MHz, CDCl$_3$) δ 1.57-1.73 (m, 4H), 1.80-2.03 (m, 4H), 2.18 (s, 3H), 2.20 (t, 2H), 2.44 (m, 1H), 2.78 (brd, 2H), 4.44 (t, 2H), 6.94 (d, 1H, J=7.2 Hz), 7.24 (m, 1H), 7.33 (s, 1H), 7.60 (m, 4H), 7.74 (d, 2H, J=8.4 Hz), 7.87 (d, 1H, J=8.4 Hz), 8.04 (s, 1H); MS (m/e, M$^+$): 512

Example 82

2-(4-chlorophenyl)-1-{3-[4-(3-acetylaminophenyl)piperidin-1-yl]propyl}-6-cyano-1H-benzimidazole 60 mg (yield 30%) of the title compound was obtained by repeating the procedure of Example 9 except for using 100 mg (0.39 mmol) of 2-(4-chlorophenyl)-6-cyano-1H-benzimidazole.

$^1$H NMR (300 MHz, CDCl$_3$) δ 1.57 (m, 2H), 1.75 (m, 2H), 1.88-1.95 (m, 4H), 2.19 (s, 3H), 2.21 (t, 2H), 2.41 (m, 1H), 2.78 (brd, 2H), 4.43 (t, 2H), 6.94 (d, 1H, J=7.2 Hz), 7.24 (m, 1H), 7.29 (m, 1H), 7.40 (s, 1H), 7.56 (m, 4H), 7.72 (d, 2H, J=8.4 Hz), 8.14 (s, 1H); MS (m/e, M$^+$): 512

Example 83

2-(4-chlorophenyl)-1-{3-[4-(3-acetylaminophenyl)piperidin-1-yl]propyl}-5-fluoro-1H-benzimidazole 32 mg (yield 16%) of the title compound was obtained by repeating the procedure of Example 9 except for using 100 mg (0.40 mmol) of 2-(4-chlorophenyl)-5-fluoro-1H-benzimidazole.

$^1$H NMR (300 MHz, CDCl$_3$) δ 1.60-1.80 (m, 4H), 1.90-1.98 (m, 4H), 2.18 (s, 3H), 2.24 (t, 2H), 2.45 (m, 1H), 2.81 (brd, 2H), 4.33 (t, 2H), 6.96 (d, 1H, J=7.5 Hz), 7.06 (m, 1H), 7.19-7.36 (m, 4H), 7.53 (m, 2H), 7.69-7.77 (m, 3H); MS (m/e, M$^+$): 505

Example 84

2-(4-fluorophenyl)-1-{3-[4-(3-acetylaminophenyl)piperidin-1-yl]propyl}-5-chloro-1H-benzimidazole 28 mg (yield 14%) of the title compound was obtained by repeating the procedure of Example 9 except for using 100 mg (0.40 mmol) of 2-(4-fluorophenyl)-5-chloro-1H-benzimidazole.

$^1$H NMR (300 MHz, CDCl$_3$) δ 1.65-1.81 (m, 4H), 1.88-1.99 (m, 4H), 2.18 (s, 3H), 2.24 (t, 2H), 2.44 (m, 1H), 2.83 (brd, 2H), 4.33 (t, 2H), 6.96 (d, 1H, J=7.5 Hz), 7.21-7.28 (m, 5H), 7.36 (d, 1H, 7.8 Hz), 7.53 (m, 2H), 7.69-7.77 (m, 3H); MS (m/e, M+): 505

Example 85

2-(4-chlorophenyl)-1-{3-[4-(3-acetylaminophenyl)piperidin-1-yl]propyl}-5-nitro-1H-benzimidazole 21 mg (yield 11%) of the title compound was obtained by repeating the procedure of Example 9 except for using 100 mg (0.36 mmol) of 2-(4-chlorophenyl)-5-nitro-1H-benzimidazole.

$^1$H NMR (300 MHz, CDCl$_3$) δ 1.64 (m, 2H), 1.78 (m, 2H), 1.96-2.04 (m, 4H), 2.20 (s, 3H), 2.24 (t, 2H), 2.43 (m, 1H), 2.78 (brd, 2H), 4.50 (t, 2H), 6.96 (d, 1H, J=7.8 Hz), 7.24-7.33 (m, 2H), 7.42 (d, 1H, J=7.8 Hz), 7.58 (d, 2H, J=8.4 Hz), 7.77 (d, 2H, J=8.4 Hz), 7.86 (d 1H, J=8.7 Hz), 8.24 (d, d 1H, J=8.7 Hz, 2.1 Hz), 8.54 (d, 1H, J=2.1 Hz); MS (m/e, M+): 532

Example 86

2-(4-chloro-2-methoxyphenyl)-1-{3-[4-(3-acetylaminophenyl)piperidin-1-yl]propyl}-5,6-dimethyl-1H-benzimidazole 52 mg (yield 28%) of the title compound was obtained by repeating the procedure of Example 9 except for using 100 mg (0.34 mmol) of 2-(4-chloro-2-methoxyphenyl)-5,6-dimethyl-1H-benzimidazole.

$^1$H NMR (300 MHz, CDCl$_3$) δ 1.58-1.67 (m, 2H), 1.74 (brd, 2H), 1.82-1.88 (m, 4H), 2.16 (s, 3H), 2.19 (t, 2H), 2.38 (s, 3H), 2.40 (s, 3H), 2.41 (m, 1H), 2.78 (brd, 2H), 3.83 (s, 3H), 4.07 (t, 2H), 6.94 (d, 1H, J=7.2 Hz), 7.02 (d, 1H, J=1.8 Hz), 7.07 (dd, 1H, J=8.1, 1.8 Hz), 7.21-7.30 (m, 4H), 7.38 (s, 1H), 7.42 (d, 1H, J=8.1 Hz), 7.55 (s, 1H); MS (m/e, M+): 545

Example 87

2-(5-chloro-2-methoxyphenyl)-1-{3-[4-(3-acetylaminophenyl)piperidin-1-yl]propyl}-5,6-dimethyl-1H-benzimidazole 59 mg (yield 32%) of the title compound was obtained by repeating the procedure of Example 9 except for using 100 mg (0.34 mmol) of 2-(5-chloro-2-methoxyphenyl)-5,6-dimethyl-1H-benzimidazole.

$^1$H NMR (300 MHz, CDCl$_3$) δ 1.64 (m, 2H), 1.76 (brd, 2H), 1.84-1.90 (m, 4H), 2.16 (s, 3H), 2.21 (t, 2H), 2.39 (s, 3H), 2.41 (s, 3H), 2.42 (m, 1H), 2.80 (brd, 2H), 3.77 (s, 3H), 4.09 (t, 2H), 6.94-6.97 (m, 2H), 7.21-7.31 (m, 2H), 7.36 (s, 1H), 7.40-7.44 (m, 2H), 7.49 (d, 1H, J=2.7 Hz), 7.55 (s, 1H); MS (m/e, M+): 545

Preparation of Imidazole Derivative

Examples 88 to 90

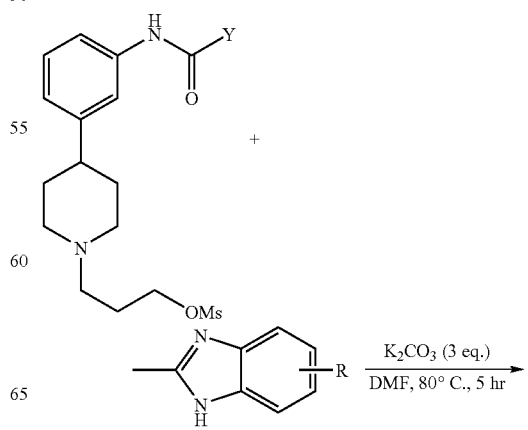

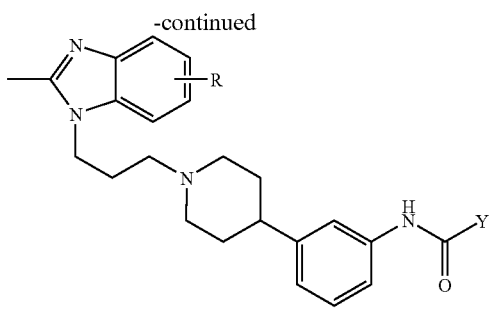

Example 88

2-methyl-1-{3-[4-(3-acetylaminophenyl)piperidin-1-yl]propyl}-1H-benzimidazole 100 mg (0.75 mmol) of 2-methyl-1H-benzimidazole was dissolved in 5 ml of N,N-dimethylformamide, and 265 mg (0.75 mmol) of 3-[4-(3-acetylaminophenyl)piperidin-1-yl]propylmethanesulfonate obtained by Preparation Example 4 and 310 mg (2.25 mmol) of $K_2CO_3$ were added to the resulting solution, followed by treating the mixture at 80° C. for 5 hours. The reaction mixture was combined with 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (5% MeOH/$CH_2Cl_2$) to obtain 160 mg (yield 55%) of the title compound.

$^1$H NMR (300 MHz, $CDCl_3$) δ 1.71-1.85 (m, 4H), 1.97-2.06 (m, 4H), 2.17 (s, 3H), 2.34 (t, 2H), 2.48 (m, 1H), 2.65 (s, 3H), 2.95 (brd, 2H), 4.22 (t, 2H), 6.97 (d, 1H, J=7.5 Hz), 7.20-7.38 (m, 6H), 7.43 (brs, 1H, NH), 7.67 (m, 1H); MS (m/e, M$^+$): 390, 375, 348, 257, 245, 231, 159

Example 89

2-methyl-1-{3-[4-(3-acetylaminophenyl)piperidin-1-yl]propyl}-5,6-dimethyl-1H-benzimidazole 145 mg (yield 56%) of the title compound was obtained by repeating the procedure of Example 88 except for using 100 mg (0.62 mmol) of 2,5,6-trimethyl-1H-benzimidazole.

$^1$H NMR (300 MHz, $CDCl_3$) δ 1.70-1.85 (m, 4H), 1.96-2.04 (m, 4H), 2.17 (s, 3H), 2.33 (t, 2H), 2.35 (s, 3H), 2.37 (s, 3H), 2.48 (m, 1H), 2.60 (s, 3H), 2.94 (brd, 2H), 4.16 (t, 2H), 6.91 (d, 1H, J=7.5 Hz), 7.12 (s, 1H), 7.21-7.37 (m, 2H), 7.43 (m, 2H), 7.62 (brs, 1H, NH); MS (m/e, M$^+$): 418, 403, 376, 257, 245, 231, 187, 174

Example 90

2-methyl-1-{3-[4-(3-isobutyrylaminophenyl)piperidin-1-yl]propyl}-1H-benzimidazole 100 mg (0.75 mmol) of 2-methyl-1H-benzimidazole was dissolved in 5 ml of N,N-dimethylformamide, and 286 mg (0.75 mmol) of 3-[4-(3-isobutyrylaminophenyl)piperidin-1-yl]propylmethanesulfonate and 310 mg (2.25 mmol) of $K_2CO_3$ were added to the resulting solution, followed by treating the mixture at 80° C. for 5 hours. The reaction mixture was combined with 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (5% MeOH/$CH_2Cl_2$) to obtain 159 mg (yield 51%) of the title compound.

$^1$H NMR (300 MHz, $CDCl_3$) δ 1.25 (d, 6H), 1.74-1.83 (m, 4H), 1.97-2.05 (m, 4H), 2.33 (t, 2H), 2.46 (m, 1H), 2.53 (m, 1H), 2.65 (s, 3H), 2.95 (brd, 2H), 4.22 (t, 2H), 6.97 (d, 1H), 7.09 (m, 1H), 7.20-7.38 (m, 5H), 7.53 (brs, 1H, NH), 7.70 (m, 1H); MS (m/e, M$^+$): 418

Preparation of Imidazole Derivative

Examples 91 to 97

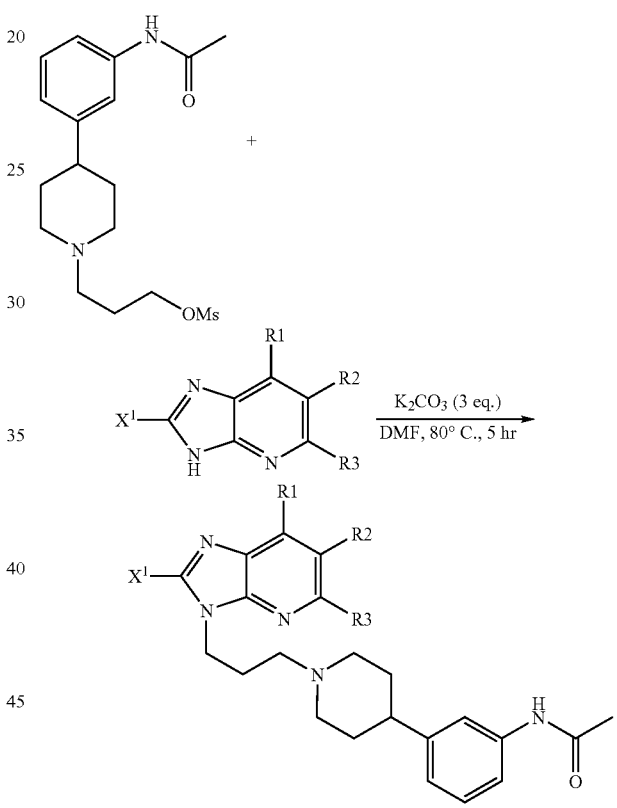

Example 91

2,5-dimethyl-3-{3-[4-(3-acetylaminophenyl)piperidin-1-yl]propyl}-3H-imidazo[4,5-b]pyridine 100 mg (0.68 mmol) of 2,5-dimethyl-3H-imidazo[4,5-b]pyridine was dissolved in 5 ml of N,N-dimethylformamide, and 240 mg (0.68 mmol) of 3-[4-(3-acetylaminophenyl)piperidin-1-yl]propylmethanesulfonate obtained by Preparation Example 4 and 282 mg (2.04 mmol) of $K_2CO_3$ were added to the resulting solution, followed by treating the mixture at 80° C. for 5 hours. The reaction mixture was combined with 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (5% MeOH/CH$_2$Cl$_2$) to obtain 124 mg (yield 45%) of the title compound.

$^1$H NMR (300 MHz, CDCl$_3$) δ 1.67-1.81 (m, 4H), 1.96-2.05 (m, 4H), 2.17 (m, 3H), 2.38 (t, 2H), 2.46 (m, 1H), 2.62 (s, 3H), 2.65 (s, 3H), 2.96 (br-d, 2H), 4.30 (t, 2H), 6.52 (m, 1H), 6.95 (m, 1H), 6.98 (d, 1H, J=8.1 Hz), 7.21-7.38 (m, 3H), 7.76 (d, 1H, J=8.1 Hz); MS (m/e, M$^+$): 405

Example 92

6-bromo-2,5-dimethyl-3-{3-[4-(3-acetylaminophenyl)piperidin-1-yl]propyl}-3H-imidazo[4,5-b]pyridine 100 mg (yield 47%) of the title compound was obtained by repeating the procedure of Example 91 except for using 100 mg (0.44 mmol) of 6-bromo-2,5-demethyl-3H-imidazo[4,5-b]pyridine.

$^1$H NMR (300 MHz, CDCl$_3$) δ 1.67-1.83 (m, 4H), 1.96-2.06 (m, 4H), 2.17 (m, 3H), 2.36 (t, 2H), 2.46 (m, 1H), 2.65 (s, 3H), 2.72 (s, 3H), 2.94 (br-d, 2H), 4.27 (t, 2H), 6.95 (d, 1H, J=6.8 Hz), 7.21-7.42 (m, 4H), 8.02 (s, 1H); MS (m/e, M$^+$): 484, 469, 267, 245, 231

Example 93

6-bromo-2-ethyl-5-methyl-3-{3-[4-(3-acetylaminophenyl)piperidin-1-yl]propyl}-3H-imidazo[4,5-b]pyridine 94 mg (yield 46%) of the title compound was obtained by repeating the procedure of Example 91 except for using 100 mg (0.41 mmol) of 6-bromo-2-ethyl-5-methyl-3H-imidazo[4,5-b]pyridine.

$^1$H NMR (300 MHz, CDCl$_3$) δ 1.47 (t, 3H), 1.68-1.83 (m, 4H), 1.96-2.07 (m, 4H), 2.16 (m, 3H), 2.38 (t, 2H), 2.46 (m, 1H), 2.72 (s, 3H), 2.94 (br-d, 2H), 2.99 (q, 2H), 4.27 (t, 2H), 6.95 (d, 1H, J=6.9 Hz), 7.21-7.43 (m, 4H), 8.06 (s, 1H); MS (m/e, M$^+$): 499, 497, 468, 280, 245, 231

Example 94

6-bromo-2-butyl-5-methyl-3-{3-[4-(3-acetylaminophenyl)piperidin-1-yl]propyl}-3H-imidazo[4,5-b]pyridine 87 mg (yield 45%) of the title compound was obtained by repeating the procedure of Example 91 except for using 100 mg (0.37 mmol) of 6-bromo-2-butyl-5-methyl-3H-imidazo[4,5-b]pyridine.

$^1$H NMR (300 MHz, CDCl$_3$) δ 0.98 (m, 3H), 1.25 (m, 3H), 1.84 (m, 6H), 1.97 (m, 3H), 2.16 (s, 3H), 2.37 (m, 2H), 2.96 (m, 5H), 4.25 (t, 2H), 6.96 (d, 1H), 7.32 (m, 2H), 7.62 (s, 1H), 8.05 (s, 1H): MS (m/e, M$^+$): 526, 468, 447

Example 95

2-butyl-5,7-dimethyl-3-{3-[4-(3-acetylaminophenyl)piperidin-1-yl]propyl}-3H-imidazo[4,5-b]pyridine 106 mg (yield 47%) of the title compound was obtained by repeating the procedure of Example 91 except for using 100 mg (0.49 mmol) of 2-butyl-5,7-dimethyl-3H-imidazo[4,5-b]pyridine.

$^1$H NMR (300 MHz, CDCl$_3$) δ 0.98 (m, 3H), 1.45 (m, 2H), 1.82 (m, 6H), 2.04 (m, 4H), 2.12 (s, 3H), 2.42 (m, 3H), 2.59 (s, 6H), 2.96 (m, 4H), 4.31 (t, 2H), 6.97 (d, 1H), 7.23 (m, 1H), 7.35 (m, 2H), 7.55 (s, 1H): MS (m/e, M$^+$): 461, 432, 404

Example 96

2-butyl-5,7-dimethyl-6-phenyl-3-{3-[4-(3-acetylaminophenyl)piperidin-1-yl]propyl}-3H-imidazo[4,5-b]pyridine 83 mg (yield 44%) of the title compound was obtained by repeating the procedure of Example 91 except for using 100 mg (0.35 mmol) of 2-butyl-5,7-dimethyl-6-phenyl-3H-imidazo[4,5-b]pyridine.

$^1$H NMR (300 MHz, CDCl$_3$) δ 0.97 (m, 3H), 1.46 (m, 2H), 1.86 (m, 6H), 2.04 (m, 4H), 2.11 (s, 3H), 2.32 (s, 6H), 2.48 (m, 3H), 2.99 (m, 6H), 4.35 (t, 2H), 6.95 (d, 1H), 7.15 (m, 2H), 7.38 (m, 5H), 7.44 (s, 1H): MS (m/e, M$^+$): 537, 508, 482

Example 97

2-butyl-5-methyl-6-pyridin-2-yl-3-{3-[4-(3-acetylaminophenyl)piperidin-1-yl]propyl}-3H-imidazo[4,5-b]pyridine 83 mg (yield 43%) of the title compound was obtained by repeating the procedure of Example 91 except for using 100 mg (0.37 mmol) of 2-butyl-5-methyl-6-pyridin-2-yl-3H-imidazo[4,5-b]pyridine.

$^1$H NMR (300 MHz, CDCl$_3$) δ 0.98 (m, 3H), 1.46 (m, 2H), 1.78 (m, 4H), 1.95 (m, 3H), 2.10 (m, 5H), 2.44 (m, 3H), 2.63 (s, 2H), 3.03 (m, 4H), 4.35 (t, 2H), 6.96 (d, 1H), 7.22 (m, 4H), 7.75 (m, 4H), 7.92 (s, 1H): MS (m/e, M$^+$): 524, 509, 495

Preparation of Imidazole Derivative

Examples 98 to 103

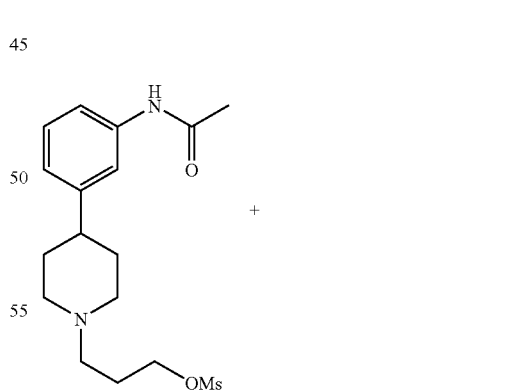

+

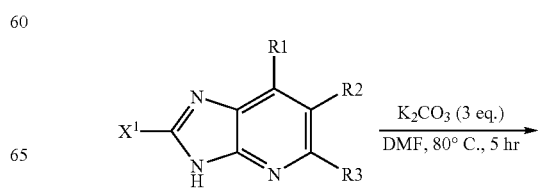

-continued

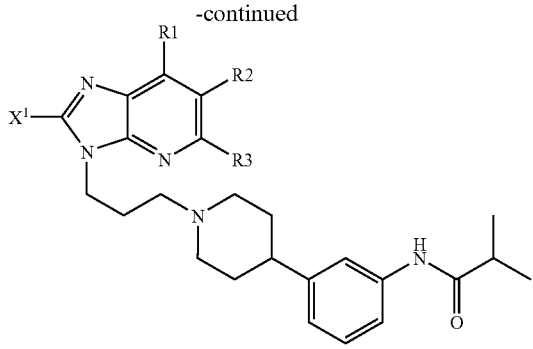

Example 98

6-bromo-2-butyl-5-methyl-3-{3-[4-(3-isobutyrylaminophenyl)piperidin-1-yl]propyl}-3H-imidazo[4,5-b]pyridine 100 mg (0.37 mmol) of 6-bromo-2-butyl-5-methyl-3H-imidazo[4,5-b]pyridine was dissolved in 5 ml of N,N-dimethylformamide, and 140 mg (0.37 mmol) of 3-[4-(3-isobutyrylaminophenyl)piperidin-1-yl]propylmethanesulfonate obtained by Preparation Example 5 and 155 mg (1.11 mmol) of $K_2CO_3$ were added to the resulting solution, followed by treating the mixture at 80° C. for 5 hours. The reaction mixture was combined with 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (5% MeOH/$CH_2Cl_2$) to obtain 94 mg (yield 46%) of the title compound.

$^1$H NMR (300 MHz, CDCl$_3$) δ 0.97 (t, 3H), 1.24 (m, 9H), 1.50 (m, 3H), 1.82 (m, 10H), 2.50 (m, 5H), 2.89 (m, 4H), 3.01 (m, 5H), 4.30 (t, 2H), 6.97 (d, 1H), 7.30 (m, 2H), 7.53 (d, 1H), 8.05 (s, 1H): MS (m/e, M$^+$): 554

Example 99

2-butyl-5,7-dimethyl-3-{3-[4-(3-isobutyrylaminophenyl)piperidin-1-yl]propyl}-3H-imidazo[4,5-b]pyridine 108 mg (yield 45%) of the title compound was obtained by repeating the procedure of Example 98 except for using 100 mg (0.49 mmol) of 2-butyl-5,7-dimethyl-3H-imidazo[4,5-b]pyridine.

$^1$H NMR (300 MHz, CDCl$_3$) δ 0.98 (m, 3H), 1.23 (m, 7H), 1.50 (m, 2H), 1.84 (m, 7H), 2.06 (m, 5H), 2.57 (m, 7H), 3.03 (m, 4H), 4.31 (t, 2H), 6.83 (s, 1H), 6.96 (d, 1H), 7.25 (m, 2H), 7.36 (d, 1H), 7.46 (s, 1H): MS (m/e, M$^+$): 489, 460, 432

Example 100

2-butyl-5,7-dimethyl-6-phenyl-3-{3-[4-(3-isobutyrylaminophenyl)piperidin-1-yl]propyl}-3H-imidazo[4,5-b]pyridine 91 mg (yield 46%) of the title compound was obtained by repeating the procedure of Example 98 except for using 100 mg (0.35 mmol) of 2-butyl-5,7-dimethyl-6-phenyl-3H-imidazo[4,5-b]pyridine.

$^1$H NMR (300 MHz, CDCl$_3$) δ 0.97 (t, 3H), 1.23 (m, 7H), 1.54 (m, 2H), 1.86 (m, 6H), 2.04 (m, 4H), 2.32 (s, 6H), 2.43 (m, 4H), 2.99 (m, 3H), 4.35 (t, 2H), 6.94 (d, 1H), 7.20 (m, 2H), 7.38 (m, 6H): MS (m/e, M$^+$): 565, 536, 508

Example 101

2-butyl-5-methyl-6-pyridin-2-yl-3-{3-[4-(3-isobutyrylaminophenyl)piperidin-1-yl]propyl}-3H-imidazo[4,5-b]pyridine 84 mg (yield 41%) of the title compound was obtained by repeating the procedure of Example 98 except for using 100 mg (0.37 mmol) of 2-butyl-5-methyl-6-pyridin-2-yl-3H-imidazo[4,5-b]pyridine.

$^1$H NMR (300 MHz, CDCl$_3$) δ 0.97 (m, 3H), 1.23 (m, 6H), 1.52 (m, 2H), 1.93 (m, 8H), 2.45 (m, 4H), 2.67 (s, 3H), 2.96 (m, 5H), 4.36 (t, 2H), 6.96 (d, 1H), 7.29 (m, 2H), 7.38 (m, 4H), 7.48 (m, 1H), 7.91 (s, 1H), 8.71 (m 1H); MS (m/e, M$^+$): 552, 523, 509

Example 102

2-butyl-5-formyl-6-phenyl-3-{3-[4-(3-isobutyrylaminophenyl)piperidin-1-yl]propyl}-3H-imidazo[4,5-b]pyridine 95 mg (yield 47%) of the title compound was obtained by repeating the procedure of Example 98 except for using 100 mg (0.36 mmol) of 2-butyl-6-phenyl-3H-imidazo[4,5-b]pyridine-5-carbaldehyde.

$^1$H NMR (300 MHz, CDCl$_3$) δ 1.02 (t, 3H), 1.23 (d, 6H), 1.28 (m, 2H), 1.52 (m, 2H), 1.81-2.04 (m, 8H), 2.16 (m, 1H), 2.45 (m, 2H), 2.52 (m, 1H), 3.01 (m, 2H), 3.04 (t, 2H), 4.47 (t, 2H), 6.94 (d, 1H), 7.21-7.48 (m, 8H), 7.95 (s, 1H), 10.07 (s, 1H): MS (m/e, M$^+$): 565

Example 103

2-butyl-5-methyl-6-(4-nitrophenyl)-3-{3-[4-(3-isobutyrylaminophenyl)piperidin-1-yl]propyl}-3H-imidazo[4,5-b]pyridine 82 mg (yield 43%) of the title compound was obtained by repeating the procedure of Example 98 except for using 100 mg (0.32 mmol) of 2-butyl-5-methyl-6-(4-nitrophenyl)-3H-imidazo[4,5-b]pyridine-5-carbaldehyde.

$^1$H NMR (300 MHz, CDCl$_3$) δ 0.99 (t, 3H), 1.23 (d, 6H), 1.28 (m, 2H), 1.50 (m, 2H), 1.70-2.04 (m, 8H), 2.12 (m, 1H), 2.44 (m, 1H), 2.49 (t, 2H), 2.51 (s, 3H), 2.97 ((t, 2H), 3.00 (m, 2H), 4.36 (t, 2H), 6.95 (d, 1H), 7.16-7.27 (m, 2H), 7.35 (brs, 1H, NH), 7.50 (d, 2H), 7.53 (m, 1H), 7.75 (s, 1H), 8.28 (d, 2H): MS (m/e, M$^+$): 596

Preparation of Imidazole Derivative

Examples 104 to 127

Example 104

2-(pyridin-2-yl)-1-{3-[4-(3-acetamidophenyl)piperidin-1-yl]propyl}-1H-benzimidazole 70 mg (0.36 mmol) of 2-(pyridin-2-yl)-1H-benzimidazole was dissolved in 5 ml of N,N-dimethylformamide, and 128 mg (0.31 mmol) of 3-[4-(3-acetylaminophenyl)piperidin-1-yl]propylmethanesulfonate obtained by Preparation Example 4 and 150 mg (1.08 mmol) of K₂CO₃ were added to the resulting solution, followed by treating the mixture at 80° C. for 5 hours. The reaction mixture was combined with 50 ml of water and extracted with ethylacetate (50 ml×2) being washed with water and a sodium hydroxide solution, and then the combined organic layer was dried over anhydrous sodium sulfate, and filtered. The solvent was removed from the filtrate under a reduced pressure, and the resulting residue was refined by silica gel column chromatography (10% MeOH/CH₂Cl₂) to obtain 87 mg (yield 53%) of the title compound.
$^1$H NMR (300 MHz, CDCl₃) δ 1.65-1.80 (m, 4H), 2.15 (s, 3H), 1.93-2.24 (m, 4H), 2.43 (br t, 2H, J=6.8 Hz), 2.48 (m, 1H), 2.98 (m, 2H), 4.90 (br t, 2H, J=7.3 Hz), 6.95 (m, 1H), 7.21-7.39 (m, 6H), 7.52 (m, 1H), 7.67 (br s, 1H), 7.84 (m, 2H), 8.40 (d, 1H, J=7.9 Hz), 8.86 (br d, 1H J=4.1 Hz); MS (m/e, M⁺): 453 (M⁺), 258, 209, 196

Example 105

2-(pyridin-3-yl)-1-{3-[4-(3-acetamidophenyl)piperidin-1-yl]propyl}-1H-benzimidazole 83 mg (yield 51%) of the title compound was obtained by repeating the procedure of Example 104 except for using 70 mg (0.36 mmol) of 2-(pyridin-3-yl)-1H-benzimidazole.
$^1$H NMR (300 MHz, CDCl₃) δ 1.58-1.77 (m, 4H), 1.89-2.04 (m, 4H), 2.17 (s, 3H), 2.27 (br t, 2H, J=6.6 Hz), 2.42 (m, 1H), 2.80 (m, 2H), 4.41 (br t, 2H, J=7.2 Hz), 6.95 (m, 1H), 7.21-7.40 (m, 5H), 7.48-7.53 (m, 2H), 7.65 (br s, 1H), 7.84 (m, 1H), 8.14 (dt, 1H, J=7.9, 1.8 Hz), 8.76 (dd, 1H, J=4.9, 1.5 Hz), 9.03 (m, 1H); MS (m/e, M⁺): 453 (M⁺), 257, 231, 70.

Example 106

2-(pyridin-4-yl)-1-{3-[4-(3-acetamidophenyl)piperidin-1-yl]propyl}-1H-benzimidazole 92 mg (yield 56%) of the title compound was obtained by repeating the procedure of Example 104 except for using 70 mg (0.36 mmol) of 2-(pyridin-4-yl)-1H-benzimidazole.
$^1$H NMR (300 MHz, CDCl₃) δ 1.55 (m, 2H), 1.74 (m, 2H), 1.90-2.02 (m, 4H), 2.20 (s, 3H), 2.25 (t, 2H), 2.42 (m, 1H), 2.79 (br-d, 2H), 4.47 (t, 2H), 6.91 (d, 1H), 7.21-7.50 (m, 6H), 7.76 (d, 2H), 7.85 (m, 1H), 7.82 (d, 2H); MS (m/e, M⁺): 453 (M⁺), 257, 231, 70.

Example 107

2-(furan-3-yl)-1-{3-[4-(3-acetylaminophenyl)piperidin-1-yl]propyl}-1H-benzimidazole 38 mg (yield 61%) of the title compound was obtained by repeating the procedure of Example 104 except for using 25.8 mg (0.14 mmol) of 2-(furan-3-yl)-1H-benzimidazole.
$^1$H NMR (300 MHz, CDCl₃) δ 1.80 (m, 4H), 2.03 (m, 4H), 2.17 (s, 3H), 2.39 (br t, 2H J=6.3 Hz), 2.48 (m, 1H), 2.94 (m, 2H), 4.41 (br t, 2H, J=7.3 Hz), 6.99 (m, 1H), 7.06 (m, 1H), 7.25-7.36 (m, 4H), 7.45 (m, 2H), 7.59 (m, 1H), 7.63 (br s, 1H), 7.74 (m, 1H), 8.21 (br s, 1H); MS (m/e, M⁺): 442 (M⁺), 413, 231, 70.

Example 108

2-(5-bromofuran-2-yl)-1-{3-[4-(3-acetylaminophenyl)piperidin-1-yl]propyl}-1H-benzimidazole 70 mg (yield 58%) of the title compound was obtained by repeating the procedure of Example 104 except for using 60.5 mg (0.23 mmol) of 2-(5-bromofuran-2-yl)-1H-benzimidazole.
$^1$H NMR (300 MHz, CDCl₃) δ 1.71-1.78 (m, 4H), 1.97-2.12 (m, 4H), 2.17 (s, 3H), 2.44 (m, 3H), 2.96 (m, 2H), 4.55 (br t, 2H, J=6.9 Hz), 6.55 (br d, 1H, J=3.4 Hz), 6.97 (br d, 1H, J=7.3 Hz), 7.20-7.54 (m, 8H), 7.77 (m, 1H); MS (m/e, M⁺): 521 (M⁺), 441, 231.

Example 109

2-(thiophen-2-yl)-1-{3-[4-(3-acetylaminophenyl)piperidin-1-yl]propyl}-1H-benzimidazole 54 mg (yield 84%) of the title compound was obtained by repeating the procedure of Example 104 except for using 28.1 mg (0.14 mmol) of 2-(thiophen-2-yl)-1H-benzimidazole.
$^1$H NMR (300 MHz, CDCl₃) δ 1.70-1.83 (m, 4H), 1.97-2.09 (m, 4H), 2.16 (s, 3H), 2.40 (br t, 2H J=6.6 Hz), 2.47 (m, 1H), 2.93 (m, 2H), 4.51 (br t, 2H, J=7.3 Hz), 6.97 (br, d, 1H, J=7.4 Hz), 7.19 (dd, 1H, J=5.0, 3.8 Hz), 7.22-7.35 (m, 4H), 7.45 (m, 2H), 7.51 (dd, 1H, J=5.0, 0.9 Hz), 7.64 (br s, 1H), 7.67 (m, 1H), 7.77-7.80 (m, 1H); MS (m/e, M⁺): 458 (M⁺), 425, 231, 70.

Example 110

2-(5-methylthiophen-2-yl)-1-{3-[4-(3-acetylaminophenyl)piperidin-1-yl]propyl}-1H-benzimidazole 70 mg (yield 64%) of the title compound was obtained by repeating the procedure of Example 104 except for using 49.3 mg (0.23 mmol) of 2-(5-methylthiophen-2-yl)-1H-benzimidazole.
$^1$H NMR (300 MHz, CDCl₃) δ 1.72-1.80 (m, 4H), 1.97-2.04 (m, 4H), 2.14 (s, 3H), 2.38 (br t, 2H, J=6.6 Hz), 2.47 (m, 1H), 2.94 (m, 2H), 3.88 (s, 3H), 4.37 (br t, 2H, J=7.2 Hz), 6.26 (m, 1H), 6.55 (m, 1H), 6.84 (br s, 1H), 6.97 (m, 1H), 7.21-7.50 (m, 6H), 7.78 (m, 1H), MS (m/e, M⁺): 457 (M⁺-15), 231, 209.

Example 111

2-(1-methylpyrrol-2-yl)-1-{3-[4-(3-acetylaminophenyl)piperidin-1-yl]propyl}-1H-benzimidazole 70 mg (yield 67%) of the title compound was obtained by repeating the procedure of Example 104 except for using 45.4 mg (0.23 mmol) of 2-(1-methylpyrrol-2-yl)-1H-benzimidazole.
$^1$H NMR (300 MHz, CDCl₃) δ 1.71-1.83 (m, 4H), 1.97-2.11 (m, 4H), 2.16 (s, 3H), 2.41 (t, 2H, J=6.5 Hz), 2.47 (m, 1H), 2.55 (s, 3H), 2.95 (m, 2H), 4.48 (br t, 2H, J=7.2 Hz), 6.84 (m, 1H), 6.97 (m, 1H), 7.22-7.36 (m, 5H), 7.41-7.47 (m, 3H), 7.68 (br s, 1H), 7.75 (m, 1H), MS (m/e, M⁺): 455 (M⁺), 257, 231.

Example 112

2-(5-bromopyridin-3-yl)-1-{3-[4-(3-acetylaminophenyl)piperidin-1-yl]propyl}-1H-benzimidazole 47 mg (yield 80%) of the title compound was obtained by repeating the procedure of Example 104 except for using 30.2 mg (0.11 mmol) of 2-(5-bromopyridin-3-yl)-1H-benzimidazole.
$^1$H NMR (300 MHz, CDCl₃) δ 1.63 (m, 2H), 1.77 (m, 2H), 1.91-2.05 (m, 4H), 2.18 (s, 3H), 2.28 (br t, 2H, J=6.5 Hz), 2.43 (m, 1H), 2.82 (m, 2H), 4.42 (br t, 2H, J=7.2 Hz), 6.97 (m, 1H), 7.22-7.40 (m, 6H), 7.52 (m, 1H), 7.84 (m, 1H), 8.35 (t, 1H, J=2.1 Hz), 8.82 (d, 1H, J=2.2 Hz), 8.96 (d, 1H, J=1.8 Hz); MS (m/e, M⁺): 532 (M⁺), 257, 231, 70.

Example 113

2-(6-chloropyridin-3-yl)-1-{3-[4-(3-acetamidophenyl)piperidin-1-yl]propyl}-1H-benzimidazole 40 mg (yield 75%) of the title compound was obtained by repeating the procedure of Example 104 except for using 25.3 mg (0.11 mmol) of 2-(6-chloropyridin-3-yl)-1H-benzimidazole.
¹H NMR (300 MHz, CDCl₃) δ 1.65 (m, 2H), 1.77 (m, 2H), 1.92-2.06 (m, 4H), 2.18 (s, 3H), 2.27 (br t, 2H, J=6.3 Hz), 2.44 (m, 1H), 2.82 (m, 2H), 4.41 (br t, 2H, J=7.4 Hz), 6.99 (m, 1H), 7.23-7.40 (m, 6H), 7.51 (m, 2H), 7.83 (m, 1H), 8.16 (dd, 1H, J=8.3, 2.5 Hz), 8.90 (m, 1H); MS (m/e, M⁺): 488 (M⁺), 257, 231, 70.

Example 114

2-(6-methylpyridin-3-yl)-1-{3-[4-(3-acetamidophenyl)piperidin-1-yl]propyl}-1H-benzimidazole 46 mg (yield 89%) of the title compound was obtained by repeating the procedure of Example 104 except for using 23.0 mg (0.11 mmol) of 2-(6-methylpyridin-3-yl)-1H-benzimidazole.
¹H NMR (300 MHz, CDCl₃) δ 1.56-1.68 (m, 2H), 1.76 (m, 2H), 1.90-2.03 (m, 4H), 2.17 (s, 3H), 2.27 (br t, 2H, J=6.6 Hz), 2.43 (m, 1H), 2.65 (s, 3H), 2.82 (m, 2H), 4.39 (br t, 2H, J=7.3 Hz), 6.96 (m, 1H), 7.23 (m, 1H), 7.31-7.36 (m, 4H), 7.40 (br s, 1H), 7.50 (m, 2H), 7.83 (m, 1H), 8.02 (dd, 1H, J=8.0, 2.3 Hz), 8.90 (d, 1H, J=2.1 Hz); MS (m/e, M⁺): 467 (M⁺), 250, 231, 70.

Example 115

2-(2-methoxypyridin-3-yl)-1-{3-[4-(3-acetamidophenyl)piperidin-1-yl]propyl}-1H-benzimidazole 53 mg (yield 78%) of the title compound was obtained by repeating the procedure of Example 104 except for using 31.5 mg (0.14 mmol) of 2-(2-methoxypyridin-3-yl)-1H-benzimidazole.
¹H NMR (300 MHz, CDCl₃) δ 1.62 (m, 2H), 1.73 (m, 2H), 1.90 (m, 4H), 2.16 (s, 3H), 2.23 (br t, 2H, J=6.8 Hz), 2.47 (m, 1H), 2.80 (m, 2H), 3.98 (s, 3H), 4.19 (t, 2H, J=7.2 Hz), 6.94 (m, 1H), 7.06 (dd, 1H, J=7.2, 5.1 Hz), 7.21-7.39 (m, 6H), 7.50 (m, 1H), 7.82 (m, 1H), 7.88 (dd, 1H, J=7.3, 1.8 Hz), 8.34 (dd, 1H, J=5.0, 1.8 Hz); MS (m/e, M⁺): 483 (M⁺), 468, 252, 231, 70.

Example 116

5-chloro-2-(pyridin-3-yl)-1-{3-[4-(3-acetamidophenyl)piperidin-1-yl]propyl}-1H-benzimidazole 40 mg (yield 59%) of the title compound was obtained by repeating the procedure of Example 104 except for using 32.2 mg (0.14 mmol) of 5-chloro-2-(pyridin-3-yl)-1H-benzimidazole.
¹H NMR (300 MHz, CDCl₃) δ 1.57-1.77 (m, 4H), 1.91-2.00 (m, 4H), 2.18 (s, 3H), 2.26 (br t, 2H, J=6.3 Hz), 2.43 (m, 1H), 2.80 (m, 2H), 4.39 (m, 2H), 6.97 (m, 1H), 7.22-7.41 (m, 5H), 7.50 (dd, 1H, J=7.8, 4.9 Hz) 7.57 (d, 1H, J=1.8 Hz), 7.74 (d, 1H, J=8.6 Hz), 8.13 (dt, 1H, J=7.9, 1.8 Hz), 8.78 (m, 1H), 9.03 (m, 1H); MS (m/e, M⁺): 488 (M⁺), 257, 231, 70.

Example 117

5-nitro-2-(pyridin-3-yl)-1-{3-[4-(3-acetamidophenyl)piperidin-1-yl]propyl}-1H-benzimidazole 70 mg (yield 44%) of the title compound was obtained by repeating the procedure of Example 104 except for using 76.9 mg (0.32 mmol) of 5-nitro-2-(pyridin-3-yl)-1H-benzimidazole.
¹H NMR (300 MHz, CDCl₃) δ 1.47-1.76 (m, 4H), 1.89-1.99 (m, 4H), 2.20 (s, 3H), 2.27 (m, 2H), 2.43 (m, 1H), 2.77 (m, 2H), 4.51 (m, 2H), 6.95 (m, 1H), 7.22-7.40 (m, 4H), 7.56 (dd, 1H, J=7.8, 4.9 Hz), 7.63 (d, 1H, J=9.0 Hz), 8.16 (m, 1H), 8.30 (dd, 1H, J=9.1, 2.1 Hz), 8.75 (d, 1H, J=2.0 Hz), 8.83 (m, 1H), 9.06 (d, 1H, J=1.9 Hz); MS (m/e, M⁺): 498 (M⁺), 481, 231, 70.

Example 118

5-chloro-2-(5-bromofuran-2-yl)-1-{3-[4-(3-acetamidophenyl)piperidin-1-yl]propyl}-1H-benzimidazole 25 mg (yield 64%) of the title compound was obtained by repeating the procedure of Example 104 except for using 20.8 mg (0.07 mmol) of 5-chloro-2-(5-bromofuran-2-yl)-1H-benzimidazole.
¹H NMR (300 MHz, MeOH-d₄) δ 1.66-1.81 (m, 4H), 2.03-2.13 (m, 4H), 2.14 (s, 3H), 2.45 (m, 2H), 2.96 (m, 2H), 4.63 (m, 2H), 6.58 (m, 1H), 6.78 (m, 1H), 7.00 (m, 1H), 7.24 (t, 1H, J=7.8 Hz), 7.30-7.44 (m, 3H), 7.63-7.81 (m, 3H); MS (m/e, M⁺): 475 (M⁺-Br), 257, 231.

Example 119

2-(furan-2-yl)-5-methoxy-1-{3-[4-(3-acetamidophenyl)piperidin-1-yl]propyl}-1H-benzimidazole 30 mg (yield 68%) of the title compound was obtained by repeating the procedure of Example 104 except for using 19.9 mg (0.09 mmol) of 2-(furan-2-yl)-5-methoxy-1H-benzimidazole.
¹H NMR (300 MHz, CDCl₃) δ 1.77-1.84 (m, 4H), 1.99-2.12 (m, 4H), 2.17 (s, 3H), 2.45 (m, 3H), 3.00 (m, 2H), 3.89 (s, 3H), 4.54 (q, 2H, J=7.1 Hz), 6.60 (m, 1H), 6.94 (m, 2H), 7.17-7.41 (m, 7H), 7.60 (m, 1H); MS (m/e, M⁺): 472 (M⁺), 257, 231, 120.

Example 120

5-methyl-2-(thiophen-3-yl)-1-{3-[4-(3-acetamidophenyl)piperidin-1-yl]propyl}-1H-benzimidazole 27 mg (yield 61%) of the title compound was obtained by repeating the procedure of Example 104 except for using 19.9 mg (0.09 mmol) of 5-methyl-2-(thiophen-3-yl)-1H-benzimidazole.
¹H NMR (300 MHz, CDCl₃) δ 1.80 (m, 4H), 2.04 (m, 4H), 2.16 (s, 3H), 2.38 (m, 2H), 2.46 (m, 1H), 2.49 (s, 3H), 2.94 (m, 2H), 4.41 (br t, 2H, J=6.8 Hz), 6.98 (m, 1H), 7.12 (m, 1H), 7.22-7.34 (m, 3H), 7.43-7.48 (m, 2H), 7.56-7.67 (m, 3H), 7.91 (br s, 1H); MS (m/e, M⁺): 472 (M⁺), 256, 231, 70.

Example 121

5,6-dimethyl-2-(1-methylpyrrol-2-yl)-1-{3-[4-(3-acetamidophenyl)piperidin-1-yl]propyl}-1H-benzimidazole 42 mg (yield 62%) of the title compound was obtained by repeating the procedure of Example 104 except for using 31.5 mg (0.14 mmol) of 5,6-dimethyl-2-(1-methylpyrrol-2-yl)-1H-benzimidazole.
¹H NMR (300 MHz, CDCl₃) δ 1.81 (m, 4H), 2.00 (m, 4H), 2.14 (s, 3H), 2.37 (m, 2H), 2.39 (s, 3H), 2.40 (s, 3H), 2.48 (m, 1H), 2.97 (m, 2H), 3.85 (s, 3H), 4.31 (br t, 2H, J=7.4 Hz), 6.24 (br t, 1H, J=2.9 Hz), 6.50 (m, 1H), 6.81 (br s, 1H), 6.97 (m, 1H), 7.20-7.27 (m, 2H), 7.35 (m, 1H), 7.43 (m, 2H), 7.55 (br s, 1H); MS (m/e, M⁺): 483 (M⁺), 252, 231, 70.

Example 122

2-(thiazol-4-yl)-1-{3-[4-(3-acetamidophenyl)piperidin-1-yl]propyl}-1H-benzimidazole 34 mg (yield 80%) of the title compound was obtained by repeating the procedure of Example 104 except for using 18.7 mg (0.09 mmol) of 2-(4-thiazolyl)-1H-benzimidazole.
¹H NMR (300 MHz, MeOH-d₄) δ 1.74-1.90 (m, 4H), 2.10 (s, 3H), 2.24 (m, 2H), 2.44 (m, 2H), 2.61 (m, 1H), 2.76 (br t, 2H, J=7.5 Hz), 3.22 (m, 2H), 4.86 (m, 2H), 6.94 (m, 1H), 7.21 (br t, 1H, J=7.7 Hz), 7.30-7.40 (m, 3H), 7.48 (br s, 1H), 7.69 (br t, 2H, J=7.4 Hz), 8.38 (d, 1H, J=1.8 Hz), 9.21 (d, 1H, J=1.9 Hz); MS (m/e, M⁺): 459 (M⁺), 257, 231, 70.

Example 123

2-(4-methyloxazol-5-yl)-1-{3-[4-(3-acetamidophenyl)piperidin-1-yl]propyl}-1H-benzimidazole 45 mg (yield 70%) of the title compound was obtained by repeating the procedure of Example 104 except for using 27.9 mg (0.14 mmol) of 2-(4-methyloxazol-5-yl)-1H-benzimidazole.
¹H NMR (300 MHz, CDCl₃) δ 1.68-1.83 (m, 4H), 1.94-2.10 (m, 4H), 2.17 (s, 3H), 2.36 (br t, 2H, J=6.8 Hz), 2.47 (m, 1H), 2.64 (s, 3H), 2.93 (m, 2H), 4.50 (br t, 2H, J=7.1 Hz), 6.97 (m, 1H), 7.21-7.34 (m, 4H), 7.42 (m, 2H), 7.49 (m, 1H), 7.82 (m, 1H), 7.99 (s, 1H); MS (m/e, M⁺): 457 (M⁺), 257, 231, 120.

Example 124

2-(1-methyl-1H-imidazol-5-yl)-1-{3-[4-(3-acetamidophenyl)piperidin-1-yl]propyl}-1H-benzimidazole 66 mg (yield 85%) of the title compound was obtained by repeating the procedure of Example 104 except for using 33.7 mg (0.17 mmol) of 2-(1-methyl-1H-imidazol-5-yl)-1H-benzimidazole.
¹H NMR (300 MHz, CDCl₃) δ 1.72-1.84 (m, 4H), 2.04 (m, 4H), 2.18 (s, 3H), 2.40 (t, 2H, J=6.7 Hz), 2.48 (m, 1H), 2.96 (m, 2H), 3.98 (s, 3H), 4.42 (t, 2H, J=7.4 Hz), 6.97 (d, 1H, J=7.6 Hz), 7.24 (m, 1H), 7.32 (m, 2H), 7.37 (m, 1H), 7.43 (m, 1H), 7.50 (m, 1H), 7.54 (br s, 1H), 7.67 (br s, 1H), 7.70 (br s, 1H), 7.80 (m, 1H): MS (m/e, M⁺): 456 (M⁺), 231.

Example 125

2-(pyridin-2-ylmethyl)-1-{3-[4-(3-acetamidophenyl)piperidin-1-yl]propyl}-1H-benzimidazole 140 mg (yield 52%) of the title compound was obtained by repeating the procedure of Example 104 except for using 121.4 mg (0.58 mmol) of 2-(pyridin-2-ylmethyl)-1H-benzimidazole.
¹H NMR (300 MHz, CDCl₃) δ 1.70-1.99 (m, 8H), 2.16 (s, 3H), 2.30 (t, 2H, J=6.8 Hz), 2.46 (m, 1H), 2.89 (m, 2H), 4.27 (t, 2H, J=7.1 Hz), 4.58 (s, 2H), 6.98 (m, 1H), 7.15 (m, 1H), 7.21-7.40 (m, 8H), 7.59 (dt, 1H, J=7.7, 1.8 Hz), 7.75 (m, 1H), 8.54 (m, 1H); MS (m/e, M⁺): 467 (M⁺), 375, 223.

Example 126

2-(pyridin-3-ylmethyl)-1-{3-[4-(3-acetamidophenyl)piperidin-1-yl]propyl}-1H-benzimidazole 60 mg (yield 71%) of the title compound was obtained by repeating the procedure of Example 104 except for using 37.7 mg (0.18 mmol) of 2-(pyridin-3-ylmethyl)-1H-benzimidazole.
¹H NMR (300 MHz, CDCl₃) δ 1.72-2.04 (m, 8H), 2.19 (s, 3H), 2.28 (t, 2H, J=6.3 Hz), 2.50 (m, 1H), 2.95 (m, 2H), 4.16 (t, 2H, J=6.8 Hz), 4.47 (s, 2H), 6.96 (m, 1H), 7.22-7.30 (m, 4H), 7.37 (m, 2H), 7.49 (br d, 1H, J=7.8 Hz), 7.57 (m 1H), 7.77 (m, 1H), 8.03 (br s, 1H), 8.51 (dd, 1H, J=4.7, 1.4 Hz), 8.68 (m, 1H); MS (m/e, M⁺): 467 (M⁺), 375, 245.

Example 127

2-[2-(pyridin-3-yl)ethyl]-1-{3-[4-(3-acetamidophenyl)piperidin-1-yl]propyl}-1H-benzimidazole 75 mg (yield 87%) of the title compound was obtained by repeating the procedure of Example 104 except for using 40.2 mg (0.18 mmol) of 2-[2-(pyridin-3-yl)ethyl]-1H-benzimidazole.
¹H NMR (300 MHz, CDCl₃) δ 1.59 (m, 2H), 1.74 (m, 2H), 1.91-2.03 (m, 4H), 2.18 (t, 2H, J=6.0 Hz), 2.27 (s, 3H), 2.44 (m, 1H), 2.87 (m, 2H), 3.30 (m, 2H), 3.40 (m, 2H), 4.29 (t, 2H, J=6.4 Hz), 6.87 (m, 1H), 7.05 (s, 1H), 7.21-7.32 (m 4H), 7.38 (m, 1H), 7.71 (dt, 1H, J=7.8, 1.8 Hz), 7.77 (m, 1H), 7.89 (br dd, 1H, J=8.2, 1.2 Hz), 8.51 (dd, 1H, J=4.8, 1.6 Hz), 8.76 (d, 1H, J=1.8 Hz), 9.37 (br s, 1H); MS (m/e, M⁺): 481 (M⁺), 245, 159, 70.

The substituents of the compounds described in Examples among imidazole derivatives of formula (I) of the present invention were shown in Table 2.

TABLE 2

| Example | R¹ | R² | R³ | A | n |
|---|---|---|---|---|---|
| 1 | Ph | H | Me | CH | 2 |
| 2 | 4-Cl—Ph | H | Me | CH | 2 |
| 3 | Ph | H | Me | CH | 3 |
| 4 | 4-Cl—Ph | H | Me | CH | 3 |
| 5 | Ph | H | Me | CH | 4 |

TABLE 2-continued

| Example | R¹ | R² | R³ | A | n |
|---|---|---|---|---|---|
| 6 | 4-Cl—Ph | H | Me | CH | 4 |
| 7 | Ph | H | Me | CH | 5 |
| 8 | 4-Cl—Ph | H | Me | CH | 5 |
| 9 | 2-Cl—Ph | H | Me | CH | 3 |
| 10 | 3-Cl—Ph | H | Me | CH | 3 |
| 11 | 4-Br—Ph | H | Me | CH | 3 |
| 12 | 3,4-di-Cl—Ph | H | Me | CH | 3 |
| 13 | 3-Br—Ph | H | Me | CH | 3 |
| 14 | 2-I—Ph | H | Me | CH | 3 |
| 15 | 2-F—Ph | H | Me | CH | 3 |
| 16 | 2,4-di-Cl—Ph | H | Me | CH | 3 |
| 17 | 2-OMe—Ph | H | Me | CH | 3 |
| 18 | 3-OMe—Ph | H | Me | CH | 3 |
| 19 | 4-OMe—Ph | H | Me | CH | 3 |
| 20 | 4-iPr—Ph | H | Me | CH | 3 |
| 21 | Ph | 5,6-di-Me | Me | CH | 3 |
| 22 | 4-Cl—Ph | 5,6-di-Me | Me | CH | 3 |
| 23 | Ph | 6-Me | Me | CH | 3 |
| 24 | 4-Cl—Ph | 6-Me | Me | CH | 3 |
| 25 | 4-Cl—Ph | 6-Cl | Me | CH | 3 |
| 26 | Ph | 6-F | Me | CH | 3 |
| 27 | Ph | 6-OMe | Me | CH | 3 |
| 28 | 4-Cl—Ph | 6-OMe | Me | CH | 3 |
| 29 | Ph | 6-Cl | Me | CH | 3 |
| 30 | 4-F—Ph | 6-Cl | Me | CH | 3 |
| 31 | 4-Cl—Ph | 6-F | Me | CH | 3 |
| 32 | Ph | 6-NO₂ | Me | CH | 3 |
| 33 | 2-F—Ph | 6-Cl | Me | CH | 3 |
| 34 | 3-F—Ph | 6-Cl | Me | CH | 3 |
| 35 | 3-Cl—Ph | 6-Cl | Me | CH | 3 |
| 36 | 4-Cl—Ph | 6-Br | Me | CH | 3 |
| 37 | 2-Cl—Ph | 5,6-di-Me | Me | CH | 3 |
| 38 | 3-Cl—Ph | 5,6-di-Me | Me | CH | 3 |
| 39 | 4-Cl—Ph | 4,5-di-Me | Me | CH | 3 |
| 40 | 2-Cl—Ph | 6-NO₂ | Me | CH | 3 |
| 41 | 3-Cl—Ph | 6-NO₂ | Me | CH | 3 |
| 42 | 4-Cl—Ph | 6-NO₂ | Me | CH | 3 |
| 43 | Ph | 6-Br | Me | CH | 3 |
| 44 | 2,3,4,5-tet-F—Ph | H | Me | CH | 3 |
| 45 | 4-CF₃—Ph | H | Me | CH | 3 |
| 46 | 4-Ph—Ph | H | Me | CH | 3 |
| 47 | 4-OPh—Ph | H | Me | CH | 3 |
| 48 | 4-F—Ph | H | Me | CH | 3 |
| 49 | 4-Cl—Ph | 5,7-di-Me | Me | CH | 3 |
| 50 | 3,4-di-F—Ph | H | Me | CH | 3 |
| 51 | 4-CN—Ph | H | Me | CH | 3 |
| 52 | 3-CN—Ph | H | Me | CH | 3 |
| 53 | 2-F, 4-Cl—Ph | H | Me | CH | 3 |
| 54 | 2-Cl, 4-F—Ph | H | Me | CH | 3 |
| 55 | 3-NO₂—Ph | H | Me | CH | 3 |
| 56 | 2-OMe, 5-Cl—Ph | H | Me | CH | 3 |
| 57 | 2-Cl, 4-NO₂—Ph | H | Me | CH | 3 |
| 58 | 2,4-di-OMe—Ph | H | Me | CH | 3 |
| 59 | 2-F, 4-Cl—Ph | 5,6-di-Me | Me | CH | 3 |
| 60 | Ph | 6-Me | Me | CH | 3 |
| 61 | 4-Cl—Ph | 6-CONH₂ | Me | CH | 3 |
| 62 | 3-CONH₂—Ph | H | Me | CH | 3 |
| 63 | 2-OH—Ph | H | Me | CH | 3 |
| 64 | 4-Cl—Ph | H | i-Pr | CH | 3 |
| 65 | 4-Cl—Ph | H | Ph | CH | 3 |
| 66 | 4-Cl—Ph | H | 3-Cl—Ph | CH | 3 |
| 67 | 4-Cl—Ph | H | 4-Me—Ph | CH | 3 |
| 68 | Ph | 5-Br, 6-Me | Me | 7-N | 3 |
| 69 | Ph | 6-Me | Me | 7-N | 3 |
| 70 | 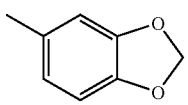 | H | Me | CH | 3 |
| 71 | 4-Cl—Ph | H | i-Pr | CH | 2 |
| 72 | Ph | H | Me | 6-N | 3 |
| 73 | Ph | H | Me | 5-N | 3 |
| 74 | Ph | 6-Br, 5-Me | Me | 4-N | 3 |
| 75 | Ph | 5-Me | Me | 4-N | 3 |
| 76 | 3-CO₂Me—Ph | H | Me | CH | 3 |
| 77 | 4-Et—Ph | H | Me | CH | 3 |

TABLE 2-continued

| Example | R¹ | R² | R³ | A | n |
|---|---|---|---|---|---|
| 78 | 4-CN—Ph | 5,6-di-Me | Me | CH | 3 |
| 79 | 3-Me—Ph | H | Me | CH | 3 |
| 80 | 2-Cl, 4-F—Ph | 5,6-di-Me | Me | CH | 3 |
| 81 | 4-Cl—Ph | 5-CN | Me | CH | 3 |
| 82 | 4-Cl—Ph | 6-CN | Me | CH | 3 |
| 83 | 4-Cl—Ph | 5-F | Me | CH | 3 |
| 84 | 4-F—Ph | 5-Cl | Me | CH | 3 |
| 85 | 4-Cl—Ph | 5-NO₂ | Me | CH | 3 |
| 86 | 2-OMe, 4-Cl—Ph | 5,6-di-Me | Me | CH | 3 |
| 87 | 2-OMe, 5-Cl—Ph | 5,6-di-Me | Me | CH | 3 |
| 88 | Me | H | Me | CH | 3 |
| 89 | Me | 5,6-di-Me | Me | CH | 3 |
| 90 | Me | H | i-Pr | CH | 3 |
| 91 | Me | 6-Me | Me | 7-N | 3 |
| 92 | Me | 5-Br, 6-Me | Me | 7-N | 3 |
| 93 | Et | 5-Br, 6-Me | Me | 7-N | 3 |
| 94 | n-Bu | 5-Br, 6-Me | Me | 7-N | 3 |
| 95 | n-Bu | 4,6-di-Me | Me | 7-N | 3 |
| 96 | n-Bu | 4,6-di-Me, 5-Ph | Me | 7-N | 3 |
| 97 | n-Bu | 5-(2-pyridyl), 6-Me | Me | 7-N | 3 |
| 98 | n-Bu | 5-Br, 6-Me | i-Pr | 7-N | 3 |
| 99 | n-Bu | 4,6-di-Me | i-Pr | 7-N | 3 |
| 100 | n-Bu | 4,6-di-Me, 5-Ph | i-Pr | 7-N | 3 |
| 101 | nBu | 5-(2-Pyridyl), 6-Me | i-Pr | 7-N | 3 |
| 102 | n-Bu | 5-Ph, 6-CHO | i-Pr | 7-N | 3 |
| 103 | n-Bu | 5-(4-NO₂—Ph), 6-Me | i-Pr | 7-N | 3 |
| 104 | 2-pyridyl | H | Me | CH | 3 |
| 105 | 3-pyridyl | H | Me | CH | 3 |
| 106 | 4-pyridyl | H | Me | CH | 3 |
| 107 | 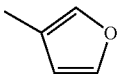 | H | Me | CH | 3 |
| 108 | 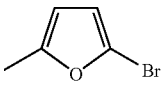 | H | Me | CH | 3 |
| 109 | 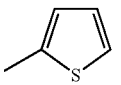 | H | Me | CH | 3 |
| 110 | 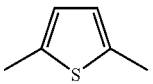 | H | Me | CH | 3 |
| 111 | 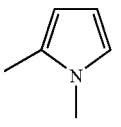 | H | Me | CH | 3 |
| 112 | 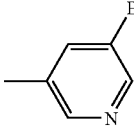 | H | Me | CH | 3 |
| 113 | 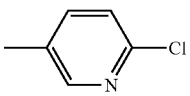 | H | Me | CH | 3 |
| 114 | 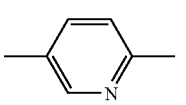 | H | Me | CH | 3 |

TABLE 2-continued

| Example | R¹ | R² | R³ | A | n |
|---|---|---|---|---|---|
| 115 | 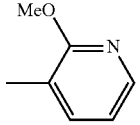 | H | Me | CH | 3 |
| 116 | 2-pyridyl | 6-Cl | Me | CH | 3 |
| 117 | 2-pyridyl | 6-NO$_2$ | Me | CH | 3 |
| 118 | 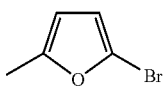 | 6-Cl | Me | CH | 3 |
| 119 | 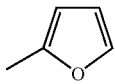 | 6-OMe | Me | CH | 3 |
| 120 | 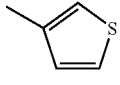 | 5-Me | Me | CH | 3 |
| 121 | 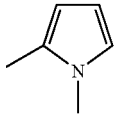 | 5,6-di-Me | Me | CH | 3 |
| 122 | 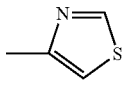 | H | Me | CH | 3 |
| 123 | 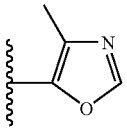 | H | Me | CH | 3 |
| 124 | 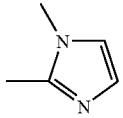 | H | Me | CH | 3 |
| 125 | 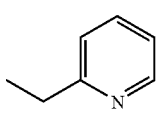 | H | Me | CH | 3 |
| 126 | 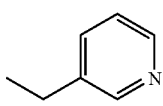 | H | Me | CH | 3 |
| 127 | 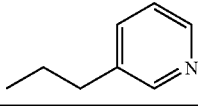 | H | Me | CH | 3 |

Test Example 1

Inhibitory Effects on MCH R1 Binding of Aryl Piperidine Group-Containing Imidazole Derivatives First, MCH R1 (melanine-concentrating hormone receptor-1; Euroscreen, Gosselies, Belgium), 1 μM Europium-labeled melanine-concentrating hormone (Eu-MCH, PerkinElmer, Turku, Finland) and 1 mM melanine-concentrating hormone (MCH, #070-47, Phoenix, Belmont Calif., USA) were kept at 4° C. for ready use. 1 μM Eu-MCH and 1 mM MCH were diluted with an experimental solution (25 mM HEPES pH 7.4, 5 mM MgCl$_2$, 1 mM CaCl$_2$ and 0.5% (w/w) BSA) to 8 nM (final reaction concentration: 2 nM) and 2 μM (final reaction concentration: 0.5 μM), respectively. The compounds prepared in the Examples ("Test compounds") were dissolved in the experimental solution in concentration of 4 nM to 40 μM (final reaction concentration: 1 nM to 10 μM). MCH R1 (200 assays/vial) was homogeneously dispersed in the experimental solution.

Then, 100 μl/well of the following reaction mixture was added to the wells of a microplate (Multiwell 96 well filter plates PN5020, Pall Co., Ann Arbor, Mich., USA) equipped with a filter paper, with an 8-channel pipette (multi 8-channel, Eppendorf, Hamburg, Germany). Specifically, to the wells of a non-specific binding control group, 25 μl of Eu-MCH, 50 μl of MCH R1 and 25 μl of MCH were added. Further, 25 μl of the experimental solution supplemented with 10% (w/w) of DMSO, 25 μl of Eu-MCH and 50 μl of MCH R1 were added to the wells of a total binding control group, while 25 μl of the test compounds, 25 μl Eu-MCH and 50 μl of MCH R1 were added to the wells of an experimental group. Subsequently, the microplate was shaken gently for 15 seconds and kept at room temperature for 90 minutes to allow the reaction to take place. Then, the plate was washed with a microplate washer (EMBLA, Molecular Devices) by washing three times with 300 μl of a washing solution (25 mM HEPES pH 7.4, 5 mM $MgCl_2$, 1 mM $CaCl_2$) to remove the residual unreacted Eu-MCH. Moisture was removed from the bottom of the wells and 150 μl of dissociation solution (DELFIA Enhancement solution, PerkinElmer, Turku, Finland) was added to each well, followed by keeping the plate at room temperature for 2 to 4 hours. Subsequently, time-resolved fluorescence (TRF) values were measured with a multilabel counter (Victor2, PerkinElmer, Turku, Finland) (emission wave length: 615 nm, excitation wave length: 340 nm). The inhibition rate based on the time-resolved fluorescence data was calculated using the following Equation (I).

Inhibition rate of time-resolved fluorescence (%)= [(Average TRF value of the total binding group−Time-resolved fluorescence value of the test compound)/(Average TRF value of the total binding group−Average TRF value of the non-specific binding group)]×100     (I)

Table 3 shows the $IC_{50}$ values of the test compounds, which represents the concentration of the test compounds inhibiting the binding of MCH to MCH R1 by 50% in vitro.

TABLE 3

| Compound | $IC_{50}$ (nM) |
| --- | --- |
| Example 1 | >10,000 |
| Example 2 | 6,000 |
| Example 3 | 2 |
| Example 4 | 1 |
| Example 5 | 29 |
| Example 6 | 1 |
| Example 7 | 74 |
| Example 8 | 32 |
| Example 9 | 10 |
| Example 10 | 5 |
| Example 11 | 5 |
| Example 12 | 24 |
| Example 13 | 1 |
| Example 14 | >10,000 |
| Example 15 | 10 |
| Example 16 | 3 |
| Example 17 | 747 |
| Example 18 | 7 |
| Example 19 | 9 |
| Example 20 | 19 |
| Example 21 | 5 |
| Example 22 | 200 |
| Example 23 | 16 |
| Example 24 | 10 |
| Example 25 | 13 |
| Example 26 | 7 |
| Example 27 | 11 |

TABLE 3-continued

| Compound | $IC_{50}$ (nM) |
| --- | --- |
| Example 28 | 55 |
| Example 29 | 10 |
| Example 30 | 13 |
| Example 31 | 11 |
| Example 32 | 10 |
| Example 33 | 148 |
| Example 34 | 8 |
| Example 35 | 7 |
| Example 36 | 17 |
| Example 37 | 39 |
| Example 38 | 3 |
| Example 39 | 7 |
| Example 40 | 82 |
| Example 41 | 635 |
| Example 42 | 111 |
| Example 43 | 3 |
| Example 44 | 77 |
| Example 45 | 3 |
| Example 46 | 8 |
| Example 47 | 42 |
| Example 48 | 56 |
| Example 49 | 197 |
| Example 50 | 4 |
| Example 51 | 16 |
| Example 52 | 15 |
| Example 53 | 1 |
| Example 54 | 4 |
| Example 55 | 8 |
| Example 56 | 66 |
| Example 57 | 37 |
| Example 58 | 22 |
| Example 59 | 239 |
| Example 60 | 8 |
| Example 61 | 199 |
| Example 62 | 11 |
| Example 63 | 94 |
| Example 64 | 5 |
| Example 65 | 19 |
| Example 66 | 213 |
| Example 67 | >10,000 |
| Example 68 | 110 |
| Example 69 | 22 |
| Example 70 | 12 |
| Example 71 | >10,000 |
| Example 72 | 260 |
| Example 73 | 5 |
| Example 74 | 680 |
| Example 75 | 23 |
| Example 76 | 60 |
| Example 77 | 60 |
| Example 78 | 100 |
| Example 79 | 20 |
| Example 80 | 80 |
| Example 81 | 70 |
| Example 82 | 70 |
| Example 83 | 70 |
| Example 84 | 50 |
| Example 85 | 70 |
| Example 86 | 110 |
| Example 87 | 70 |
| Example 88 | >10,000 |
| Example 89 | 60 |
| Example 90 | 80 |
| Example 91 | 2800 |
| Example 92 | 188 |
| Example 93 | 98 |
| Example 94 | 3 |
| Example 95 | 90 |
| Example 96 | 60 |
| Example 97 | 70 |
| Example 98 | 1 |
| Example 99 | 40 |
| Example 100 | 320 |
| Example 101 | 40 |
| Example 102 | 260 |
| Example 103 | 20 |
| Example 104 | 33 |
| Example 105 | 60 |

TABLE 3-continued

| Compound | IC$_{50}$ (nM) |
|---|---|
| Example 106 | 150 |
| Example 107 | 25 |
| Example 108 | 3 |
| Example 109 | 15 |
| Example 110 | 14 |
| Example 111 | 9 |
| Example 112 | 5 |
| Example 113 | 1 |
| Example 114 | 42 |
| Example 115 | 67 |
| Example 116 | 48 |
| Example 117 | 3 |
| Example 118 | 20 |
| Example 119 | 249 |
| Example 120 | 1 |
| Example 121 | 5 |
| Example 122 | 306 |
| Example 123 | 3 |
| Example 124 | 44 |
| Example 125 | 2 |
| Example 126 | 47 |
| Example 127 | 1 |

As shown in Table 3, the compounds of the present invention exhibit an improved antagonism against MCH receptor. These results confirm that the imidazole derivative of the present invention is effective as an antagonist against a MCH receptor and can be used for the treatment of MCH-related diseases.

As described above, imidazole derivatives having aryl piperidine substituents are effective as an antagonist against a MCH receptor and compositions containing the imidazole derivatives as an active ingredient are useful for preventing and treating for MCH-related diseases.

What is claimed is:

1. An imidazole derivative of Formula (I), or a pharmaceutically acceptable salt thereof:

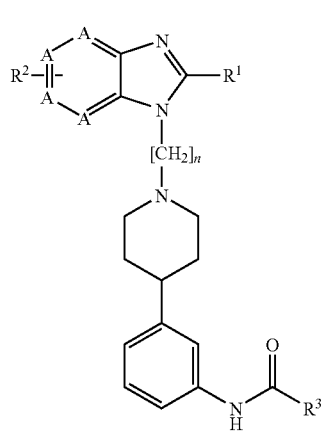

(I)

wherein
R$^1$ is

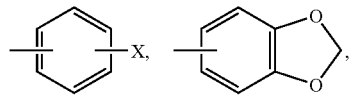

C$_{1-4}$ alkyl,

in which X is H, halogen, OR$^5$, C$_{1-4}$ alkyl, CF$_3$, phenyl, CN, NO$_2$, —CO$_2$R$^6$, or —CONR$^7$R$^8$, R$^5$, R$^6$, R$^7$ and R$^8$ being each independently H, halogen, C$_{1-3}$ alkyl, or phenyl;
R$^4$ is H, halogen, C$_{1-3}$ alkyl, C$_{1-3}$ alkoxy, phenyl, or phenyl having at least one halogen or methyl substituent;
W is CH or N;
Y is O, S, or NR$^9$, R$^9$ being H or C$_{1-3}$ alkyl;
m is 1 or 2;
R$^2$ is at least one selected from the group consisting of H, halogen, C$_{1-3}$ alkyl,

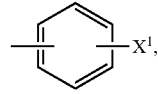

phenyl, OR$^5$, NO$_2$, CN, pyridyl, CHO, and —CONR$^7$R$^8$, in which X$^1$ is H, halogen, C$_{1-3}$ alkyl, OR$^5$, or NO$_2$, and R$^5$, R$^7$, and R$^8$ are the same as defined above;
R$^3$ is C$_{1-3}$ alkyl, phenyl, or phenyl having at least one halogen or methyl substituent;
A is CH or N, with the proviso that the number of N representing A does not exceed 2; and
n is an integer of 2 to 5.

2. The imidazole derivative or pharmaceutically acceptable salt thereof according to claim 1, wherein
R$^1$ is

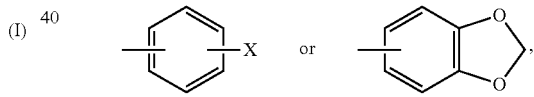

in which X is H, halogen, OR$^5$, C$_{1-4}$ alkyl, CF$_3$, phenyl, CN, NO$_2$, —CO$_2$R$^6$, or —CONR$^7$R$^8$, R$^5$, R$^6$, R$^7$ and R$^8$ being each independently H, halogen, C$_{1-3}$ alkyl, or phenyl; and
R$^2$ is at least one selected from the group consisting of H, halogen, C$_{1-3}$ alkyl, phenyl, OR$^5$, NO$_2$, CN, pyridyl, and —CONR$^7$R$^8$.

3. The imidazole derivative or pharmaceutically acceptable salt thereof according to claim 1, wherein
R$^1$ is C$_{1-4}$ alkyl; and
R$^2$ is at least one selected from the group consisting of H, halogen, C$_{1-3}$ alkyl,

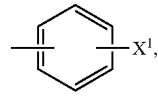

OR$^5$, NO$_2$, CN, pyridyl, CHO, and —CONR$^7$R$^8$, in which X$^1$ is H, halogen, C$_{1-3}$ alkyl, OR$^5$, or NO$_2$, and R$^5$, R$^7$ and R$^8$ are each independently H, C$_{1-3}$ alkyl, or phenyl.

4. The imidazole derivative or pharmaceutically acceptable salt thereof according to claim 1, wherein $R^1$ is

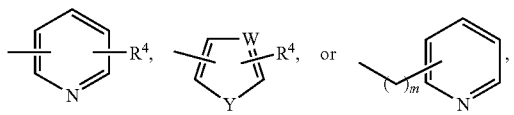

in which $R^4$ is H, halogen, $C_{1-3}$ alkyl, $C_{1-3}$ alkoxy, phenyl, or phenyl having at least one halogen or methyl substituent;
W is CH or N;
Y is O, S or $NR^9$, in which $R^9$ is H or $C_{1-3}$ alkyl;
m is 1 or 2; and
$R^2$ is at least one selected from the group consisting of H, halogen, $C_{1-3}$ alkyl, phenyl, $OR^5$, $NO_2$, CN, pyridyl, and $-CONR^7R^8$, $R^5$, $R^7$ and $R^8$ being each independently H, $C_{1-3}$ alkyl, or phenyl.

5. The imidazole derivative or pharmaceutically acceptable salt thereof according to claim 2, wherein
$R^5$ is H, methyl, or phenyl;
$R^6$ is H or methyl;
$R^7$ and $R^8$ are each H; and
the number of N representing A is 1.

6. The imidazole derivative or pharmaceutically acceptable salt thereof according to claim 2, being selected from the group consisting of:
1) 2-phenyl-1-{2-[4-(3-acetylaminophenyl)piperidin-1-yl]ethyl}-1H-benzimidazole;
2) 2-(4-chlorophenyl)-1-{2-[4-(3-acetylaminophenyl)piperidin-1-yl]ethyl}-1H-benzimidazole;
3) 2-phenyl-1-{3-[4-(3-acetylaminophenyl)piperidin-1-yl]propyl}-1H-benzimidazole;
4) 2-(4-chlorophenyl)-1-{3-[4-(3-acetylaminophenyl)piperidin-1-yl]propyl}-1H-benzimidazole;
5) 2-phenyl-1-{4-[4-(3-acetylaminophenyl)piperidin-1-yl]butyl}-1H-benzimidazole;
6) 2-(4-chlorophenyl)-1-{4-[4-(3-acetylaminophenyl)piperidin-1-yl]butyl}-1H-benzimidazole;
7) 2-phenyl-1-{5-[4-(3-acetylaminophenyl)piperidin-1-yl]pentyl}-1H-benzimidazole;
8) 2-(4-chlorophenyl)-1-{5-[4-(3-acetylaminophenyl)piperidin-1-yl]pentyl}-1H-benzimidazole;
9) 2-(2-chlorophenyl)-1-{3-[4-(3-acetylaminophenyl)piperidin-1-yl]propyl}-1H-benzimidazole;
10) 2-(3-chlorophenyl)-1-{3-[4-(3-acetylaminophenyl)piperidin-1-yl]propyl}-1H-benzimidazole;
11) 2-(4-bromophenyl)-1-{3-[4-(3-acetylaminophenyl)piperidin-1-yl]propyl}-1H-benzimidazole;
12) 2-(3,4-dichlorophenyl)-1-{3-[4-(3-acetylaminophenyl)piperidin-1-yl]propyl}-1H-benzimidazole;
13) 2-(3-bromophenyl)-1-{3-[4-(3-acetylaminophenyl)piperidin-1-yl]propyl}-1H-benzimidazole;
14) 2-(2-iodophenyl)-1-{3-[4-(3-acetylaminophenyl)piperidin-1-yl]propyl}-1H-benzimidazole;
15) 2-(2-fluorophenyl)-1-{3-[4-(3-acetylaminophenyl)piperidin-1-yl]propyl}-1H-benzimidazole;
16) 2-(2,4-dichlorophenyl)-1-{3-[4-(3-acetylaminophenyl)piperidin-1-yl]propyl}-1H-benzimidazole;
17) 2-(2-methoxyphenyl)-1-{3-[4-(3-acetylaminophenyl)piperidin-1-yl]propyl}-1H-benzimidazole;
18) 2-(3-methoxyphenyl)-1-{3-[4-(3-acetylaminophenyl)piperidin-1-yl]propyl}-1H-benzimidazole;
19) 2-(4-methoxyphenyl)-1-{3-[4-(3-acetylaminophenyl)piperidin-1-yl]propyl}-1H-benzimidazole;
20) 2-(4-isopropylphenyl)-1-{3-[4-(3-acetylaminophenyl)piperidin-1-yl]propyl}-1H-benzimidazole;
21) 2-phenyl-1-{3-[4-(3-acetylaminophenyl)piperidin-1-yl]propyl}-5,6-dimethyl-1H-benzimidazole;
22) 2-(4-chlorophenyl)-1-{3-[4-(3-acetylaminophenyl)piperidin-1-yl]propyl}-5,6-dimethyl-1H-benzimidazole;
23) 2-phenyl-1-{3-[4-(3-acetylaminophenyl)piperidin-1-yl]propyl}-6-methyl-1H-benzimidazole;
24) 2-(4-chlorophenyl)-1-{3-[4-(3-acetylaminophenyl)piperidin-1-yl]propyl}-6-methyl-1H-benzimidazole;
25) 2-(4-chlorophenyl)-1-{3-[4-(3-acetylaminophenyl)piperidin-1-yl]propyl}-6-chloro-1H-benzimidazole;
26) 2-phenyl-1-{3-[4-(3-acetylaminophenyl)piperidin-1-yl]propyl}-6-fluoro-1H-benzimidazole;
27) 2-phenyl-1-{3-[4-(3-acetylaminophenyl)piperidin-1-yl]propyl}-6-methoxy-1H-benzimidazole;
28) 2-(4-chlorophenyl)-1-{3-[4-(3-acetylaminophenyl)piperidin-1-yl]propyl}-6-methoxy-1H-benzimidazole;
29) 2-phenyl-1-{3-[4-(3-acetylaminophenyl)piperidin-1-yl]propyl}-6-chloro-1H-benzimidazole;
30) 2-(4-fluorophenyl)-1-{3-[4-(3-acetylaminophenyl)piperidin-1-yl]propyl}-6-chloro-1H-benzimidazole;
31) 2-(4-chlorophenyl)-1-{3-[4-(3-acetylaminophenyl)piperidin-1-yl]propyl}-6-fluoro-1H-benzimidazole;
32) 2-phenyl-1-{3-[4-(3-acetylaminophenyl)piperidin-1-yl]propyl}-6-nitro-1H-benzimidazole;
33) 2-(2-fluorophenyl)-1-{3-[4-(3-acetylaminophenyl)piperidin-1-yl]propyl}-6-chloro-1H-benzimidazole;
34) 2-(3-fluorophenyl)-1-{3-[4-(3-acetylaminophenyl)piperidin-1-yl]propyl}-6-chloro-1H-benzimidazole;
35) 2-(3-chlorophenyl)-1-{3-[4-(3-acetylaminophenyl)piperidin-1-yl]propyl}-6-chloro-1H-benzimidazole;
36) 2-(4-chlorophenyl)-1-{3-[4-(3-acetylaminophenyl)piperidin-1-yl]propyl}-6-bromo-1H-benzimidazole;
37) 2-(2-chlorophenyl)-1-{3-[4-(3-acetylaminophenyl)piperidin-1-yl]propyl}-5,6-dimethyl-1H-benzimidazole;
38) 2-(3-chlorophenyl)-1-{3-[4-(3-acetylaminophenyl)piperidin-1-yl]propyl}-5,6-dimethyl-1H-benzimidazole;
39) 2-(4-chlorophenyl)-1-{3-[4-(3-acetylaminophenyl)piperidin-1-yl]propyl}-4,5-dimethyl-1H-benzimidazole;
40) 2-(2-chlorophenyl)-1-{3-[4-(3-acetylaminophenyl)piperidin-1-yl]propyl}-6-nitro-1H-benzimidazole;
41) 2-(3-chlorophenyl)-1-{3-[4-(3-acetylaminophenyl)piperidin-1-yl]propyl}-6-nitro-1H-benzimidazole;
42) 2-(4-chlorophenyl)-1-{3-[4-(3-acetylaminophenyl)piperidin-1-yl]propyl}-6-nitro-1H-benzimidazole;
43) 2-phenyl-1-{3-[4-(3-acetylaminophenyl)piperidin-1-yl]propyl}-6-bromo-1H-benzimidazole;
44) 2-(2,3,4,5-tetrafluorophenyl)-1-{3-[4-(3-acetylaminophenyl)piperidin-1-yl]propyl}-1H-benzimidazole;
45) 2-(4-trifluoromethylphenyl)-1-{3-[4-(3-acetylaminophenyl)piperidin-1-yl]propyl}-1H-benzimidazole;
46) 2-(4-biphenyl)-1-{3-[4-(3-acetylaminophenyl)piperidin-1-yl]propyl}-1H-benzimidazole;
47) 2-(4-phenoxyphenyl)-1-{3-[4-(3-acetylaminophenyl)piperidin-1-yl]propyl}-1H-benzimidazole;
48) 2-(4-fluorophenyl)-1-{3-[4-(3-acetylaminophenyl)piperidin-1-yl]propyl}-1H-benzimidazole;
49) 2-(4-chlorophenyl)-1-{3-[4-(3-acetylaminophenyl)piperidin-1-yl]propyl}-5,7-dimethyl-1H-benzimidazole;
50) 2-(3,4-difluorophenyl)-1-{3-[4-(3-acetylaminophenyl)piperidin-1-yl]propyl}-1H-benzimidazole;
51) 2-(4-cyanophenyl)-1-{3-[4-(3-acetylaminophenyl)piperidin-1-yl]propyl}-1H-benzimidazole;
52) 2-(3-cyanophenyl)-1-{3-[4-(3-acetylaminophenyl)piperidin-1-yl]propyl}-1H-benzimidazole;
53) 2-(4-chloro-2-fluorophenyl)-1-{3-[4-(3-acetylaminophenyl)piperidin-1-yl]propyl}-1H-benzimidazole;

54) 2-(2-chloro-4-fluorophenyl)-1-{3-[4-(3-acetylaminophenyl)piperidin-1-yl]propyl}-1H-benzimidazole;
55) 2-(3-nitrophenyl)-1-{3-[4-(3-acetylaminophenyl)piperidin-1-yl]propyl}-1H-benzimidazole;
56) 2-(5-chloro-2-methoxyphenyl)-1-{3-[4-(3-acetylaminophenyl)piperidin-1-yl]propyl}-1H-benzimidazole;
57) 2-(2-chloro-4-nitrophenyl)-1-{2-[4-(3-acetamidophenyl)piperidin-1-yl]propyl}-1H-benzimidazole;
58) 2-(2,4-dimethoxyphenyl)-1-{3-[4-(3-acetylaminophenyl)piperidin-1-yl]propyl}-1H-benzimidazole;
59) 2-(4-chloro-2-fluorophenyl)-1-{3-[4-(3-acetylaminophenyl)piperidin-1-yl]propyl}-5,6-dimethyl-1H-benzimidazole;
60) 2-(4-chlorophenyl)-1-{3-[4-(3-acetylaminophenyl)piperidin-1-yl]propyl}-5-carbamoyl-1H-benzimidazole;
61) 2-(4-chlorophenyl)-1-{3-[4-(3-acetylaminophenyl)piperidin-1-yl]propyl}-6-carbamoyl-1H-benzimidazole;
62) 2-(3-carbamoylphenyl)-1-{3-[4-(3-acetylaminophenyl)piperidin-1-yl]propyl}-1H-benzimidazole;
63) 2-(2-hydroxyphenyl)-1-{3-[4-(3-acetylaminophenyl)piperidin-1-yl]propyl}-1H-benzimidazole;
64) 2-(4-chlorophenyl)-1-{3-[4-(3-isobutyrylaminophenyl)piperidin-1-yl]propyl}-1H-benzimidazole;
65) 2-(4-chlorophenyl)-1-{3-[4-(3-benzoylaminophenyl)piperidin-1-yl]propyl}-1H-benzimidazole;
66) 2-(4-chlorophenyl)-1-{3-[4-(3-(3-chlorobenzoylamino)phenyl)piperidin-1-yl]propyl}-1H-benzimidazole;
67) 2-(4-chlorophenyl)-1-{3-[4-(3-(4-methylbenzoylamino)phenyl)piperidin-1-yl]propyl}-1H-benzimidazole;
68) 6-bromo-5-methyl-2-phenyl-3-{3-[4-(3-acetylaminophenyl)piperidin-1-yl]propyl}-3H-imidazo[4,5-b]pyridine;
69) 5-methyl-2-phenyl-3-{3-[4-(3-acetylaminophenyl)piperidin-1-yl]propyl}-3H-imidazo[4,5-b]pyridine;
70) 2-(benzo[1,3]dioxol-5-yl)-1-{3-[4-(3-acetylaminophenyl)piperidin-1-yl]propyl}-1H-benzimidazole;
71) 2-(4-chlorophenyl)-1-{2-[4-(3-isobutyrylaminophenyl)piperidin-1-yl]ethyl}-1H-benzimidazole;
72) 2-phenyl-3-{3-[4-(3-acetylaminophenyl)piperidin-1-yl]propyl}-3H-imidazo[4,5-c]pyridine;
73) 2-phenyl-3-{3-[4-(3-acetylaminophenyl)piperidin-1-yl]propyl}-3H-imidazo[4,5-d]pyridine;
74) 5-bromo-6-methyl-2-phenyl-3-{3-[4-(3-acetylaminophenyl)piperidin-1-yl]propyl}-3H-imidazo[4,5-e]pyridine;
75) 6-methyl-2-phenyl-3-{3-[4-(3-acetylaminophenyl)piperidin-1-yl]propyl}-3H-imidazo[4,5-e]pyridine;
76) 2-(3-methoxycarbonylphenyl)-1-{3-[4-(3-acetylaminophenyl)piperidin-1-yl]propyl}-1H-benzimidazole;
77) 2-(4-ethylphenyl)-1-{3-[4-(3-acetylaminophenyl)piperidin-1-yl]propyl}-1H-benzimidazole;
78) 2-(4-cyanophenyl)-1-{3-[4-(3-acetylaminophenyl)piperidin-1-yl]propyl}-5,6-dimethyl-1H-benzimidazole;
79) 2-(m-tolyl)-1-{3-[4-(3-acetylaminophenyl)piperidin-1-yl]propyl}-1H-benzimidazole;
80) 2-(2-chloro-4-fluorophenyl)-1-{3-[4-(3-acetylaminophenyl)piperidin-1-yl]propyl}-5,6-dimethyl-1H-benzimidazole;
81) 2-(4-chlorophenyl)-1-{3-[4-(3-acetylaminophenyl)piperidin-1-yl]propyl}-5-cyano-1H-benzimidazole;
82) 2-(4-chlorophenyl)-1-{3-[4-(3-acetylaminophenyl)piperidin-1-yl]propyl}-6-cyano-1H-benzimidazole;
83) 2-(4-chlorophenyl)-1-{3-[4-(3-acetylaminophenyl)piperidin-1-yl]propyl}-5-fluoro-1H-benzimidazole;
84) 2-(4-fluorophenyl)-1-{3-[4-(3-acetylaminophenyl)piperidin-1-yl]propyl}-5-chloro-1H-benzimidazole;
85) 2-(4-chlorophenyl)-1-{3-[4-(3-acetylaminophenyl)piperidin-1-yl]propyl}-5-nitro-1H-benzimidazole;
86) 2-(4-chloro-2-methoxyphenyl)-1-{3-[4-(3-acetylaminophenyl)piperidin-1-yl]propyl}-5,6-dimethyl-1H-benzimidazole;
87) 2-(5-chloro-2-methoxyphenyl)-1-{3-[4-(3-acetylaminophenyl)piperidin-1-yl]propyl}-5,6-dimethyl-1H-benzimidazole.

7. The imidazole derivative or pharmaceutically acceptable salt thereof according to claim 3, wherein $R^5$ is H, methyl, or phenyl;
$R^7$ and $R^8$ are each H;
$R^2$ is at least one selected from the group consisting of H, halogen, $C_{1-3}$ alkyl,

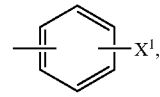

$OR^5$, $NO_2$, CN, pyridyl, and —$CONR^7R^8$, $X^1$ being H, halogen, methyl, or $NO_2$; and
the number of N representing A is 1.

8. The imidazole derivative or pharmaceutically acceptable salt thereof according to claim 3, being selected from the group consisting of:
1) 2-methyl-1-{3-[4-(3-acetylaminophenyl)piperidin-1-yl]propyl}-1H-benzimidazole;
2) 2-methyl-1-{3-[4-(3-acetylaminophenyl)piperidin-1-yl]propyl}-5,6-dimethyl-1H-benzimidazole;
3) 2-methyl-1-{3-[4-(3-isobutyrylaminophenyl)piperidin-1-yl]propyl}-1H-benzimidazole;
4) 2,5-dimethyl-3-{3-[4-(3-acetylaminophenyl)piperidin-1-yl]propyl}-3H-imidazo[4,5-b]pyridine;
5) 6-bromo-2,5-dimethyl-3-{3-[4-(3-acetylaminophenyl)piperidin-1-yl]propyl}-3H-imidazo[4,5-b]pyridine;
6) 6-bromo-2-ethyl-5-methyl-3-{3-[4-(3-acetylaminophenyl)piperidin-1-yl]propyl}-3H-imidazo[4,5-b]pyridine;
7) 6-bromo-2-butyl-5-methyl-3-{3-[4-(3-acetylaminophenyl)piperidin-1-yl]propyl}-3H-imidazo[4,5-b]pyridine;
8) 2-butyl-5,7-dimethyl-3-{3-[4-(3-acetylaminophenyl)piperidin-1-yl]propyl}-3H-imidazo[4,5-b]pyridine;
9) 2-butyl-5,7-dimethyl-6-phenyl-3-{3-[4-(3-acetylaminophenyl)piperidin-1-yl]propyl}-3H-imidazo[4,5-b]pyridine;
10) 2-butyl-5-methyl-6-pyridin-2-yl-3-{3-[4-(3-acetylaminophenyl)piperidin-1-yl]propyl}-3H-imidazo[4,5-b]pyridine;
11) 6-bromo-2-butyl-5-methyl-3-{3-[4-(3-isobutyrylaminophenyl)piperidin-1-yl]propyl}-3H-imidazo[4,5-b]pyridine;
12) 2-butyl-5,7-dimethyl-3-{3-[4-(3-isobutyrylaminophenyl)piperidin-1-yl]propyl}-3H-imidazo[4,5-b]pyridine;
13) 2-butyl-5,7-dimethyl-6-phenyl-3-{3-[4-(3-isobutyrylaminophenyl)piperidin-1-yl]propyl}-3H-imidazo[4,5-b]pyridine;
14) 2-butyl-5-methyl-6-pyridin-2-yl-3-{3-[4-(3-isobutyrylaminophenyl)piperidin-1-yl]propyl}-3H-imidazo[4,5-b]pyridine;

15) 2-butyl-5-formyl-6-phenyl-3-{3-[4-(3-isobutyrylaminophenyl)piperidin-1-yl]propyl}-3H-imidazo[4,5-b]pyridine;
16) 2-butyl-5-methyl-6-(4-nitrophenyl)-3-{3-[4-(3-isobutyrylaminophenyl)piperidin-1-yl]propyl}-3H-imidazo[4,5-b]pyridine.

9. The imidazole derivative or pharmaceutically acceptable salt thereof according to claim 4, wherein
   $R^4$ is halogen, $OCH_3$, or methyl;
   $R^5$ is H, methyl, or phenyl;
   $R^7$ and $R^8$ are each H;
   $R^9$ is H or methyl;
   $R^3$ is $C_{1-3}$ alkyl; and
   A is CH.

10. The imidazole derivative or pharmaceutically acceptable salt thereof according to claim 4, being selected from the group consisting of:
   1) 2-(pyridin-2-yl)-1-{3-[4-(3-acetamidophenyl)piperidin-1-yl]propyl}-1H-benzimidazole;
   2) 2-(pyridin-3-yl)-1-{3-[4-(3-acetamidophenyl)piperidin-1-yl]propyl}-1H-benzimidazole;
   3) 2-(pyridin-4-yl)-1-{3-[4-(3-acetamidophenyl)piperidin-1-yl]propyl}-1H-benzimidazole;
   4) 2-(furan-3-yl)-1-{3-[4-(3-acetylaminophenyl)piperidin-1-yl]propyl}-1H-benzimidazole;
   5) 2-(5-bromofuran-2-yl)-1-{3-[4-(3-acetylaminophenyl)piperidin-1-yl]propyl}-1H-benzimidazole;
   6) 2-(thiophen-2-yl)-1-{3-[4-(3-acetylaminophenyl)piperidin-1-yl]propyl}-1H-benzimidazole;
   7) 2-(5-methylthiophen-2-yl)-1-{3-[4-(3-acetylaminophenyl)piperidin-1-yl]propyl}-1H-benzimidazole;
   8) 2-(1-methyl-1H-pyrrol-2-yl)-1-{3-[4-(3-acetylaminophenyl)piperidin-1-yl]propyl}-1H-benzimidazole;
   9) 2-(5-bromopyridin-3-yl)-1-{3-[4-(3-acetylaminophenyl)piperidin-1-yl]propyl}-1H-benzimidazole;
   10) 2-(6-chloropyridin-3-yl)-1-{3-[4-(3-acetamidophenyl)piperidin-1-yl]propyl}-1H-benzimidazole;
   11) 2-(6-methylpyridin-3-yl)-1-{3-[4-(3-acetamidophenyl)piperidin-1-yl]propyl}-1H-benzimidazole;
   12) 2-(2-methoxypyridin-3-yl)-1-{3-[4-(3-acetamidophenyl)piperidin-1-yl]propyl}-1H-benzimidazole;
   13) 5-chloro-2-(pyridin-3-yl)-1-{3-[4-(3-acetamidophenyl)piperidin-1-yl]propyl}-1H-benzimidazole;
   14) 5-nitro-2-(pyridin-3-yl)-1-{3-[4-(3-acetamidophenyl)piperidin-1-yl]propyl}-1H-benzimidazole;
   15) 5-chloro-2-(5-bromofuran-2-yl)-1-{3-[4-(3-acetamidophenyl)piperidin-1-yl]propyl}-1H-benzimidazole;
   16) 2-(furan-2-yl)-5-methoxy-1-{3-[4-(3-acetamidophenyl)piperidin-1-yl]propyl}-1H-benzimidazole;
   17) 5-methyl-2-(thiophen-3-yl)-1-{3-[4-(3-acetamidophenyl)piperidin-1-yl]propyl}-1H-benzimidazole;
   18) 5,6-dimethyl-2-(1-methylpyrrol-2-yl)-1-{3-[4-(3-acetamidophenyl)piperidin-1-yl]propyl}-1H-benzimidazole;
   19) 2-(thiazol-4-yl)-1-{3-[4-(3-acetamidophenyl)piperidin-1-yl]propyl}-1H-benzimidazole;
   20) 2-(4-methyloxazol-5-yl)-1-{3-[4-(3-acetamidophenyl)piperidin-1-yl]propyl}-1H-benzimidazole;
   21) 2-(1-methyl-1H-imidazol-5-yl)-1-{3-[4-(3-acetamidophenyl)piperidin-1-yl]propyl}-1H-benzimidazole;
   22) 2-(pyridin-2-ylmethyl)-1-{3-[4-(3-acetamidophenyl)piperidin-1-yl]propyl}-1H-benzimidazole;
   23) 2-(pyridin-3-ylmethyl)-1-{3-[4-(3-acetamidophenyl)piperidin-1-yl]propyl}-1H-benzimidazole; and
   24) 2-[2-(pyridin-3-yl)ethyl]-1-{3-[4-(3-acetamidophenyl)piperidin-1-yl]propyl}-1H-benzimidazole.

11. A process for preparing the imidazole derivative of formula (I) according to claim 1 comprising subjecting an imidazole derivative of formula (II) to a reaction with a compound of formula (III) in a solvent in the presence of a base:

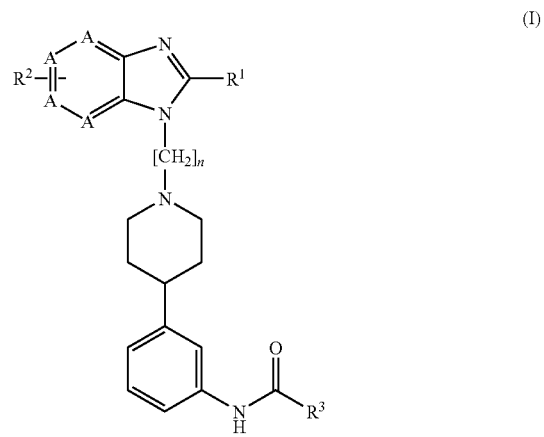

(I)

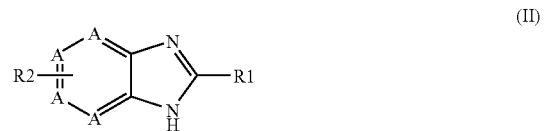

(II)

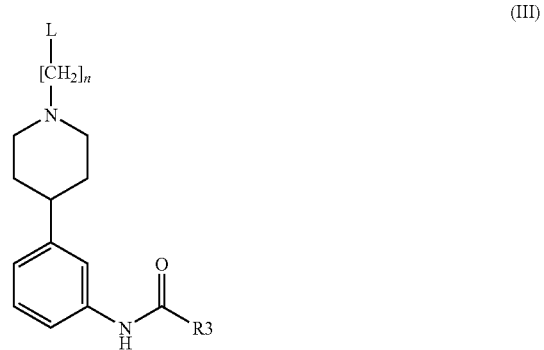

(III)

wherein
$R^1$, $R^2$, $R^3$, A and n are the same as defined in claim 1, and L is halogen, OMs or OTs.

12. A process for preparing an imidazole derivative of formula (I) comprising subjecting an imidazole derivative of formula (IV) to a reaction with a compound of formula (V) in a solvent in the presence of a base:

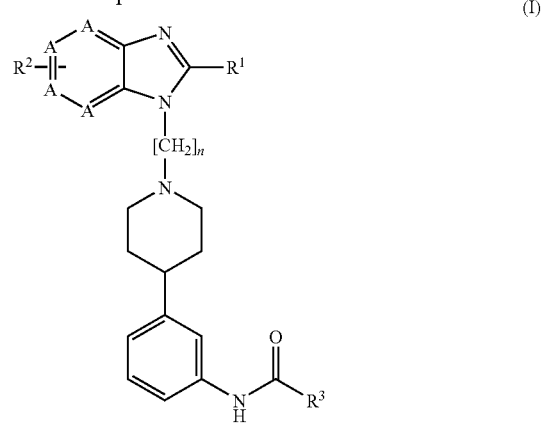

(I)

-continued

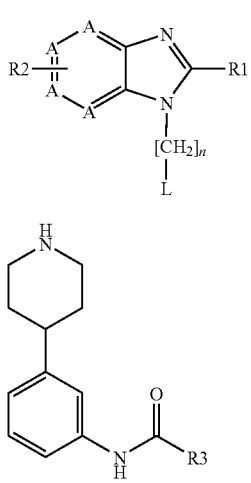

(IV)

(V)

wherein $R^1$, $R^2$, $R^3$, A and n are the same as defined in claim 1, and L is halogen, OMs or OTs.

13. The process for preparing imidazole derivative according to claim 11, wherein the base is an organic base selected from pyridine, triethylamine, N,N-diisopropylethylamine, 1,8-diazabicyclo-[5.4.0]undec-7-ene (DBU), and a mixture thereof; or an inorganic base selected from NaOH, $Na_2CO_3$, $K_2CO_3$, $Cs_2CO_3$, and a mixture thereof.

14. The process for preparing the imidazole derivative according to claim 11, wherein the solvent is an ether-based solvent, dimethylformamide (DMF), dimethylsulfoxide, acetonitrile, or a mixture thereof.

15. A composition comprising the imidazole derivative or pharmaceutically acceptable salt thereof according to claim 1 and a pharmaceutically acceptable excipient.

16. The process for preparing imidazole derivative according to claim 12, wherein the base is an organic base selected from pyridine, triethylamine, N,N-diisopropylethylamine, 1,8-diazabicyclo-[5.4.0]undec-7-ene (DBU), and a mixture thereof; or an inorganic base selected from NaOH, $Na_2CO_3$, $K_2CO_3$, $Cs_2CO_3$, and a mixture thereof.

17. The process for preparing the imidazole derivative according to claim 12, wherein the solvent is an ether-based solvent, dimethylformamide (DMF), dimethylsulfoxide, acetonitrile, or a mixture thereof.

* * * * *